US009206166B2

(12) United States Patent
Wang et al.

(10) Patent No.: US 9,206,166 B2
(45) Date of Patent: Dec. 8, 2015

(54) CERTAIN PROTEIN KINASE INHIBITORS

(71) Applicants: SHANGHAI FOCHON PHARMACEUTICAL CO., LTD., Shanghai (CN); SHANGHAI iNSTITUTE OF MATERIA MEDICA CHINESE ACADEMY OF SCIENCES, Shanghai (CN)

(72) Inventors: Weibo Wang, Moraga, CA (US); Meiyu Geng, Shanghai (CN); Jian Ding, Shanghai (CN); Xingdong Zhao, Moraga, CA (US); Jing Ai, Shanghai (CN); Qiang Tian, Chongqing (CN); Xia Peng, Shanghai (CN); Weipeng Zhang, Chongqing (CN); Hongbin Liu, Chongqing (CN); Haohan Tan, Chongqing (CN); Ling Chen, Chongqing (CN)

(73) Assignees: Shanghai Institute of Materia Medica Academy of Sciences, Shanghai (CN); Shanghai Fochon Pharmaceutical Co., LTD, Shanghai (CN)

(*) Notice: Subject to any disclaimer, the term of this patent is extended or adjusted under 35 U.S.C. 154(b) by 0 days.

(21) Appl. No.: 14/071,953

(22) Filed: Nov. 5, 2013

(65) Prior Publication Data
US 2014/0128387 A1    May 8, 2014

Related U.S. Application Data

(60) Provisional application No. 61/723,099, filed on Nov. 6, 2012.

(51) Int. Cl.
A61K 31/506    (2006.01)
C07D 405/12    (2006.01)
A61K 31/519    (2006.01)
A61K 31/5377   (2006.01)
A61K 45/06     (2006.01)
C07D 405/14    (2006.01)
C07D 487/04    (2006.01)

(52) U.S. Cl.
CPC ............ *C07D 405/12* (2013.01); *A61K 31/506* (2013.01); *A61K 31/519* (2013.01); *A61K 31/5377* (2013.01); *A61K 45/06* (2013.01); *C07D 405/14* (2013.01); *C07D 487/04* (2013.01)

(58) Field of Classification Search
CPC .. C07D 405/12; C07D 405/14; C07D 487/04; A61K 31/506; A61K 31/519; A61K 31/5377; A61K 45/06
USPC .................. 544/323, 324; 514/275
See application file for complete search history.

(56) References Cited

FOREIGN PATENT DOCUMENTS

| WO | WO 2004080980 A1 * | 9/2004 |
|----|---------------------|--------|
| WO | WO 2008016894 A2 * | 2/2008 |
| WO | WO 2008051547 A1 * | 5/2008 |
| WO | WO 2008/073687     | 6/2008 |
| WO | WO 2009/032703     | 3/2009 |
| WO | WO 2009/097287     | 8/2009 |
| WO | WO 2009/099801     | 8/2009 |
| WO | WO 2009/126514     | 10/2009 |
| WO | WO 2009/126515     | 10/2009 |
| WO | WO 2009/140128     | 11/2009 |
| WO | WO 2009/158431     | 12/2009 |
| WO | WO 2010/002655     | 1/2010 |
| WO | WO 2011/014795     | 2/2011 |
| WO | WO 2011/015652     | 2/2011 |
| WO | WO 2011/018454     | 2/2011 |
| WO | WO 2011/020861     | 2/2011 |
| WO | WO 2011/029915     | 3/2011 |
| WO | WO 2012/082972     | 6/2012 |
| WO | WO 2012/106540     | 8/2012 |

OTHER PUBLICATIONS

Chemotherapy of Neoplastic Diseases in, Goodman & Gilman's: The Pharmacological Basis of Therapeutics 853-908 (L.L. Brunton et al., eds., 11th ed., 2008).*
J.H. Poupaert, Drug Design: Basic Principles and Applications, in 2 Encyclopedia of Pharmaceutical Technology 1362-1369, 1367 (James Swarbrick ed., 3rd ed., 2007).*
B.A. Chabner et al., Chemotherapy of Neoplastic Diseases, Neoplastic Agents in, Goodman & Gilman's: The Pharmacological Basis of Therapeutics 1315-1403, 1315 (L.L. Brunton et al., eds., 11th ed., 2006).*
Kinase Inhibitors, Methods in Molecular Biology 795 (B. Kuster ed., 2012).*
L. Lamant et al., 18 Leukemia, 1693-1698 (2004).*
R. Piva et al., 107 Blood 689-697 (2006).*
H. Hermann, 86 Blood, 1694-1700 (1995).*
A Rosenwald et al., 94 Blood, 362-364 (1999).*
G.S. Wood, 88 Blood, 1765-1770 (1996).*
R.E. George et al., 455 Nature, 975-978 (2008).*
E.L. Kwak et al., 363 New England Journal of Medicine, 1693-1703 (2010).*
K. Pulford et al., Antibody Techniques Used in the Study of Anaplastic Lymphoma Kinase-Positive ALCL in, Lymphoma : Methods and Protocols (T. Illidge et al., eds., 2005).*
J-O Lee et al., 6 Journal of Thoracic Oncology, 1474-1480 (2011).*

(Continued)

*Primary Examiner* — Alexander R Pagano
(74) *Attorney, Agent, or Firm* — Finnegan, Henderson, Farabow, Garrett & Dunner LLP

(57) ABSTRACT

Disclosed herein are protein kinase inhibitors, more particularly novel pyrimidine derivatives and pharmaceutical compositions thereof, and method of use thereof.

20 Claims, 1 Drawing Sheet

(56) References Cited

OTHER PUBLICATIONS

Oxford English Dictionary (OED Online, 3rd ed., Sep. 2002).*
G. Piccinini et al., 277 The Journal of Biological Chemistry, 22231-22239 (2002).*
J. Cools et al., 34 Genes, Chromosomes & Cancer, 354-362 (2002).*
A.T. Shaw et al., 17 Clinical Cancer Research, 2081-2086 (2011).*
J.G. Christensen et al., 6 Molecular Cancer Therapeutics, 3314-3322 (2007).*
H. Sakamoto et al., 19 Cancer Cell, 679-690 (2011).*
H. Mano, 99 Cancer Science, 2349-2355 (2008).*
T.H. Marsilje et al., Journal of Medicinal Chemistry, 5675-5690 (2013).*
J. Luo et al., 36 Cell, 823-837 (2009).*
National Cancer Institute (http://www.cancer.gov/) (Downloaded May 29, 2014).*
H.A. Fine, Neoplasms of the Central Nervous System in, 2 Cancer Principles & Practice of Oncology 1834-1887 (V.T. DeVita, Jr. et al. eds., 5th ed., 2005).*
Pulford et al., "The emerging normal and disease-related roles of anaplastic lymphoma kinase." Cell Mol. Life Sci. Dec. 2004 61(23):2939-53.

* cited by examiner

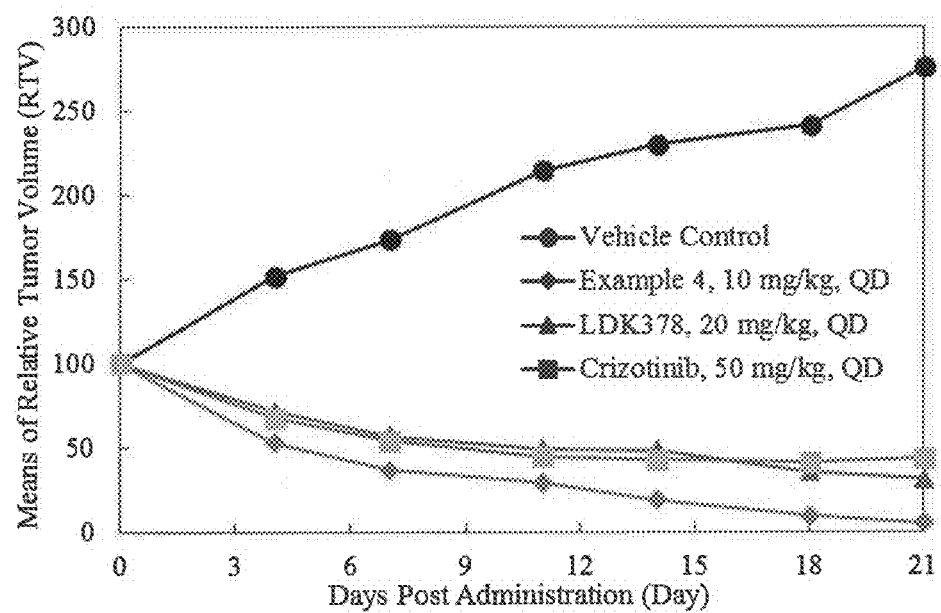

CERTAIN PROTEIN KINASE INHIBITORS

This application claims the benefit of U.S. Provisional Application No. 61/723,099, filed Nov. 6, 2012, which is incorporated herein by reference in its entirety.

Disclosed herein are protein kinase inhibitors, more particularly novel pyrimidine derivatives and pharmaceutical compositions thereof, and their use as pharmaceuticals.

Anaplastic lymphoma kinase (ALK), a member of the insulin receptor superfamily of receptor tyrosine kinases, has been implicated in oncogenesis in hematopoietic and non-hematopoietic tumors. The aberrant expression of full-length ALK receptor proteins has been reported in neuroblastomas and glioblastomas; and ALK fusion proteins have occurred in anaplastic large cell lymphoma. The study of ALK fusion proteins has also raised the possibility of new therapeutic treatments for patients with ALK-positive malignancies. (Pulford et al., Cell. Mol. Life. Sci. 61:2939-2953 (2004)).

Because of the emerging disease-related roles of ALK, there is a continuing need for compounds which may be useful for treating and preventing a disease which responds to inhibition of ALK and have at least one advantageous property selected from potency, stability, selectivity, toxicity, pharmacodynamics properties and pharmacokinetics properties as an alternative. In this regard, a novel class of ALK inhibitors is provided herein.

Disclosed herein are certain novel pyrimidine derivatives and pharmaceutical compositions thereof, and their use as pharmaceuticals.

In one aspect, disclosed herein is at least one compound of formula (I):

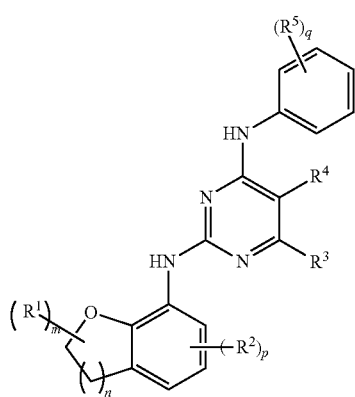

(I)

and/or at least one pharmaceutically acceptable salt thereof, wherein:

each $R^1$ is independently selected from:
hydrogen,
halogen,
hydroxyl,
$C_{1-10}$ alkyl,
$C_{3-10}$ cycloalkyl,
$C_{3-10}$ cycloalkyl-alkyl,
heterocyclyl,
heterocyclylalkyl
aryl,
arylalkyl,
heteroaryl, and
heteroarylalkyl,
wherein alkyl, cycloalkyl, and heterocyclyl are each unsubstituted or substituted with at least one substituent, such as one, two, three, or four substituents, independently selected from $R^{6a}$, and wherein aryl and heteroaryl are each unsubstituted or substituted with at least one substituent, such as one, two, three, or four substituents, independently selected from $R^{6b}$;

each $R^2$ is independently selected from:
hydrogen,
halogen,
hydroxyl,
$C_{1-10}$ alkyl,
$C_{2-10}$ alkenyl,
$C_{2-10}$ alkynyl,
$C_{3-10}$ cycloalkyl,
$C_{3-10}$ cycloalkylalkyl,
heterocyclyl,
heterocyclylalkyl
heterocyclylcarbonyl,
aryl,
heteroaryl,
arylalkyl, and
heteroarylalkyl,
wherein alkyl, alkenyl, alkynyl, cycloalkyl, and heterocyclyl are each unsubstituted or substituted with at least one substituent, such as one, two, three, or four substituents, independently selected from $R^{6a}$, and each aryl and heteroaryl is unsubstituted or substituted with at least one substituent, such as one, two, three, or four substituents, independently selected from $R^{6b}$;

each $R^3$ is independently selected from:
hydrogen,
halogen,
—CN,
—$NR^7R^8$, and
$C_{1-10}$ alkyl;
wherein alkyl is unsubstituted or substituted with at least one substituent, such as one, two, three, or four substituents, independently selected from $R^{6a}$;

each $R^4$ is independently selected from:
hydrogen,
halogen,
—CN,
$C_{1-10}$ alkyl,
$C_{2-10}$ alkenyl,
$C_{2-10}$ alkynyl, and
$C_{3-10}$ cycloalkyl;
wherein $C_{1-10}$ alkyl, $C_{2-10}$ alkenyl, $C_{2-10}$ alkynyl, and $C_{3-10}$ cycloalkyl are each unsubstituted or substituted with at least one substituent, such as one, two, three, or four substituents, independently selected from $R^{6a}$;

or $R^3$ and $R^4$ together with the carbon atoms to which they are attached form a 5-6 membered ring containing 0, 1, 2 or 3 heteroatoms independently selected from oxygen, sulfur and nitrogen, and optionally substituted with 1-2 $R^{6b}$ groups;

each $R^5$ is independently selected from:
hydrogen,
$C_{1-10}$ alkyl,
$C_{2-10}$ alkenyl,
$C_{2-10}$ alkynyl, $C_{3-10}$ cycloalkyl,
—$OR^8$,
—$NR^8S(O)_rR^8$,
—$NO_2$,
halogen,
—$S(O)_rR^7$,
—$SR^8$,
—$S(O)_2OR^7$,
—$OS(O)_2R^8$,
—$S(O)_rNR^7R^8$, —NR$^7$R$^8$,
—O(CR$^9$R$^{10}$)$_t$NR$^7$R$^8$,
—C(O)R$^7$,
—CO$_2$R$^8$,
—CO$_2$(CR$^9$R$^{10}$)$_t$CONR$^7$R$^8$,
—OC(O)R$^7$,
—CN,
—C(O)NR$^7$R$^8$,
—NR$^7$C(O)R$^8$,
—OC(O)NR$^7$R$^8$,
—NR$^7$C(O)OR$^8$,
—NR$^7$C(O)NR$^7$R$^8$,
—CR$^7$(N—OR$^8$),
—CHF$_2$,
—CF$_3$,
—OCHF$_2$, and
—OCF$_3$;
wherein C$_{1-10}$ alkyl, C$_{2-10}$ alkenyl, C$_{2-10}$ alkynyl, and C$_{3-10}$ cycloalkyl are each unsubstituted or substituted with at least one substituent, such as one, two, three, or four substituents, independently selected from R$^{6a}$;
each R$^{6a}$ is independently selected from:
C$_{1-10}$ alkyl,
C$_{2-10}$ alkenyl,
C$_{2-10}$ alkynyl,
C$_{3-10}$ cycloalkyl,
—OR$^8$,
—NR$^7$S(O)$_r$R$^8$,
—NO$_2$,
halogen,
—S(O)$_r$R$^7$,
—SR$^8$,
—S(O)$_2$OR$^7$,
—OS(O)$_2$R$^8$,
—S(O)$_r$NR$^7$R$^8$,
—NR$^7$R$^8$,
—(CR$^9$R$^{10}$)$_t$OR$^8$,
—(CR$^9$R$^{10}$)$_t$NR$^7$R$^8$,
—(CR$^9$R$^{10}$)$_t$SR$^8$,
—(CR$^9$R$^{10}$)$_t$S(O)$_r$R$^8$,
—(CR$^9$R$^{10}$)$_t$CO$_2$R$^8$,
—(CR$^9$R$^{10}$)$_t$CONR$^7$R$^8$,
—(CR$^9$R$^{10}$)$_t$NR$^7$CO$_2$R$^8$,
—(CR$^9$R$^{10}$)$_t$OCONR$^7$R$^8$,
—(CR$^9$R$^{10}$)$_t$NR$^1$CONR$^7$R$^8$,
—(CR$^9$R$^{10}$)$_t$NR$^7$SO$_2$NR$^7$R$^8$,
—O(CR$^9$R$^{10}$)$_t$NR$^7$R$^8$,
—C(O)R$^7$,
—C(O)(CR$^9$R$^{10}$)$_t$OR$^8$,
—C(O)(CR$^9$R$^{10}$)$_t$NR$^7$R$^8$,
—C(O)(CR$^9$R$^{10}$)$_t$SR$^8$,
—C(O)(CR$^9$R$^{10}$)$_t$S(O)$_r$R$^8$,
—CO$_2$R$^8$,
—CO$_2$(CR$^9$R$^{10}$)CONR$^7$R$^8$,
—OC(O)R$^7$,
—CN,
—C(O)NR$^7$R$^8$,
—NR$^7$C(O)R$^8$,
—OC(O)NR$^7$R$^8$,
—NR$^7$C(O)OR$^8$,
—NR$^7$C(O)NR$^7$R$^8$,
—CR$^7$(N—OR$^8$),
—CHF$_2$,
—OCHF$_2$, and
—OCF$_3$;
each R$^{6b}$ is independently selected from:
R$^{6a}$,
aryl,
aryl-C$_{1-4}$ alkyl,
heteroaryl, and
heteroaryl-C$_{1-4}$ alkyl;
each R$^7$ and each R$^8$ are independently selected from:
hydrogen,
C$_{1-10}$ alkyl,
C$_{2-10}$ alkenyl,
C$_{2-10}$ alkynyl,
cycloalkyl,
cycloalkyl-C$_{1-10}$ alkyl;
heterocyclyl,
heterocyclyl-C$_{1-10}$ alkyl,
aryl,
heteroaryl,
aryl-C$_{1-10}$ alkyl, and
heteroaryl-C$_{1-10}$ alkyl;
wherein alkyl, alkenyl, alkynyl, cycloalkyl, and heterocyclyl are each unsubstituted or substituted with at least one substituent, such as one, two, three, or four substituents, independently selected from R$^{6a}$, and aryl and heteroaryl are each unsubstituted or substituted with at least one substituent, such as one, two, three, or four substituents, independently selected from R$^{6b}$; or
R$^7$ and R$^8$ together with the atom(s) to which they are attached form a heterocyclic ring of 4 to 7 members containing 0, 1, or 2 additional heteroatoms independently selected from oxygen, sulfur and NR$^{11}$,
each R$^7$ and R$^8$ may be unsubstituted or substituted on a carbon or nitrogen atom with at least one substituent, such as one, two, or three substituents, selected from R$^{12}$;
each R$^9$ and each R$^{10}$ are independently selected from:
hydrogen,
C$_{1-10}$ alkyl,
C$_{2-10}$ alkenyl,
C$_{2-10}$ alkynyl,
cycloalkyl,
cycloalkyl-C$_{1-10}$ alkyl,
heterocyclyl,
heterocyclyl-C$_{1-10}$ alkyl,
aryl,
heteroaryl,
aryl-C$_{1-10}$ alkyl, and
heteroaryl-C$_{1-10}$ alkyl; or
R$^9$ and R$^{10}$ together with the carbon atom(s) to which they are attached form a ring of 3 to 7 members containing 0, 1, or 2 heteroatoms independently selected from oxygen, sulfur and nitrogen;
each R$^{11}$ is independently selected from:
hydrogen,
C$_{1-10}$ alkyl,
C$_{3-10}$ cycloalkyl,
C$_{3-10}$ cycloalkyl-C$_{1-4}$ alkyl,
heterocyclyl,
heterocyclyl-C$_{1-4}$ alkyl,
aryl,
aryl-C$_{1-4}$ alkyl,
heteroaryl,
heteroaryl-C$_{1-4}$ alkyl,
—S(O)$_r$R$^7$,
—C(O)R$^7$,
—CO$_2$R$^7$,
—CO$_2$(CR$^9$R$^{10}$)$_t$CONR$^7$R$^8$, and
—C(O)NR$^7$R$^8$;
each R$^{12}$ is independently selected from:
halogen,
C$_{1-10}$ alkyl, C$_{3-10}$ cycloalkyl,
C$_{3-10}$ cycloalkylalkyl,
heterocyclyl,
heterocyclylalkyl,
aryl,
aryl-C$_{1-4}$ alkyl,
heteroaryl,
heteroaryl-C$_{1-4}$ alkyl,
—OR$^7$,
—NR$^7$S(O)$_r$R$^8$,
—S(O)$_r$R$^7$,
—SR$^7$,
—S(O)$_2$OR$^7$,
—OS(O)$_2$R$^7$,
—S(O)$_r$NR$^7$R$^8$,
—NR$^7$R$^8$,
—O(CR$^9$R$^{10}$)$_t$NR$^7$R$^8$,
—C(O)R$^7$,
—CO$_2$R$^8$,
—CO$_2$(CR$^9$R$^{10}$)$_t$CONR$^7$R$^8$,
—OC(O)R$^7$,
—CN,
—C(O)NR$^7$R$^8$,
—NR$^7$C(O)R$^8$,
—OC(O)NR$^7$R$^8$,
—NR$^7$C(O)OR$^8$,
—NR$^7$C(O)NR$^7$R$^8$,
—CHF$_2$,
—CF$_3$,
—OCHF$_2$, and
—OCF$_3$;

each m is independently selected from 0, 1 and 2;
each n is independently selected from 1, 2, and 3;
each p is independently selected from 0, 1, 2, and 3;
each q is independently selected from 0, 1, 2, and 3;
each r is independently selected from 1 and 2;
each t is independently selected from 1, 2, and 3.

In yet another aspect, the present disclosure provides pharmaceutical compositions comprising at least one compound of formula (I) and/or at least one pharmaceutically acceptable salt thereof and a pharmaceutically acceptable excipient.

In yet another aspect, the disclosure provides methods for modulating ALK, comprising administering to a system or a subject in need thereof, a therapeutically effective amount of at least one compound of formula (I) and/or at least one pharmaceutically acceptable salt thereof or pharmaceutical compositions thereof, thereby modulating said ALK. The disclosure also provides methods to treat, ameliorate or prevent a condition which responds to inhibition of ALK comprising administering to a system or subject in need of such treatment an effective amount of at least one compound of formula (I) and/or at least one pharmaceutically acceptable salt thereof or pharmaceutical compositions thereof, and optionally in combination with a second therapeutic agent, thereby treating said condition. Alternatively, the present disclosure provides the use of at least one compound of formula (I) and/or at least one pharmaceutically acceptable salt thereof in the manufacture of a medicament for treating a condition mediated by ALK. In particular embodiments, the compounds of the disclosure may be used alone or in combination with a second therapeutic agent to treat a condition mediated by ALK, wherein said condition is an autoimmune disease, a transplantation disease, an infectious disease or a cell proliferative disorder.

Furthermore, the disclosure provides methods for treating a cell proliferative disorder, comprising administering to a system or subject in need of such treatment an effective amount of at least one compound of formula (I) and/or at least one pharmaceutically acceptable salt thereof or pharmaceutical compositions thereof, and optionally in combination with a second therapeutic agent, thereby treating said condition.

Alternatively, the present disclosure provides the use of at least one compound of formula (I) and/or at least one pharmaceutically acceptable salt thereof in the manufacture of a medicament for treating a cell-proliferative disorder. In particular examples, the compounds of the disclosure may be used alone or in combination with a chemotherapeutic agent to treat a cell proliferative disorder, including but not limited to, lymphoma, osteosarcoma, melanoma, or a tumor of breast, renal, prostate, colorectal, thyroid, ovarian, pancreatic, neuronal, lung, uterine or gastrointestinal tumor.

In the above methods for using the compounds of the disclosure, at least one compound of formula (I) and/or at least one pharmaceutically acceptable salt thereof may be administered to a system comprising cells or tissues, or to a mammalian subject such as a human or animal subject.

BRIEF DESCRIPTION OF THE DRAWING

FIG. 1. Effect of a compound disclosed herein on relative tumor volume.

As used herein the following definitions are applicable.

The term "alkyl" refers to both branched and straight-chain saturated aliphatic hydrocarbon groups having the specified number of carbon atoms. Unless otherwise specified, "alkyl" refers to C$_1$-C$_{10}$ alkyl. For example, C$_1$-C$_{10}$, as in "C$_{1-10}$ alkyl" is defined to include groups having 1, 2, 3, 4, 5, 6, 7, 8, 9 or 10 carbons in a linear or branched arrangement. For example, "C$_{1-10}$ alkyl" includes but is not limited to methyl, ethyl, n-propyl, i-propyl, n-butyl, t-butyl, i-butyl, pentyl, hexyl, heptyl, octyl, nonyl, and decyl.

The term "cycloalkyl" means a saturated aliphatic cyclic hydrocarbon group having the specified number of carbon atoms. Unless otherwise specified, "cycloalkyl" refers to C$_{3-10}$ cycloalkyl. For example, "cycloalkyl" includes but is not limited to cyclopropyl, methyl-cyclopropyl, 2,2-dimethyl-cyclobutyl, 2-ethyl-cyclopentyl, and cyclohexyl.

The term "alkenyl" refers to a non-aromatic hydrocarbon radical, straight, branched or cyclic, containing from 2 to 10 carbon atoms and at least one carbon to carbon double bond. In some embodiments, one carbon to carbon double bond is present, and up to four non-aromatic carbon-carbon double bonds may be present. Thus, "C$_{2-10}$ alkenyl" means an alkenyl radical having from 2 to 10 carbon atoms. Alkenyl groups include but are not limited to ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. In some embodiments, up to three carbon-carbon triple bonds may be present. Thus, "C$_{2-10}$ alkynyl" means an alkynyl radical having from 2 to 10 carbon atoms. Alkynyl groups include but are not limited to ethynyl, propynyl, butynyl, and 3-methylbutynyl. The straight, branched or cyclic portion of the alkynyl group may contain triple bonds and may be substituted if a substituted alkynyl group is indicated.

The term "alkoxy" refers to either a cyclic or non-cyclic alkyl group of indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, cyclopropanyloxy, and cyclobutyloxy. "Alkoxy" therefore encompasses the definitions of alkyl and cycloalkyl above.

The term "aryl" encompasses: 5- and 6-membered carbocyclic aromatic rings, for example, benzene; bicyclic ring systems wherein at least one ring is carbocyclic and aromatic, for example, naphthalene, indane, and 1,2,3,4-tetrahydroquinoline; and tricyclic ring systems wherein at least one ring is carbocyclic and aromatic, for example, fluorene. In cases where the aryl substituent is bicyclic or tricyclic and at least one ring is non-aromatic, it is understood that attachment is via the aromatic ring.

For example, aryl includes 5- and 6-membered carbocyclic aromatic rings fused to a 5- to 7-membered heterocyclic ring containing one or more heteroatoms selected from N, O, and S, provided that the point of attachment is at the carbocyclic aromatic ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings are fused with a heterocyclic aromatic ring, the resulting ring system is heteroaryl, not aryl, as defined herein.

The term "halogen" (or "halo") refers to fluorine, chlorine, bromine and iodine.

The term "heteroaryl" refers to 5- to 8-membered aromatic, monocyclic rings containing one or more, for example, from 1 to 4, or, in some embodiments, from 1 to 3, heteroatoms selected from N, O, and S, with the remaining ring atoms being carbon;

8- to 12-membered bicyclic rings containing one or more, for example, from 1 to 4, or, in some embodiments, from 1 to 3, heteroatoms selected from N, O, and S, with the remaining ring atoms being carbon and wherein at least one heteroatom is present in an aromatic ring; and 11- to 14-membered tricyclic rings containing one or more, for example, from 1 to 4, or, in some embodiments, from 1 to 3, heteroatoms selected from N, O, and S, with the remaining ring atoms being carbon and wherein at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the heteroaryl group is not more than 1.

Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 1-pyrazolyl, 2,3-pyrazolyl, 2,4-imidazolinyl, isoxazolyl, oxazolyl, thiazolyl, thiadiazolyl, tetrazolyl, thienyl, benzothienyl, furyl, benzofuryl, benzoimidazolinyl, indolinyl, pyridizinyl, triazolyl, quinolinyl, pyrazolyl, and 5,6,7,8-tetrahydroisoquinoline.

Further heteroaryl groups include but are not limited to pyrrolyl, isothiazolyl, triazinyl, pyrazinyl, pyridazinyl, indolyl, benzotriazolyl, quinoxalinyl, and isoquinolinyl. As with the definition of heterocycle below, "heteroaryl" is also understood to include the N-oxide derivative of any nitrogen-containing heteroaryl.

Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

In cases where the heteroaryl substituent is bicyclic or tricyclic and at least one ring is non-aromatic or contains no heteroatoms, it is understood that attachment is via the aromatic ring or via the heteroatom containing ring, respectively.

The term "heterocycle" (and variations thereof such as "heterocyclic", or "heterocyclyl") broadly refers to a single aliphatic ring, usually with 3 to 7 ring atoms, containing at least 2 carbon atoms in addition to 1-3 heteroatoms independently selected from oxygen, sulfur, and nitrogen, as well as combinations comprising at least one of the foregoing heteroatoms. "Heterocycle" also refers to 5- to 7-membered heterocyclic ring containing one or more heteroatoms selected from N, O, and S fused with 5- and 6-membered carbocyclic aromatic ring, provided that the point of attachment is at the heterocyclic ring. The rings may be saturated or have one or more double bonds (i.e. partially unsaturated). The heterocycle can be substituted by oxo. The point of the attachment may be carbon or heteroatom in the heterocyclic ring, provided that attachment results in the creation of a stable structure. When the heterocyclic ring has substituents, it is understood that the substituents may be attached to any atom in the ring, whether a heteroatom or a carbon atom, provided that a stable chemical structure results. Heterocycle does not overlap with heteroaryl.

Suitable heterocycles include, for example (as numbered from the linkage position assigned priority 1), 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 1-piperazinyl, 2-piperazinyl, and 2,5-piperazinyl. Morpholinyl groups are also contemplated, including 2-morpholinyl and 3-morpholinyl (numbered wherein the oxygen is assigned priority 1). Substituted heterocycle also includes ring systems substituted with one or more oxo moieties, such as piperidinyl N-oxide, morpholinyl-N-oxide, 1-oxo-1-thiomorpholinyl and 1,1-dioxo-1-thiomorpholinyl.

As used herein, "arylalkyl" refers to an alkyl moiety substituted by an aryl group. Example arylalkyl groups include benzyl, phenethyl, and naphthylmethyl groups. In some embodiments, arylalkyl groups have from 7 to 20 or 7 to 11 carbon atoms. When used in the phrase "aryl-$C_{1-4}$ alkyl", the term "$C_{1-4}$" refers to the alkyl portion of the moiety and does not describe the number of atoms in the aryl portion of the moiety. Likewise, when used in the phrase "aryl-$C_{1-10}$ alkyl", the term "$C_{1-10}$" refers to the alkyl portion of the moiety and does not describe the number of atoms in the aryl portion of the moiety.

As used herein, "heterocyclylalkyl" refers to alkyl substituted by heterocyclyl. When used in the phrase "heterocyclyl-$C_{1-10}$ alkyl", the term "$C_{1-10}$" refers to the alkyl portion of the moiety and does not describe the number of atoms in the heterocyclyl portion of the moiety.

As used herein, "cycloalkylalkyl" refers to alkyl substituted by cycloalkyl. When used in the phrase "$C_{3-10}$ cycloalkylalkyl", the term "$C_{3-10}$" refers to the cycloalkyl portion of the moiety and does not describe the number of atoms in the alkyl portion of the moiety. When used in the phrase "$C_{3-7}$ cycloalkylalkyl", the term "$C_{3-7}$" refers to the cycloalkyl portion of the moiety and does not describe the number of atoms in the alkyl portion of the moiety. When used in the phrase "$C_{3-8}$ cycloalkylalkyl", the term "$C_{3-8}$"

refers to the cycloalkyl portion of the moiety and does not describe the number of atoms in the alkyl portion of the moiety. When used in the phrase "cycloalkyl-$C_{1-10}$ alkyl", the term "$C_{1-10}$" refers to the alkyl portion of the moiety and does not describe the number of atoms in the cycloalkyl portion of the moiety.

As used herein, "heteroarylalkyl" refers to alkyl substituted by heteroaryl. When used in the phrase "heteroaryl-$C_{1-4}$ alkyl", the term "$C_{1-4}$" refers to the alkyl portion of the moiety and does not describe the number of atoms in the heteroaryl portion of the moiety. Likewise, when used in the phrase "heteroaryl-$C_{1-10}$ alkyl", the term "$C_{1-10}$" refers to the alkyl portion of the moiety and does not describe the number of atoms in the heteroaryl portion of the moiety.

For avoidance of doubt, reference, for example, to substitution of alkyl, cycloalkyl, heterocyclyl, aryl, and/or heteroaryl refers to substitution of each of those groups individually as well as to substitutions of combinations of those groups. That is, if $R^1$ is arylalkyl, the aryl portion may be unsubstituted or substituted with at least one substituent, such as one, two, three, or four substituents, independently selected from $R^{6b}$ and the alkyl portion may also be unsubstituted or substituted with at least one substituent, such as one, two, three, or four substituents, independently selected from $R^{6a}$.

The term "pharmaceutically acceptable salts" refers to salts prepared from pharmaceutically acceptable non-toxic bases or acids including inorganic or organic bases and inorganic or organic acids. Salts derived from inorganic bases may be selected, for example, from aluminum, ammonium, calcium, copper, ferric, ferrous, lithium, magnesium, manganic, manganous, potassium, sodium, and zinc salts. Further, for example, the pharmaceutically acceptable salts derived from inorganic bases may be selected from ammonium, calcium, magnesium, potassium, and sodium salts. Salts in the solid form may exist in one or more crystal structures, and may also be in the form of hydrates. Salts derived from pharmaceutically acceptable organic non-toxic bases may be selected, for example, from salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, and tripropylamine, tromethamine.

When the compound disclosed herein is basic, salts may be prepared using at least one pharmaceutically acceptable non-toxic acid, selected from inorganic and organic acids. Such acid may be selected, for example, from acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p-toluenesulfonic acids. In some embodiments, such acid may be selected, for example, from citric, hydrobromic, hydrochloric, maleic, phosphoric, sulfuric, fumaric, and tartaric acids.

The terms "co-administration" or "combined administration" or the like as used herein are meant to encompass administration of the selected therapeutic agents to a single patient, and are intended to include treatment regimens in which the agents are not necessarily administered by the same route of administration or at the same time.

The term "pharmaceutical combination" as used herein refers to a product obtained from mixing or combining active ingredients, and includes both fixed and non-fixed combinations of the active ingredients.

The term "fixed combination" means that the active ingredients, e.g. a compound of Formula (I) and a co-agent, are both administered to a patient simultaneously in the form of a single entity or dosage.

The term "non-fixed combination" means that the active ingredients, e.g. a compound of Formula (I) and a co-agent, are both administered to a patient as separate entities either simultaneously, concurrently or sequentially with no specific time limits, wherein such administration provides therapeutically effective levels of the active ingredients in the body of the patient. The latter also applies to cocktail therapy, e.g. the administration of three or more active ingredients.

The term "therapeutically effective amount" means the amount of the subject compound that will elicit a biological or medical response in a cell, tissue, organ, system, animal or human that is being sought by the researcher, veterinarian, medical doctor or other clinician.

The term "administration" or "administering" of the subject compound means providing a compound of the disclosure and prodrugs thereof to a subject in need of treatment.

The term "composition" as used herein is intended to encompass a product comprising the specified ingredients in the specified amounts, as well as any product which results, directly or indirectly, from combination of the specified ingredients in the specified amounts. Such term in relation to a pharmaceutical composition is intended to encompass a product comprising the active ingredient (s), and the inert ingredient (s) that make up the carrier, as well as any product which results, directly or indirectly, from combination, complexation or aggregation of any two or more of the ingredients, or from dissociation of one or more of the ingredients, or from other types of reactions or interactions of one or more of the ingredients.

By "pharmaceutically acceptable" it is meant compatible with the other ingredients of the formulation and not unacceptably deleterious to the recipient thereof.

The term "protecting group" or "Pg" refers to a substituent that can be commonly employed to block or protect certain functionality while reacting other functional groups on the compound. For example, an "amino-protecting group" is a substituent attached to an amino group that blocks or protects the amino functionality in the compound. Suitable amino-protecting groups include but are not limited to acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include but are not limited to acetyl and silyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

In one embodiment, disclosed herein is at least one compound of formula (I):

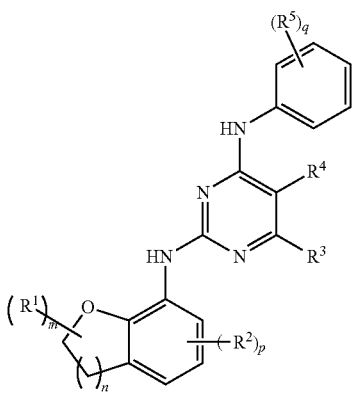

(I)

and/or at least one pharmaceutically acceptable salt thereof, wherein
each $R^1$ is independently selected from:
hydrogen,
halogen,
hydroxyl,
$C_{1-10}$ alkyl,
$C_{3-10}$ cycloalkyl,
$C_{3-10}$ cycloalkyl-alkyl,
heterocyclyl,
heterocyclylalkyl
aryl,
arylalkyl,
heteroaryl, and
heteroarylalkyl,
wherein alkyl, cycloalkyl, and heterocyclyl are each unsubstituted or substituted with at least one substituent, such as one, two, three, or four substituents, independently selected from $R^{6a}$, and wherein aryl and heteroaryl are each unsubstituted or substituted with at least one substituent, such as one, two, three, or four substituents, independently selected from $R^{6b}$;
each $R^2$ is independently selected from:
hydrogen,
halogen,
hydroxyl,
$C_{1-10}$ alkyl,
$C_{2-10}$ alkenyl,
$C_{2-10}$ alkynyl,
$C_{3-10}$ cycloalkyl,
$C_{3-10}$ cycloalkylalkyl,
heterocyclyl,
heterocyclylalkyl
heterocyclylcarbonyl,
aryl,
heteroaryl,
arylalkyl, and
heteroarylalkyl,
wherein alkyl, alkenyl, alkynyl, cycloalkyl, and heterocyclyl are each unsubstituted or substituted with at least one substituent, such as one, two, three, or four substituents, independently selected from $R^{6a}$, and each aryl and heteroaryl is unsubstituted or substituted with at least one substituent, such as one, two, three, or four substituents, independently selected from $R^{6b}$;
each $R^3$ is independently selected from:
hydrogen,
halogen,
—CN,
—NR$^7$R$^8$, and
$C_{1-10}$ alkyl;
wherein alkyl is unsubstituted or substituted with at least one substituent, such as one, two, three, or four substituents, independently selected from $R^{6a}$;
each $R_4$ is independently selected from:
hydrogen,
halogen,
—CN,
$C_{1-10}$ alkyl,
$C_{2-10}$ alkenyl,
$C_{2-10}$ alkynyl, and
$C_{3-10}$ cycloalkyl;
wherein $C_{1-10}$ alkyl, $C_{2-10}$ alkenyl, $C_{2-10}$ alkynyl, and $C_{3-10}$ cycloalkyl are each unsubstituted or substituted with at least one substituent, such as one, two, three, or four substituents, independently selected from $R^{6a}$;
or $R^3$ and $R^4$ together with the carbon atoms to which they are attached form a 5-6 membered ring containing 0, 1, 2 or 3 heteroatoms independently selected from oxygen, sulfur and nitrogen, and optionally substituted with 1-2 $R^{6b}$ groups;
each $R^5$ is independently selected from:
hydrogen,
$C_{1-10}$ alkyl,
$C_{2-10}$ alkenyl,
$C_{2-10}$ alkynyl,
$C_{3-10}$ cycloalkyl,
—OR$^8$,
—NR$^7$S(O)$_r$R$^8$,
—NO$_2$,
halogen,
—S(O)$_r$R$^7$,
—SR$^8$,
—S(O)$_2$OR$^7$,
—OS(O)$_2$R$^8$,
—S(O)$_r$NR$^7$R$^8$,
—NR$^7$R$^8$,
—O(CR$^9$R$^{10}$)$_t$NR$^7$R$^8$,
—C(O)R$^7$,
—CO$_2$R$^8$,
—CO$_2$(CR$^9$R$^{10}$)$_t$CONR$^7$R$^8$,
—OC(O)R$^7$,
—CN,
—C(O)NR$^7$R$^8$,
—NR$^7$C(O)R$^8$,
—OC(O)NR$^7$R$^8$,
—NR$^7$C(O)OR$^8$,
—NR$^7$C(O)NR$^7$R$^8$,
—CR$^7$(N—OR$^8$),
—CHF$_2$,
—CF$_3$,
—OCHF$_2$, and
—OCF$_3$;
wherein $C_{1-10}$ alkyl, $C_{2-10}$ alkenyl, $C_{2-10}$ alkynyl, and $C_{3-10}$ cycloalkyl are each unsubstituted or substituted with at least one substituent, such as one, two, three, or four substituents, independently selected from $R^{6a}$;
each $R^{6a}$ is independently selected from:
$C_{1-10}$ alkyl,
$C_{2-10}$ alkenyl,
$C_{2-10}$ alkynyl,
$C_{3-10}$ cycloalkyl,
—OR$^8$,
—NR$^7$S(O)$_r$R$^8$,
—NO$_2$,
halogen,
—S(O)$_r$R$^7$, —$SR^8$,
—$S(O)_2OR^7$,
—$OS(O)_2R^8$,
—$S(O)_rNR^7R^8$,
—$NR^7R^8$,
—$(CR^9R^{10})_tOR^8$,
—$(CR^9R^{10})_tNR^7R^8$,
—$(CR^9R^{10})_tSR^8$,
—$(CR^9R^{10})_tS(O)_rR^8$,
—$(CR^9R^{10})_tCO_2R^8$,
—$(CR^9R^{10})_tCONR^7R^8$,
—$(CR^9R^{10})_tNR^7CO_2R^8$,
—$(CR^9R^{10})_tOCONR^7R^8$,
—$(CR^9R^{10})_tNR^7CONR^7R^8$,
—$(CR^9R^{10})_tNR^7SO_2NR^7R^8$,
—$O(CR^9R^{10})_tNR^7R^8$,
—$C(O)R^7$,
—$C(O)(CR^9R^{10})_tOR^8$,
—$C(O)(CR^9R^{10})_tNR^7R^8$,
—$C(O)(CR^9R^{10})_tSR^8$,
—$C(O)(CR^9R^{10})_tS(O)_rR^8$,
—$CO_2R^8$,
—$CO_2(CR^9R^{10})_tCONR^7R^8$,
—$OC(O)R^7$,
—CN,
—$C(O)NR^7R^8$,
—$NR^7C(O)R^8$,
—$OC(O)NR^7R^8$,
—$NR^7C(O)OR^8$,
—$NR^7C(O)NR^7R^8$,
—$CR^7(N—OR^8)$,
—$CHF_2$,
—$CF_3$,
—$OCHF_2$, and
—$OCF_3$;
each $R^{6b}$ is independently selected from:
$R^{6a}$,
aryl,
aryl-$C_{1-4}$ alkyl,
heteroaryl, and
heteroaryl$C_{1-4}$ alkyl;
each $R^7$ and each $R^8$ are independently selected from:
hydrogen,
$C_{1-10}$ alkyl,
$C_{2-10}$ alkenyl,
$C_{2-10}$ alkynyl,
cycloalkyl,
cycloalkyl-$C_{1-10}$ alkyl;
heterocyclyl,
heterocyclyl-$C_{1-10}$ alkyl,
aryl,
heteroaryl,
aryl-$C_{1-10}$ alkyl, and
heteroaryl-$C_{1-10}$ alkyl;
wherein alkyl, alkenyl, alkynyl, cycloalkyl, and heterocyclyl are each unsubstituted or substituted with at least one substituent, such as one, two, three, or four substituents, independently selected from $R^{6a}$, and aryl and heteroaryl are each unsubstituted or substituted with at least one substituent, such as one, two, three, or four substituents, independently selected from $R^{6b}$; or
$R^7$ and $R^8$ together with the atom(s) to which they are attached form a heterocyclic ring of 4 to 7 members containing 0, 1, or 2 additional heteroatoms independently selected from oxygen, sulfur and $NR^{11}$, each $R^7$ and $R^8$ may be unsubstituted or substituted on a carbon or nitrogen atom with at least one substituent, such as one, two, or three substituents, selected from $R^{12}$;
each $R^9$ and each $R^{10}$ are independently selected from:
hydrogen,
$C_{1-10}$ alkyl,
$C_{2-10}$ alkenyl,
$C_{2-10}$ alkynyl,
cycloalkyl,
cycloalkyl-$C_{1-10}$ alkyl,
heterocyclyl,
heterocyclyl-$C_{1-10}$ alkyl,
aryl,
heteroaryl,
aryl-$C_{1-10}$ alkyl, and
heteroaryl-$C_{1-10}$ alkyl; or
$R^9$ and $R^{10}$ together with the carbon to which they are attached form a ring of 3 to 7 members containing 0, 1, or 2 heteroatoms independently selected from oxygen, sulfur and nitrogen;
each $R^{11}$ is independently selected from:
hydrogen,
$C_{1-10}$ alkyl,
$C_{3-10}$ cycloalkyl,
$C_{3-10}$ cycloalkyl-$C_{1-4}$ alkyl,
heterocyclyl,
heterocyclyl-$C_{1-4}$ alkyl,
aryl,
aryl-$C_{1-4}$ alkyl,
heteroaryl,
heteroaryl-$C_{1-4}$ alkyl,
—$S(O)_rR^7$,
—$C(O)R^7$,
—$CO_2R^7$,
—$CO_2(CR^9R^{10})_tCONR^7R^8$, and
—$C(O)NR^7R^8$;
each $R^{12}$ is independently selected from:
halogen,
$C_{1-10}$ alkyl,
$C_{3-10}$ cycloalkyl,
$C_{3-10}$ cycloalkylalkyl,
heterocyclyl,
heterocyclylalkyl,
aryl,
aryl-$C_{1-4}$ alkyl,
heteroaryl,
heteroaryl-$C_{1-4}$ alkyl,
—$OR^7$,
—$NR^7S(O)_rR^8$,
—$S(O)_rR^7$,
—$SR^7$,
—$S(O)_2OR^7$,
—$OS(O)_2R^7$,
—$S(O)_rNR^7R^8$,
—$NR^7R^8$,
—$O(CR^9R^{10})_tNR^7R^8$,
—$C(O)R^7$,
—$CO_2R^8$,
—$CO_2(CR^9R^{10})_tCONR^7R^8$,
—$OC(O)R^7$,
—CN,
—$C(O)NR^7R^8$,
—$NR^7C(O)R^8$,
—$OC(O)NR^7R^8$,
—$NR^7C(O)OR^8$,
—$NR^7C(O)NR^7R^8$,
—$CHF_2$, —CF$_3$,
—OCHF$_2$, and
—OCF$_3$;
each m is independently selected from 0, 1 and 2;
each n is independently selected from 1, 2, and 3;
each p is independently selected from 0, 1, 2, and 3;
each q is independently selected from 0, 1, 2, and 3;
each r is independently selected from 1 and 2;
each t is independently selected from 1, 2, and 3.

In some embodiments, each $R^1$ is independently selected from hydrogen and $C_{1-10}$ alkyl, wherein alkyl is unsubstituted or substituted with at least one substituent, such as one, two, three, or four substituents, independently selected from hydroxyl and $C_{1-10}$ alkoxy.

In some embodiments, $R^1$ is hydrogen.

In some embodiments, each $R^1$ is independently selected from $C_{1-10}$ alkyl, wherein alkyl is unsubstituted or substituted with at least one substituent, such as one, two, three, or four substituents, independently selected from hydroxyl and $C_{1-10}$ alkoxy.

In some embodiments, $R^1$ is methyl, hydroxymethyl, or methoxymethyl.

In some embodiments, each $R^2$ is independently selected from $C_{1-10}$ alkyl, heterocyclylcarbonyl, and heterocyclyl, wherein alkyl and heterocyclyl are independently unsubstituted or substituted with at least one substituent, such as one, two, three, or four substituents, independently selected from $R^{6a}$, $R^{6a}$ is as described above.

In some embodiments, each $R^2$ is independently selected from $C_{1-10}$ alkyl and piperidinyl which are unsubstituted or substituted with at least one substituent, such as one, two, three, or four substituents, independently selected from $R^{6a}$, $R^{6a}$ is as described above.

In some embodiments, each $R^2$ is independently selected from methyl and 4-piperidinyl which are unsubstituted or substituted with at least one substituent, such as one, two, three, or four substituents, independently selected from $R^{6a}$, $R^{6a}$ is as described above.

In some embodiments, each $R^2$ is independently selected from methyl and 4-piperidinyl, wherein 4-piperidinyl is unsubstituted or substituted with at least one substituent, such as one, two, three, or four substituents, independently selected from $R^6$, wherein $R^6$ is independently selected from $C_{1-10}$ alkyl, —C(O)$R^7$, —S(O)$_r R^7$, —(CR$^9$R$^{10}$)$CO_2 R^8$, —C(O)CR$^9$R$^{10}$)$_t$NR$^7$R$^8$, —(CR$^9$R$^{10}$)$_t$OR$^8$, —(CR$^9$R$^{10}$)$_t$CONR$^7$R$^8$, —(CR$^9$R$^{10}$)$_t$S(O)$_r R^8$, —(CR$^9$R$^{10}$)$_t$OR$^8$, $R^7$, $R^8$, $R^9$, $R^{10}$, t and r are as described above.

In some embodiments, $R^3$ is hydrogen.

In some embodiments, each $R^4$ is independently selected from hydrogen, $C_{1-10}$alkyl, and halogen.

In some embodiments, each $R^4$ is independently selected from halogen.

In some embodiments, $R^4$ is chlorine.

In some embodiments, $R^3$ and $R^4$ together with the carbon atoms to which they are attached form a 5-membered ring containing 2 nitrogen atoms, wherein the 5-membered ring is optionally substituted with 1 or 2 $C_{1-10}$ alkyl.

In some embodiments, $R^3$ and $R^4$ together with the carbon atoms to which they are attached form pyrazolo.

In some embodiments, $R^5$ is —S(O)$_r R^7$, $R^7$ and r are as described above.

In some embodiments, $R^5$ is —S(O)$_2 R^7$, wherein $R^7$ is selected from $C_{10}$ alkyl.

In some embodiments, $R^5$ is —S(O)$_2 R^7$, wherein $R^7$ is isopropyl.

In some embodiments, n is 1.
In some embodiments, p is 2.
In some embodiments, m is 1.
In some embodiments, q is 1.

Also provided is at least one compound, selected from:
N-4-(2-(isopropylsulfonyl)phenyl)-3-methyl-N-6-(5-methyl-4-(piperidin-4-yl)-2,3-dihydrobenzofuran-7-yl)-1H-pyrazolo[3,4-d]pyrimidine-4,6-diamine;
N-4-(2-(isopropylsulfonyl)phenyl)-3-methyl-N-6-(5-methyl-4-(1-methylpiperidin-4-yl)-2,3-dihydrobenzofuran-7-yl)-1H-pyrazolo[3,4-d]pyrimidine-4,6-diamine;
(R)—N-6-(2,5-dimethyl-4-(piperidin-4-yl)-2,3-dihydrobenzofuran-7-yl)-N-4-(2-(isopropylsulfonyl)phenyl)-3-methyl-1H-pyrazolo[3,4-d]pyrimidine-4,6-diamine;
(R)—N-6-(2,5-dimethyl-4-(1-methylpiperidin-4-yl)-2,3-dihydrobenzofuran-7-yl)-N-4-(2-(isopropylsulfonyl)phenyl)-3-methyl-1H-pyrazolo[3,4-d]pyrimidine-4,6-diamine;
(S)—N-6-(2,5-dimethyl-4-(piperidin-4-yl)-2,3-dihydrobenzofuran-7-yl)-N-4-(2-(isopropylsulfonyl)phenyl)-3-methyl-1H-pyrazolo[3,4-d]pyrimidine-4,6-diamine;
(S)—N-6-(2,5-dimethyl-4-(1-methylpiperidin-4-yl)-2,3-dihydrobenzofuran-7-yl)-N-4-(2-(isopropylsulfonyl)phenyl)-3-methyl-1H-pyrazolo[3,4-d]pyrimidine-4,6-diamine;
(7-(4-(2-(isopropylsulfonyl)phenylamino)-3-methyl-1H-pyrazolo[3,4-d]pyrimidin-6-ylamino)-5-methyl-4-(piperidin-4-yl)-2,3-dihydrobenzofuran-2-yl)methanol;
N-4-(2-(isopropylsulfonyl)phenyl)-N-6-(2-(methoxymethyl)-5-methyl-4-(piperidin-4-yl)-2,3-dihydrobenzofuran-7-yl)-3-methyl-1H-pyrazolo[3,4-d]pyrimidine-4,6-diamine;
(R)-5-chloro-N-2-(2,5-dimethyl-4-(piperidin-4-yl)-2,3-dihydrobenzofuran-7-yl)-N-4-(2-(isopropylsulfonyl)phenyl)pyrimidine-2,4-diamine;
(R)-5-chloro-N-2-(2,5-dimethyl-4-(1-methylpiperidin-4-yl)-2,3-dihydrobenzofuran-7-yl)-N-4-(2-(isopropylsulfonyl)phenyl)pyrimidine-2,4-diamine;
(S)-5-chloro-N-2-(2,5-dimethyl-4-(piperidin-4-yl)-2,3-dihydrobenzofuran-7-yl)-N-4-(2-(isopropylsulfonyl)phenyl)pyrimidine-2,4-diamine;
(S)-5-chloro-N-2-(2,5-dimethyl-4-(1-methylpiperidin-4-yl)-2,3-dihydrobenzofuran-7-yl)-N-4-(2-(isopropylsulfonyl)phenyl)pyrimidine-2,4-diamine;
5-chloro-N-4-(2-(isopropylsulfonyl)phenyl)-N-2-(5-methyl-4-(piperidin-4-yl)-2,3-dihydrobenzofuran-7-yl)pyrimidine-2,4-diamine;
5-chloro-N-4-(2-(isopropylsulfonyl)phenyl)-N-2-(5-methyl-4-(1-methylpiperidin-4-yl)-2,3-dihydrobenzofuran-7-yl)pyrimidine-2,4-diamine;
(S)-1-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)ethanone;
(R)-1-(4(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)ethanone;
(S)-5-chloro-N-2-(2,5-dimethyl-4-(1-(methylsulfonyl)piperidin-4-yl)-2,3-dihydrobenzofuran-7-yl)-N-4-(2-(isopropylsulfonyl)phenyl)pyrimidine-2,4-diamine;
(R)-5-chloro-N-2-(2,5-dimethyl-4-(1-(methylsulfonyl)piperidin-4-yl)-2,3-dihydrobenzofuran-7-yl)-N-4-(2-(isopropylsulfonyl)phenyl)pyrimidine-2,4-diamine;
(S)-2-(4(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)acetic acid;
(R)-2-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)acetic acid;

(S)-2-amino-1-(4((S)-7-((5-chloro-4-((2-(isopropylsulfonyl)phenyl)amino)pyrimidin-2-yl)amino)-2,5-dimethyl-2,3-dihydrobenzofuran-4-yl)piperidin-yl)propan-1-one;

(S)-2-amino-1-(4-((R)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)propan-1-one;

(R)-1-(4-((R)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)propan-2-ol;

(S)-1-(4-((R)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)propan-2-ol;

(S)-2-(4(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)acetamide;

(R)-2-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)acetamide;

(S)-2-(4(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-N,N-dimethylacetamide;

(R)-2-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-N,N-dimethylacetamide;

(S)-5-chloro-N-2-(2,5-dimethyl-4-(1-(2-(methylsulfonyl)ethyl)piperidin-4-yl)-2,3-dihydrobenzofuran-7-yl)-N-4-(2-(isopropylsulfonyl)phenyl)pyrimidine-2,4-diamine;

(R)-5-chloro-N-2-(2,5-dimethyl-4-(1-(2-(methylsulfonyl)ethyl)piperidin-4-yl)-2,3-dihydrobenzofuran-7-yl)-N-4-(2-(isopropylsulfonyl)phenyl)pyrimidine-2,4-diamine;

(S)-5-chloro-N-4-(2-(isopropylsulfonyl)phenyl)-N-2-(4-(1-(2-methoxyethyl)piperidin-4-yl)-2,5-dimethyl-2,3-dihydrobenzofuran-7-yl)pyrimidine-2,4-diamine;

(R)-5-chloro-N-4-(2-(isopropylsulfonyl)phenyl)-N-2-(4-(1-(2-methoxyethyl)piperidin-4-yl)-2,5-dimethyl-2,3-dihydrobenzofuran-7-yl)pyridine-2,4-diamine;

(R)-2-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)ethanol;

(S)-2-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)ethanol;

(R)-1-(4-((S)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)propan-2-ol;

(S)-1-(4-((S)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)propan-2-ol;

(R)-1-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-2-hydroxyethanone;

(S)-1-(4-((R)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-2-hydroxypropan-1-one;

(R)-1-(4-((R)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-2-hydroxypropan-1-one;

(S)-methyl 4-(7-((5-chloro-4-((2-(isopropylsulfonyl)phenyl)amino)pyrimidin-2-yl)amino)-2,5-dimethyl-2,3-dihydrobenzofuran-4-yl)piperidine-1-carboxylate;

(S)-ethyl 2-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)acetate;

(S)-2-amino-1-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)ethanone;

(S)-4-(7-((5-chloro-4-((2-(isopropylsulfonyl)phenyl)amino)pyrimidin-2-yl)amino)-2,5-dimethyl-2,3-dihydrobenzofuran-4-yl)piperidine-1-carboxamide;

(S)-1-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-2-(methylamino)ethanone;

(S)-1-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-2-(dimethylamino)ethanone;

(S)-(7-((5-chloro-4-((2-(isopropylsulfonyl)phenyl)amino)pyrimidin-2-yl)amino)-2,5-dimethyl-2,3-dihydrobenzofuran-4-yl)(piperazin-1-yl)methanone;

(S)-(7-((5-chloro-4-((2-(isopropylsulfonyl)phenyl)amino)pyrimidin-2-yl)amino)-2,5-dimethyl-2,3-dihydrobenzofuran-4-yl)(4-methylpiperazin-yl)methanone;

(S)-(7-((5-chloro-4-((2-(isopropylsulfonyl)phenyl)amino)pyrimidin-2-yl)amino)-2,5-dimethyl-2,3-dihydrobenzofuran-4-yl)(morpholino)methanone;

(R)-1-(4-(7-((5-chloro-4-((2-(isopropylsulfonyl)phenyl)amino)pyrimidin-2-yl)amino)-2,5-dimethyl-2,3-dihydrobenzofuran-4yl)piperidin-1-yl)propan-1-one;

(R)-1-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-2-methylpropan-1-one;

(R)-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)(cyclopropyl)methanone;

(R)-5-chloro-N-2-(4-(1-(ethylsulfonyl)piperidin-4-yl)-2,5-dimethyl-2,3-dihydrobenzofuran-7-yl)-N-4-(2-(isopropylsulfonyl)phenyl)pyridine-2,4-diamine;

(R)-5-chloro-N-4-(2-(isopropylsulfonyl)phenyl)-N-2-(4-(1-(isopropylsulfonyl)piperidin-4-yl)-2,5-dimethyl-2,3-dihydrobenzofuran-7-yl)pyrimidine-2,4-diamine;

(R)-5-chloro-N-2-(4-(1-(cyclopropylsulfonyl)piperidin-4-yl)-2,5-dimethyl-2,3-dihydrobenzofuran-7-yl)-N-4-(2-(isopropylsulfonyl)phenyl)pyrimidine-2,4-diamine;

(R)-1-(4-((S)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-2-methoxypropan-1-one;

(R)-1-(4-((R)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-2-methoxypropan-1-one;

(S)-1-(4-((R)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-2-methoxypropan-1-one;

(S)-1-(4-((S)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-2-methoxypropan-1-one, and pharmaceutically acceptable salts thereof.

The compounds disclosed herein and their pharmaceutically acceptable salts exhibit valuable pharmacological properties when tested in vitro in cell-free kinase assays and in cellular assays, and are therefore useful as pharmaceuticals.

In one aspect, compounds of formula (I) may inhibit the tyrosine kinase activity of ALK and the fusion protein of NPM-ALK. This protein tyrosine kinase results from a gene fusion of nucleophosmin (NPM) and ALK, rendering the protein tyrosine kinase activity of ALK ligand independent. NPM-ALK plays a key role in signal transmission in a number of hematopoetic and other human cells leading to hematological and neoplastic diseases, for example in anaplastic large-cell lymphoma (ALCL) and non-Hodgkin's lymphomas (NHL), specifically in ALK+NHL or Alkomas, in inflammatory myofibroblastic tumors (IMT) and neuroblastomas. (Duyster et al. 2001 Oncogene 20, 5623-5637). In addition to NPM-ALK, other gene fusions have been identified in human hematological and neoplastic diseases; for example, TPM3-ALK (a fusion of nonmuscle tropomyosin with ALK).

The inhibition of ALK tyrosine kinase activity may be demonstrated using known methods, for example using the recombinant kinase domain of the ALK in analogy to the VEGF-R kinase assay described in J. Wood et al. Cancer Res. 60, 2178-2189 (2000). In general, in vitro enzyme assays using GST-ALK protein tyrosine kinase are performed in 96-well plates as a filter binding assay in 20 mM Tris HCl, pH=7.5, 3 mM $MgCl_2$, 10 mM $MnCl_2$, 1 mM DTT, 0.1 µCi/assay (=30 µl) [γ-33P]-ATP, 2 µM ATP, 3 µg/mL poly (Glu, Tyr 4:1) Poly-EY (Sigma P-0275), 1% DMSO, 25 ng ALK enzyme. Assays are incubated for 10 min at ambient temperature. Reactions are terminated by adding 50 µl of 125 mM EDTA, and the reaction mixture is transferred onto a MAIP Multiscreen plate (Millipore, Bedford, Mass., USA), previously wet with methanol, and rehydrated for 5 min with $H_2O$. Following washing (0.5% $H_3PO_4$), plates are counted in a liquid scintillation counter. $IC_{50}$ values are calculated by linear regression analysis of the percentage inhibition.

Compounds of formula (I) may potently inhibit the growth of human NPM-ALK overexpressing murine BaF3 cells (DSMZ Deutsche Sammiung von Mikroorganismen und Zellkulturen GmbH, Germany). The expression of NPM-ALK may be achieved by transfecting the BaF3 cell line with an expression vector pClneo™ (Promega Corp., Madison Wis., USA) coding for NPM-ALK and subsequent selection of G418 resistant cells. Non-transfected BaF3 cells depend on IL-3 for cell survival. In contrast, NPM-ALK expressing BaF3 cells (named BaF3-NPM-ALK hereinafter) can proliferate in the absence of IL-3 because they obtain proliferative signal through NPM-ALK kinase. Putative inhibitors of the NPM-ALK kinase therefore abolish the growth signal and may result in antiproliferative activity. The antiproliferative activity of putative inhibitors of the NPM-ALK kinase can however be overcome by addition of IL-3, which provides growth signals through an NPM-ALK independent mechanism. An analogous cell system using FLT3 kinase has also been described (see, E Weisberg et al. Cancer Cell; 1, 433-443 (2002)).

The inhibitory activity of the compounds of the invention may be determined as follows. In general, BaF3-NPM-ALK cells (15,000/microtitre plate well) are transferred to 96-well microtitre plates. Test compounds dissolved in dimethyl sulfoxide (DMSO) are added in a series of concentrations (dilution series) in such a manner that the final concentration of DMSO is not greater than 1% (v/v). After the addition, the plates are incubated for two days during which the control cultures without test compound are able to undergo two cell-division cycles. The growth of the BaF3-NPM-ALK cells is measured by means of YOPRO™ staining [T Idziorek et al. J. Immunol. Methods; 185: 249-258 (1995)]: 25 µl of lysis buffer comprising 20 mM sodium citrate, pH 4.0, 26.8 mM sodium chloride, 0.4% NP40, 20 mM EDTA and 20 mM is added to each well. Cell lysis is completed within 60 min at room temperature and total amount of YOPRO™ bound to DNA is determined by measurement using the Cytofluor II 96-well reader (PerSeptive Biosystems) with the following settings: Excitation (nm) 485/20 and Emission (nm) 530/25.

$IC_{50}$ values may be determined by a computer-aided system using the formula: $IC_{50}$=[(ABS test–ABS start)/(ABS control–ABS start)]×100. (ABS=absorption)

The $IC_{50}$ value in those experiments is given as that concentration of the test compound in question that results in a cell count that is 50% lower than that obtained using the control without inhibitor. The compounds of the disclosure in free form or in pharmaceutically acceptable salt form, may exhibit valuable pharmacological properties, for example, as indicated by the in vitro tests described in this application. In general, compounds of the disclosure have $IC_{50}$ values from less than 1 nM to 10 µM. In some examples, compounds of the disclosure have $IC_{50}$ values from less than 1 nM to 500 nM. In other examples, compounds of the disclosure have $IC_{50}$ values from <1 nM to 200 nM.

The antiproliferative action of the inventive compounds may also be determined in the human KARPAS-299 lymphoma cell line (DSMZ Deutsche Sammiung von Mikroorganismen und Zellkulturen GmbH, Braunschweig, Germany, described in W G Dirks et al. Int. J. Cancer 100, 49-56 (2002)) using the same methodology described above for the BaF3-NPM-ALK cell line. In some embodiments, compounds disclosed herein may exhibit inhibitory activity with an $IC_{50}$ in the range from approximately less than 1 nm to 1 µM. The action of the inventive compounds on autophosphorylation of the ALK may be determined in the human KARPAS-299 lymphoma cell line by means of an immunoblot as described in W G Dirks et al. Int. J. Cancer 100, 49-56 (2002).

In accordance with the foregoing, the present disclosure provides:

(1) a compound disclosed herein for use as a pharmaceutical;

(2) a compound disclosed herein for use as an ALK inhibitor, for example, for use in any of the particular indications set forth above;

(3) a pharmaceutical composition, e.g. for use in any of the indications herein set forth above, comprising at least one compound disclosed herein as active ingredient together with one or more pharmaceutically acceptable diluents or carriers;

(4) a method for treatment of any particular indication set forth above in a subject in need thereof which comprises administering an effective amount of at least one compound disclosed herein or at least one pharmaceutical composition comprising thereof;

(5) the use of a compound disclosed herein for making a medicament for treatment or prevention of a disease or condition in which ALK activation plays a role or is implicated;

(6) the method as defined above under (4) comprising co-administration, e.g. concomitantly or in sequence, of a therapeutically effective amount of a compound disclosed herein and one or more additional drug substances, said additional drug substance being useful in any of the particular indications set forth above;

(7) a composition comprising a therapeutically effective amount of at least one compound disclosed herein and at least one additional drug substance, wherein said additional drug substance is useful in any of the particular indications set forth above;

(8) use of a compound disclosed herein for making a medicament for treatment or prevention of a disease which responds to inhibition of the anaplastic lymphoma kinase;

(9) the use according to (8), wherein the disease to be treated is selected from anaplastic large cell lymphoma, non-Hodgkin's lymphomas, inflammatory myofibroblastic tumors, neuroblastomas and neoplastic diseases;

(10) the use according to (8) or (9), wherein the compound is a pharmaceutically acceptable salt of any one of the examples disclosed herein;

(11) a method for the treatment of a disease which responds to inhibition of the anaplastic lymphoma kinase, such as a disease selected from anaplastic large-cell lymphoma, non Hodgkin's-lymphomas; inflammatory myofibroblastic tumors, neuroblastomas and neoplastic diseases, comprising administering an effective amount of at least one compound disclosed herein and/or a pharmaceutically acceptable salt thereof. In some examples, the compounds of the disclosure may be used alone or in combination with a chemotherapeutic agent to treat a cell proliferative disorder, including but not limited to, lymphoma, osteosarcoma, melanoma, or a tumor of breast, renal, prostate, colorectal, thyroid, ovarian, pancreatic, neuronal, lung, uterine or gastrointestinal tumor.

Administration and Pharmaceutical Compositions

In general, compounds of the disclosure will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors known to those of ordinary skill in the art. For example, for the treatment of neoplastic diseases and immune system disorders, the required dosage will also vary depending on the mode of administration, the particular condition to be treated and the effect desired.

In general, satisfactory results are indicated to be obtained systemically at daily dosages of from about 0.001 to about 100 mg/kg per body weight, or particularly, from about 0.03 to 2.5 mg/kg per body weight. An indicated daily dosage in the larger mammal, e.g. humans, may be in the range from about 0.5 mg to about 2000 mg, or more particularly, from about 0.5 mg to about 100 mg, conveniently administered, for example, in divided doses up to four times a day or in retard form. Suitable unit dosage forms for oral administration comprise from ca. 1 to 50 mg active ingredient.

Compounds of the disclosure may be administered as pharmaceutical compositions by any conventional route; for example, enterally, e.g., orally, e.g., in the form of tablets or capsules; parenterally, e.g., in the form of injectable solutions or suspensions; or topically, e.g., in the form of lotions, gels, ointments or creams, or in a nasal or suppository form.

Pharmaceutical compositions comprising a compound of the present disclosure in free form or in a pharmaceutically acceptable salt form in association with at least one pharmaceutically acceptable carrier or diluent may be manufactured in a conventional manner by mixing, granulating, coating, dissolving or lyophilizing processes. For example, pharmaceutical compositions comprising a compound of the disclosure in association with at least one pharmaceutical acceptable carrier or diluent may be manufactured in conventional manner by mixing with a pharmaceutically acceptable carrier or diluent. Unit dosage forms for oral administration contain, for example, from about 0.1 mg to about 500 mg of active substance.

In one embodiment, the pharmaceutical compositions are solutions of the active ingredient, including suspensions or dispersions, such as isotonic aqueous solutions. In the case of lyophilized compositions comprising the active ingredient alone or together with a carrier such as mannitol, dispersions or suspensions can be made up before use. The pharmaceutical compositions may be sterilized and/or contain adjuvants, such as preserving, stabilizing, wetting or emulsifying agents, solution promoters, salts for regulating the osmotic pressure and/or buffers. Suitable preservatives include but are not limited to antioxidants such as ascorbic acid, or microbicides, such as sorbic acid or benzoic acid. The solutions or suspensions may further comprise viscosity-increasing agents, including but not limited to, sodium carboxymethylcellulose, carboxymethylcellulose, dextran, polyvinylpyrrolidone, gelatins, or solubilizers, e.g. Tween 80 (polyoxyethylene(20)sorbitan mono-oleate).

Suspensions in oil may comprise as the oil component the vegetable, synthetic, or semi-synthetic oils customary for injection purposes. Examples include liquid fatty acid esters that contain as the acid component a long-chained fatty acid having from 8 to 22 carbon atoms, or in some embodiments, from 12 to 22 carbon atoms. Suitable liquid fatty acid esters include but are not limited to lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid and linoleic acid, and if desired, may contain antioxidants, for example vitamin E, 3-carotene or 3,5-di-tert-butyl-hydroxytoluene. The alcohol component of these fatty acid esters may have six carbon atoms and may be monovalent or polyvalent, for example a mono-, di- or trivalent, alcohol. Suitable alcohol components include but are not limited to methanol, ethanol, propanol, butanol or pentanol or isomers thereof; glycol and glycerol.

Other suitable fatty acid esters include but are not limited ethyl-oleate, isopropyl myristate, isopropyl palmitate, LABRAFIL® M 2375, (polyoxyethylene glycerol), LABRAFIL® M 1944 CS (unsaturated polyglycolized glycerides prepared by alcoholysis of apricot kernel oil and comprising glycerides and polyethylene glycol ester), LABRASOL™ (saturated polyglycolized glycerides prepared by alcoholysis of TCM and comprising glycerides and polyethylene glycol ester; all available from GaKefosse, France), and/or MIGLYOL® 812 (triglyceride of saturated fatty acids of chain length C8 to C12 from Hüls AG, Germany), and vegetable oils such as cottonseed oil, almond oil, olive oil, castor oil, sesame oil, soybean oil, or groundnut oil.

Pharmaceutical compositions for oral administration may be obtained, for example, by combining the active ingredient with one or more solid carriers, and if desired, granulating a resulting mixture, and processing the mixture or granules by the inclusion of additional excipients, to form tablets or tablet cores.

Suitable carriers include but are not limited to fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, carboxymethyl starch, crosslinked polyvinylpyrrolidone, alginic acid or a salt thereof, such as sodium alginate. Additional excipients include flow conditioners and lubricants, for example silicic acid, talc, stearic acid or salts thereof, such as magnesium or calcium stearate, and/or polyethylene glycol, or derivatives thereof.

Tablet cores may be provided with suitable, optionally enteric, coatings through the use of, inter alia, concentrated sugar solutions which may comprise gum arable, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or tablet coatings, for example for identification purposes or to indicate different doses of active ingredient.

Pharmaceutical compositions for oral administration may also include hard capsules comprising gelatin or soft-sealed capsules comprising gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient may be dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories comprising a combination of the active ingredient and a suppository base. Suitable suppository bases are, for example, natural or synthetic triglycerides, paraffin hydrocarbons, polyethylene glycols or higher alkanols.

Pharmaceutical compositions suitable for parenteral administration may comprise aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers. The active ingredient, optionally together with excipients, can also be in the form of a lyophilizate and can be made into a solution before parenteral administration by the addition of suitable solvents. Solutions such as are used, for example, for parenteral administration can also be employed as infusion solutions. The manufacture of injectable preparations is usually carried out under sterile conditions, as is the filling, for example, into ampoules or vials, and the sealing of the containers.

The compounds of the disclosure may be administered as the sole active ingredient, or together with other drugs useful against neoplastic diseases or useful in immunomodulating regimens. For example, the compounds of the disclosure may be used in accordance with the disclosure in combination with pharmaceutical compositions effective in various diseases as described above, e.g. with cyclophosphamide, 5-fluorouracil, fludarabine, gemcitabine, cisplatinum, carboplatin, vincristine, vinblastine, etoposide, irinotecan, paclitaxel, docetaxel, rituxan, doxorubicine, gefitinib, or imatinib; or also with cyclosporins, rapamycins, ascomycins or their immunosuppressive analogs, e.g. cyclosporin A, cyclosporin G, FK-506, sirolimus or everolimus, corticosteroids, e.g. prednisone, cyclophosphamide, azathioprene, methotrexate, gold salts, sulfasalazine, antimalarials, brequinar, leflunomide, mizoribine, mycophenolic acid, mycophenolate, mofetil, 15-deoxyspergualine, immuno-suppressive monoclonal antibodies, e.g. monoclonal antibodies to leukocyte receptors, e.g. MHC, CD2, CD3, CD4, CD7, CD25, CD28, I CD40, CD45, CD58, CD80, CD86, CD152, CD137, CD154, ICOS, LFA-1, VLA-4 or their ligands, or other immunomodulatory compounds, e.g. CTLA41g.

The disclosure also provides for a pharmaceutical combinations, e.g. a kit, comprising a) a first agent which is a compound of the disclosure as disclosed herein, in free form or in pharmaceutically acceptable salt form, and b) at least one co-agent. The kit can comprise instructions for its administration.

EXAMPLES

Various methods may be developed for synthesizing the at least one compound of formula (I) and/or at least one pharmaceutically acceptable salt thereof. Representative methods for synthesizing the at least one compound of formula (I) and/or at least one pharmaceutically acceptable salt thereof are provided in the Examples. It is noted, however, that the at least one compound of formula (I) and/or at least one pharmaceutically acceptable salt thereof may also be synthesized by other synthetic routes that others may devise.

It will be readily recognized that certain compounds of formula (I) have atoms with linkages to other atoms that confer a particular stereochemistry to the compound (e.g., chiral centers). It is recognized that synthesis of the at least one compound of formula (I) and/or at least one pharmaceutically acceptable salt thereof may result in the creation of mixtures of different stereoisomers (enantiomers, diastereomers). Unless a particular stereochemistry is specified, recitation of a compound is intended to encompass all of the different possible stereoisomers.

The at least one compound of formula (I) can also be prepared as a pharmaceutically acceptable acid addition salt by, for example, reacting the free base form of the at least one compound with a pharmaceutically acceptable inorganic or organic acid. Alternatively, a pharmaceutically acceptable base addition salt of the at least one compound of formula (I) can be prepared by, for example, reacting the free acid form of the at least one compound with a pharmaceutically acceptable inorganic or organic base. Inorganic and organic acids and bases suitable for the preparation of the pharmaceutically acceptable salts of compounds of formula (I) are set forth in the definitions section of this Application. Alternatively, the salt forms of the compounds of formula (I) can be prepared using salts of the starting materials or intermediates.

The free acid or free base forms of the compounds of formula (I) can be prepared from the corresponding base addition salt or acid addition salt form. For example, a compound of formula (I) in an acid addition salt form can be converted to the corresponding free base thereof by treating with a suitable base (e.g., ammonium hydroxide solution, sodium hydroxide, and the like). A compound of formula (I) in a base addition salt form can be converted to the corresponding free acid thereof by, for example, treating with a suitable acid (e.g., hydrochloric acid, etc).

The N-oxides of the at least one compound of formula (I) and/or at least one pharmaceutically acceptable salt thereof can be prepared by methods known to those of ordinary skill in the art. For example, N-oxides can be prepared by treating an unoxidized form of the compound of formula (I) with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0 to 80° C. Alternatively, the N-oxides of the compounds of formula (I) can be prepared from the N-oxide of an appropriate starting material.

Compounds of formula (I) in an unoxidized form can be prepared from N-oxides of compounds of formula (I) by, for example, treating with a reducing agent (e.g., sulfur, sulfur dioxide, triphenyl phosphine, lithium borohydride, sodium borohydride, phosphorus trichloride, tribromide, and the like) in an suitable inert organic solvent (e.g., acetonitrile, ethanol, aqueous dioxane, and the like) at 0 to 80° C.

Protected derivatives of the compounds of formula (I) can be made by methods known to those of ordinary skill in the art. A detailed description of the techniques applicable to the creation of protecting groups and their removal can be found in T. W. Greene, Protecting Groups in Organic Synthesis, 3rd edition, John Wiley & Sons, Inc. 1999.

The at least one compound of formula (I) and/or at least one pharmaceutically acceptable salt thereof may be conveniently prepared, or as solvates (e.g. hydrates). Hydrates of the at least one compound of formula I and/or at least one pharmaceutically acceptable salt thereof may be conveniently prepared by recrystallization from an aqueous/organic solvent mixture, using organic solvents such as dioxin, tetrahydrofuran and/or methanol.

The compounds of formula (I) can also be prepared as their individual stereoisomers by reacting a racemic mixture of the compounds with an optically active resolving agent to form a pair of diastereoisomeric compounds, separating the diastereomers, and recovering the optically pure enantiomer. While resolution of enantiomers can be carried out using covalent diasteromeric derivatives of compounds, dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, for example, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. For example, the following abbreviations may be used in the examples and throughout the specification: g (grams); mg (milligrams); L (liters); mL (milliliters); µL (microliters); psi (pounds per square inch); M (molar); mM (millimolar); i.v. (intravenous); Hz (Hertz); MHz (megahertz); mol (moles); mmol (millimoles); RT (room temperature); min (minutes); h (hours); mp (melting point); TLC (thin layer chromatography); Rt (retention time); RP (reverse phase); MeOH (methanol); i-PrOH (isopropanol); TEA (triethylamine); TFA (trifluoroacetic acid); TFAA (trifluoroacetic anhydride); THF (tetrahydrofuran); DMSO (dimethyl sulfoxide); EtOAc (ethyl acetate); DME (1,2-dimethoxyethane); DCM (dichloromethane); DCE (dichloroethane); DMF (N,N-dimethylformamide); DMPU (N,N'-dimethylpropyleneurea); CDI (1,1-carbonyldiimidazole); IBCF (isobutyl chloroformate); HOAc (acetic acid); HOSu (N-hydroxysuccinimide); HOBT (1-hydroxybenzotriazole); Et$_2$O (diethyl ether); EDCI (1-(3-dimethylaminopropyl)-3-ethylcarbodiimide hydrochloride); BOC (tert-butyloxycarbonyl); FMOC (9-fluorenylmethoxycarbonyl); DCC (dicyclohexylcarbodiimide); CBZ (benzyloxycarbonyl); Ac (acetyl); atm (atmosphere); TMSE (2-(trimethylsilyl)ethyl); TMS (trimethylsilyl); TIPS (triisopropylsilyl); TBS (t-butyldimethylsilyl); DMAP (4-dimethylaminopyridine); Me (methyl); OMe (methoxy); Et (ethyl); tBu (tert-butyl); HPLC (high pressure liquid chomatography); BOP (bis(2-oxo-3-oxazolidinyl)phosphinic chloride); TBAF (tetra-n-butylammonium fluoride); m-CPBA (meta-chloroperbenzoic acid).

References to ether or Et$_2$O are to diethyl ether, brine refers to a saturated aqueous solution of NaCl. Unless otherwise indicated, all temperatures are expressed in ° C. (degrees Centigrade). All reactions were conducted under an inert atmosphere at RT unless otherwise noted.

$^1$H NMR spectra were recorded on a Varian Mercury Plus 400. Chemical shifts are expressed in parts per million (ppm). Coupling constants are in units of hertz (Hz). Splitting patterns describe apparent multiplicities and are designated as s (singlet), d (doublet), t (triplet), q (quartet), m (multiplet), and br (broad).

Low-resolution mass spectra (MS) and compound purity data were acquired on a Shimadzu LC/MS single quadrapole system equipped with electrospray ionization (ESI) source, UV detector (220 and 254 nm), and evaporative light scattering detector (ELSD). Thin-layer chromatography was performed on 0.25 mm E. Merck silica gel plates (60F-254), visualized with UV light, 5% ethanolic phosphomolybdic acid, ninhydrin, or p-anisaldehyde solution. Flash column chromatography was performed on silica gel (230-400 mesh, Merck).

Synthetic Schemes

The at least one compound of formula (I) and/or at least one pharmaceutically acceptable salt thereof may be synthesized according to a variety of reaction schemes. Some illustrative schemes are provided below and in the examples. Other reaction schemes could be readily devised by those skilled in the art in view of the present disclosure.

In the reactions disclosed below, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for example, see T. W. Greene and P. G. M. Wuts in "Protective Groups in Organic Chemistry" John Wiley and Sons, 1991.

Synthetic methods for preparing the compounds in the present disclosure are illustrated in the following Schemes and Examples. Starting materials are commercially available or may be made according to procedures known in the art or as illustrated herein.

Preparation of Intermediates

Intermediate A

4-Hydroxy-3-methyl-6-mercaptopyrazolo[3,4-d]pyrimidine (A-1)

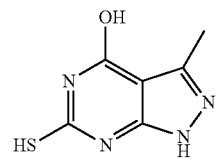

A-1

This reagent was prepared according to the method described in literature: *J. Med. Chem.* 1990, 33: 2174-2178.

4-Hydroxy-3-methyl-6-methylmercaptopyrazolo[3,4-d]pyrimidine (A-2)

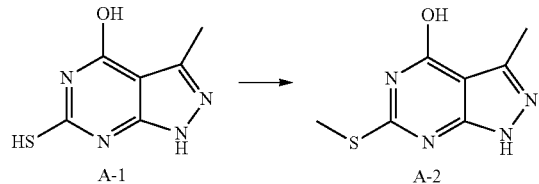

To a mixture of 4-hydroxy-6-mercapto-3-methylpyrazolo[3,4-d]pyrimidine (A-1) (2.86 g, 11.8 mmol) and NaOH (0.8 g, 20 mmol) in water (20 mL) at 5° C., was added CH$_3$I (2.0 g, 14.2 mmol). After stirred at ambient temperature for 30 min, the solution was acidified with HOAc to give the crude product of the title compound (A-2), which used in next step without further purification. MS-ESI (m/z): 197.0 (M+H)$^+$.

4-chloro-3-methyl-6-methylmercaptopyrazolo[3,4-d]pyrimidine (A-3)

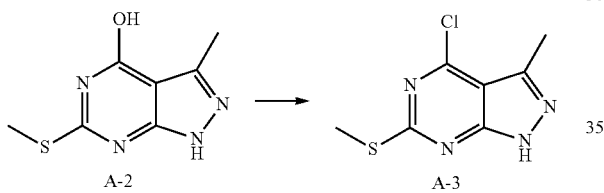

To a mixture of POCl$_3$ (26 mL) and of dimethylaniline (2 mL) was added crude 4-hydroxy-3-methyl-6-methylmercaptopyrazolo[3,4-d]pyrimidine (A-2) (1.46 g, 7.45 mmol). The solution was heated to reflux for 60 min until all solid dissolved. The excess of POCl$_3$ was removed under reduced pressure. The residue was poured into ice water with vigorous stirring, it is stirred for 10 min, and the aqueous solution was extracted with ether. The ether layer was washed with cold water, dried with anhydrous Na$_2$SO$_4$ and concentrated to give the title compound (A-3) (1.21 g, 5.63 mmol). MS-ESI (m/z): 215.0 (M+H)$^+$.

2-(isopropylthio)aniline (A-4)

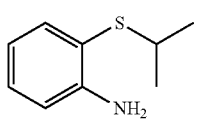

This reagent was prepared according to the method described in literature: J. Med. Chem. 2002, 45: 2229-2239.

N-(2-(isopropylthio)phenyl)-3-methyl-6-(methylthio)-1H-pyrazolo[3,4-d]pyrimidin-4-amine (A-5)

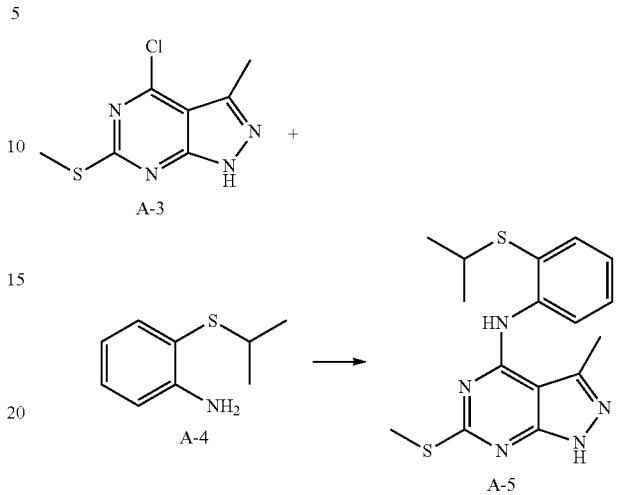

A mixture of 4-chloro-3-methyl-6-methylmercaptopyrazolo[3,4-d]pyrimidine (A-3) (1.21 g, 5.63 mmol) and 2-(isopropylthio)aniline (A-4) (1.42 g, 8.50 mmol) in isopropanol (56 mL) was stirred at reflux for 3 h. After cooling down to ambient temperature, TEA (0.78 mL, 5.66 mmol) was added to the mixture, and the solution was again heated to reflux for 0.5 h. After cooling down to ambient temperature, the mixture was filtered to give the title compound (A-5) as white solid (1.30 g, 3.77 mmol). MS-ESI (m/z): 346 (M+H)$^+$.

N-(2-(isopropylsulfonyl)phenyl)-3-methyl-6-(methylsulfonyl)-1H-pyrazolo[3,4-d]pyrimidin-4-amine (Intermediate A)

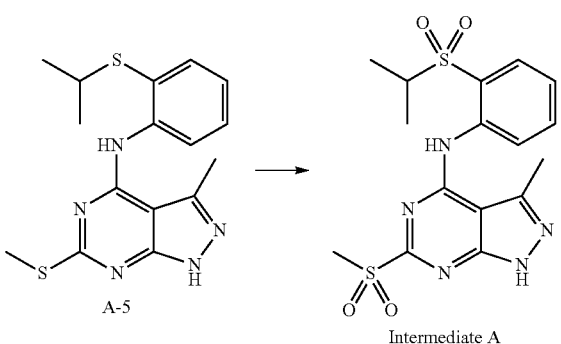

To a solution of N-(2-(isopropylsulfonyl)phenyl)-6-(methylthio)-1H-pyrazolo[3,4-d]pyrimidin-4-amine (A-5) (1.3 g, 3.77 mmol) in DCM (150 mL) was added m-CPBA (5.6 g, 22.6 mmol) at 0° C. Then the reaction mixture was warmed to ambient temperature and stirred for 4.5 h, washed with saturated NaHSO$_3$, brine, dried with Na$_2$SO$_4$ and concentrated to give the title compound (Intermediate A) as a solid. MS-ESI (m/z): 410 (M+H)$^+$.

Intermediate B

2,5-dichloro-N-(2-(isopropylsulfonyl)phenyl)pyrimidin-4-amine (B)

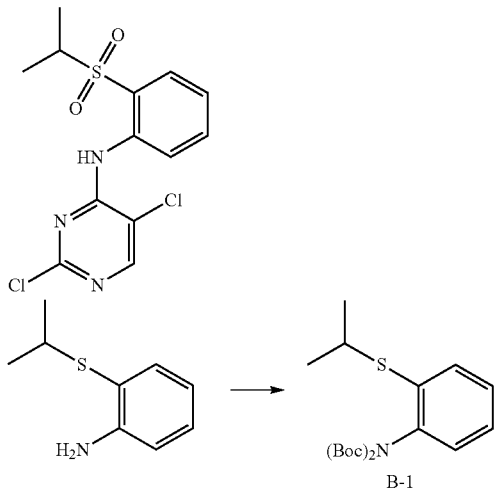

To a mixture of 2-(isopropylthio)aniline (23 g, 0.14 mol) in acetonitrile (250 mL) at RT was added DMAP (8.5 g, 70 mmol) and (Boc)$_2$O (150 g, 688 mmol). After stirred at ambient temperature for 12 h, the solution was concentrated. The residue was purified by column chromatography on silica gel eluting with hexanes/EtOAc (10:1) to give the title compound (B-1).

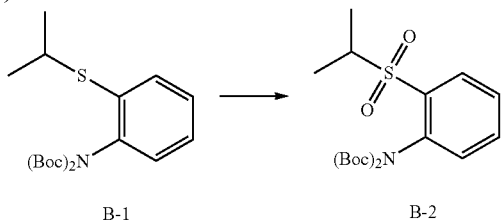

To a mixture of (B-1) (54 g, 0.14 mol) in DCM (500 mL) at 0° C. was added m-CPBA (101 g. 0.44 mol). After stirred at ambient temperature for 12 h, the solution was washed with saturated NaHSO$_3$, brine, dried with Na$_2$SO$_4$ and concentrated to give the compound (B-2) as a solid.

2-(isopropylsulfonyl)aniline (B-3)

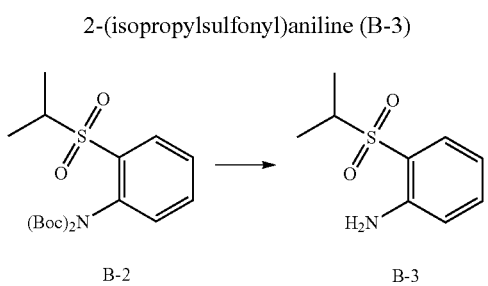

To a mixture of (B-2) (64 g, 0.32 mol) in DCM (500 mL) at 0° C., was added TFA (60 mL, 1 mol). After stirred at ambient temperature for 12 h, the solution was concentrated, diluted with EtOAc, washed with saturated. Na$_2$CO$_3$, brine, dried with Na$_2$SO$_4$ and concentrated to give the compound (B-3) as a solid. MS-ESI (m/z): 200 (M+1)$^+$.

2,5-dichloro-N-(2-(isopropylsulfonyl)phenyl)pyrimidin-4-amine (B)

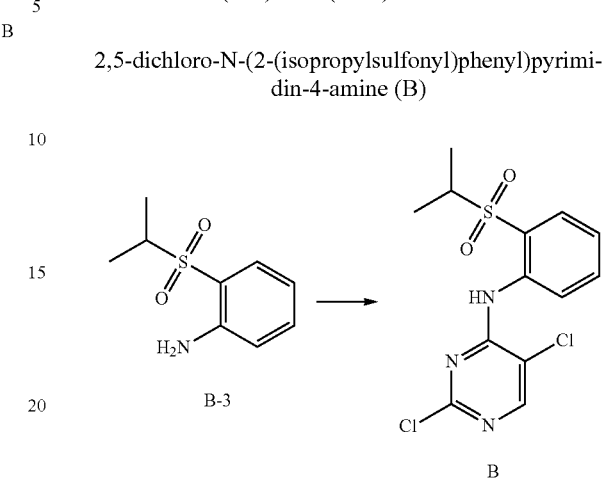

To a mixture of 2-(isopropylsulfonyl)aniline (B-3) (32 g, 0.16 mol) in DMF (300 mL) at 0° C., was added NaH (13 g, 0.32 mol). After stirred at 0° C. for 0.5 h, 2,4,5-trichloropyrimidine (35 g, 0.13 mol) was dropwised to the mixture at 0° C. The solution was stirred for 12 h at RT, then poured into water, extracted with EtOAc, washed with water, brine, dried and concentrated. The residue was purified by column chromatography on silica gel eluting with hexanes/EtOAc (10:1 to 5:1) to give the title compound (B) as a yellow solid. MS-ESI (m/z): 346 (M+1)$^+$.

Example 1

N-4-(2-(isopropylsulfonyl)phenyl)-3-methyl-N-6-(5-methyl-4-(piperidin-4-yl)-2,3-dihydrobenzofuran-7-yl)-1H-pyrazolo[3,4-d]pyrimidine-4,6-diamine (I)

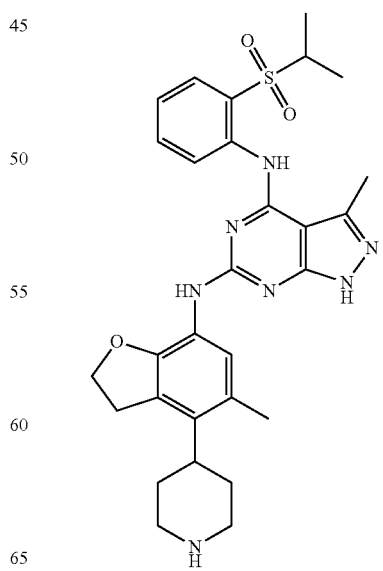

2-bromo-1-(2-bromoethoxy)-4-methylbenzene (1a)

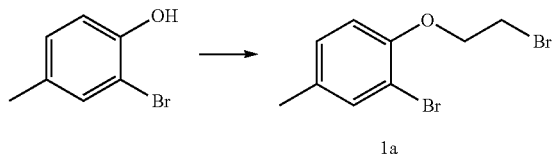

A mixture of 2-bromo-4-methylphenol (5.0 g, 26 mmol), 1,2-dibromoethane (7.0 g, 37 mmol) in water (20 mL) and NaOH (1.1 g, 28 mmol) was stirred at 100° C. for 24 h. The mixture was extracted with DCM (150 mL), washed with water, brine, dried and concentrated. The residue was purified by column chromatography on silica gel eluting with hexanes/EtOAc (20:1) to give the title compound (1a).

5-methyl-2,3-dihydrobenzofuran (1b)

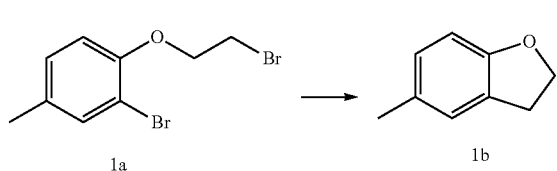

To a solution of 2-bromo-1-(2-bromoethoxy)-4-methylbenzene (1a) (1.0 g, 3.4 mmol) in THF (20 mL) at −78° C., under $N_2$ was added n-BuLi (2.5 M, 11 mL, 27 mmol) and the resulting mixture was stirred at −78° C., for 1 h. The mixture was quenched with saturated $NH_4Cl$ (10 mL), extracted with EtOAc (150 mL), washed with brine, dried and concentrated to give the title compound (1b) as a colorless oil.

5-methyl-7-nitro-2,3-dihydrobenzofuran (1c)

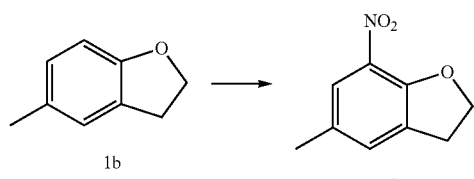

A mixture of 5-methyl-2,3-dihydrobenzofuran (1b) (2.7 g, 20 mmol) in TFA (50 mL) was cooled to 0° C., $NaNO_2$ (2.5 g, 36 mmol) was added thereto. Then it was warmed up to ambient temperature and stirred for 12 h. The mixture was concentrated, poured into water (50 mL), extracted with EtOAc (150 mL), washed with brine, dried and concentrated. The residue was purified by column chromatography on silica gel eluting with hexanes/EtOAc (10:1) to give the title compound (1c).

5-methyl-2,3-dihydrobenzofuran-7-amine (1d)

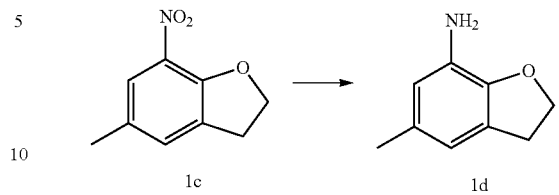

A mixture of 5-methyl-7-nitro-2,3-dihydrobenzofuran (1c) (0.30 g, 1.7 mmol) and Pd/C (150 mg, 50%) in THF (5 mL) was introduced $H_2$. It was stirred at ambient temperature for 12 h. The mixture was filtered through celite and concentrated to give the title compound (1d) as a solid. MS-ESI (m/z): 150 $(M+1)^+$.

4-bromo-5-methyl-2,3-dihydrobenzofuran-7-amine (1e)

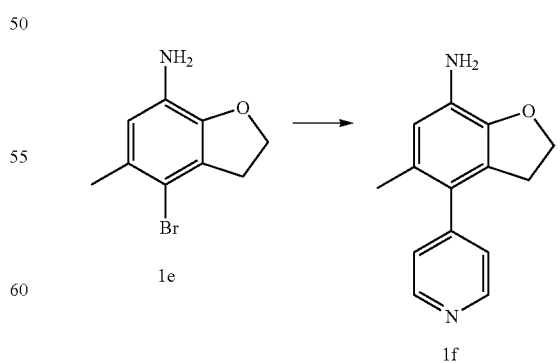

To a mixture of 5-methyl-2,3-dihydrobenzofuran-7-amine (1d) (1.0 g, 6.7 mmol) in DMF (21 mL) at 0° C., was added NBS (1.19 g, 6.7 mmol), it was stirred at 0° C., for 15 min. The mixture was extracted with EtOAc (150 mL), washed with saturated $NaHSO_3$ (50 mL), water, brine, dried and concentrated. The residue was purified by column chromatography on silica gel eluting with hexanes/EtOAc (20:1) to give the title compound (1e) as a yellow solid. MS-ESI (m/z): 228 $(M+1)^+$.

5-methyl-4-(pyridin-4-yl)-2,3-dihydrobenzofuran-7-amine (1f)

A mixture of 4-bromo-5-methyl-2,3-dihydrobenzofuran-7-amine (1e) (0.80 g, 3.5 mmol), pyridin-4-ylboronic acid (0.86 g, 7 mmol), $Cs_2CO_3$ (2.84 g, 8.7 mmol), $Pd(PPh_3)_4$ (0.40 g, 0.346 mmol) and water (7 mL) in DMF (35 mL) was stirred at 135° C., under N₂ for 1 h. It was cooled to ambient temperature, poured into water (50 mL), extracted with EtOAc (150 mL), washed with water, brine, dried and concentrated. The residue was purified by column chromatography on silica gel eluting with hexanes/EtOAc (20:1 to 5:1 to 1:1) to give the title compound (1f) as a yellow solid. MS-ESI (m/z): 227 (M+1)⁺.

5-methyl-4-(piperidin-4-yl)-2,3-dihydrobenzofuran-7-amine (1g)

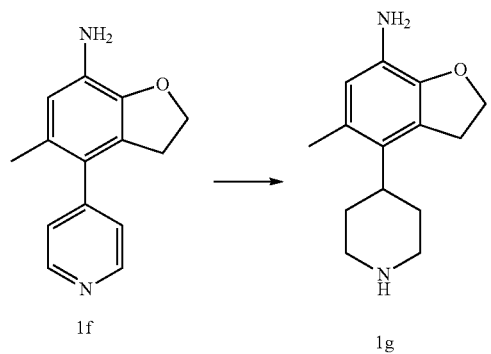 [SMILES: Cc1cc(N)c2c(c1-c1ccncc1)CCO2 ; Cc1cc(N)c2c(c1C1CCNCC1)CCO2]

A mixture of 5-methyl-4-(pyridin-4-yl)-2,3-dihydrobenzofuran-7-amine (1f) (0.40 g, 1.8 mmol), PtO₂ (120 mg, 35%) and TEA (0.24 mL, 3.6 mmol) in HOAc (30 mL) was introduced H₂ and stirred at ambient temperature for 24 h (88 psi). The mixture was filtered, concentrated, diluted with EtOAc (50 mL). A solution of ammonium hydroxide was added until pH=10, it was extracted with EtOAc (150 mL), washed with water, brine, dried and concentrated to give the title compound (1g) as a yellow oil. MS-ESI (m/z): 233 (M+1)⁺.

N-4-(2-isopropylsulfonyl)phenyl)-3-methyl-N-6-(methyl-4-(piperidin-4-yl)-2,3-dihydrobenzofuran-7-yl)-1H-pyrazolo[3,4-d]pyrimidine-4,6-diamine (1)

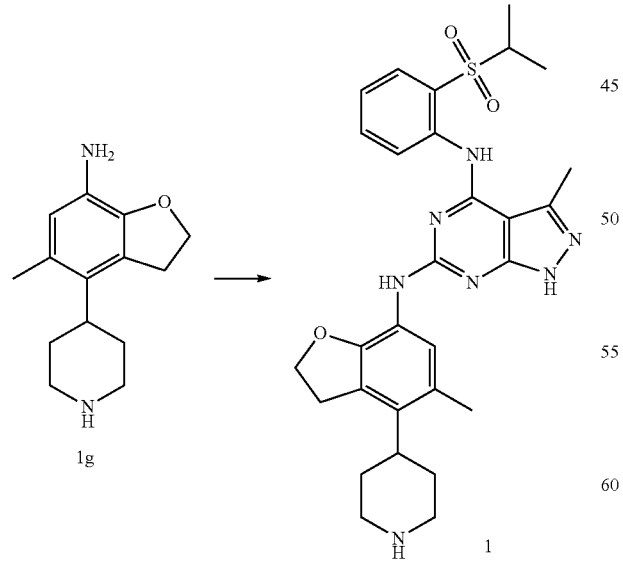

A mixture of 5-methyl-4-(piperidin-4-yl)-2,3-dihydrobenzofuran-7-amine (1g) (25 mg, 0.017 mmol), N-(2-(isopropylsulfonyl)phenyl)-3-methy-6-(methylsulfonyl)-1H-pyrazolo[3,4-d]pyrimidin-4-amine (intermediate A) (53 mg, 0.12 mmol) and p-TsOH (20 mg, 0.11 mmol) in i-PrOH (0.5 mL) was stirred in a sealed tube at 160° C., for 5 h. The mixture was diluted with EtOAc (20 mL). A solution of ammonium hydroxide was added until pH=10, it was extracted with EtOAc (60 mL), washed with water, brine, dried and concentrated. The residue was purified by column chromatography on silica gel eluting with DCM/MeOH (10:1) to give the title compound (1) as a yellow solid. MS-ESI (m/z): 562 (M+1)⁺.

Example 2

N-4-(2-isopropylsulfonyl)phenyl)-3-methyl-N-6-(5-methyl-4-(1-methylpiperidin-4-yl)-2,3-dihydrobenzofuran-7-yl)-1H-pyrazolo[3,4-d]pyrimidine-4,6-diamine (2)

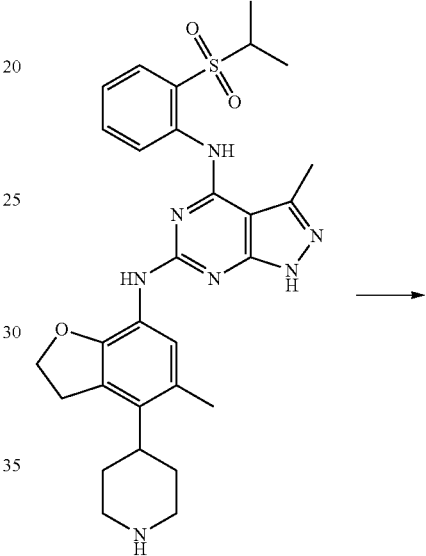

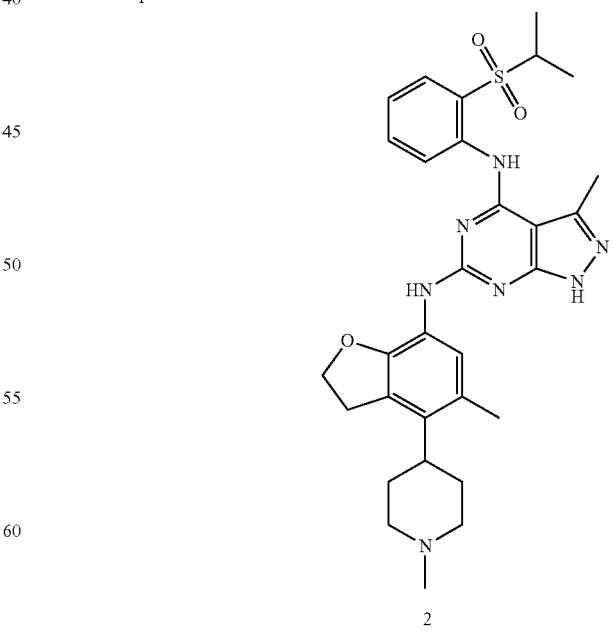

A mixture of N-4-(2-(isopropylsulfonyl)phenyl)-3-methyl-N-6-(5-methyl-4-(piperidin-4-yl)-2,3-dihydrobenzofuran-7-yl)-1H-pyrazolo[3,4-d]pyrimidine-4,6-diamine (1) (37 mg, 0.064 mmol), formaldehyde (5.5 μL, 0.64 mmol), HOAc (cat.) and NaBH$_3$CN (10.3 mg, 0.16 mmol) was stirred at ambient temperature for 0.5 h. The mixture was diluted with NaHCO$_3$ (10 mL) and EtOAc (20 mL), extracted with EtOAc (60 mL), washed with water, brine, dried and concentrated. The residue was purified by column chromatography on silica gel eluting with DCM/MeOH (10:1) to give the title compound (2) as a yellow solid. MS-ESI (m/z): 576 (M+1)$^+$.

Example 3

(R)—N-6-(2,5-dimethyl-4-(piperidin-4-yl)-2,3-dihydrobenzofuran-7-yl)-N-4-(2-(isopropylsulfonyl)phenyl)-3-methyl-1H-pyrazolo[3,4-d]pyrimidine-4,6-diamine (3)

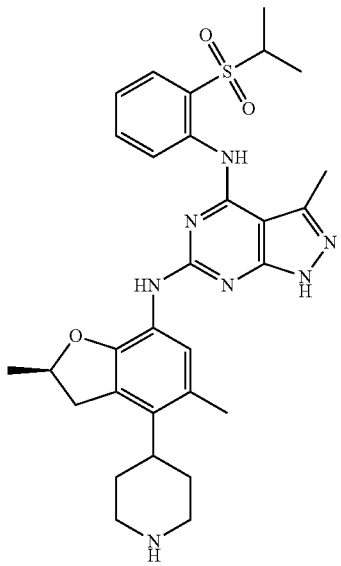

1-(benzyloxy)-2-bromo-4-methylbenzene (3a)

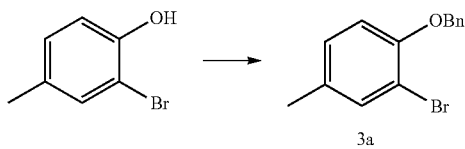

To a mixture of 2-bromo-4-methylphenol (5.0 g, 27 mmol) and K$_2$CO$_3$ (7.4 g, 53 mmol) in DMF (20 mL) was added benzyl bromide (3.5 mL, 29 mmol) at ambient temperature. It was stirred at 70° C., for 12 h. The mixture was poured into water (50 mL), extracted with EtOAc (150 mL), washed with water, brine, dried and concentrated. The residue was purified by column chromatography on silica gel eluting with hexanes/EtOAc (10:1) to give the title compound (3a).

(S)-1-(2-(benzyloxy)-5-methylphenyl)propan-2-ol (3b)

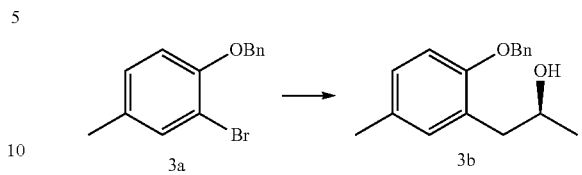

To a solution of 1-(benzyloxy)-2-bromo-4-methylbenzene (3a) (1.0 g, 3.6 mmol) in THF (20 mL) at −78° C. under N$_2$ atmosphere was added n-BuLi (2.5 M, 1.6 mL, 3.9 mmol), the resulting mixture was stirred for 30 min and (S)-2-methyloxirane (0.38 mL, 5.4 mmol) and BF$_3$.Et$_2$O (0.67 mL, 5.4 mmol) were added to the mixture. It was stirred at −78° C. for 1.5 h and warmed up to ambient temperature, quenched with water (10 mL), extracted with EtOAc (30 mL), washed with brine, dried and concentrated. The residue was purified by column chromatography on silica gel eluting with hexanes/EtOAc (10:1) to give the title compound (3b).

(S)-2-(2-hydroxypropyl)-4-methylphenol (3c)

The mixture of (S)-1-(2-(benzyloxy)-5-methylphenyl)-propan-2-ol (3b) (0.50 g, 1.9 mmol) and Pd/C (100 mg, 20%) in MeOH (10 mL) was introduced H$_2$ at ambient temperature. It was stirred at ambient temperature for 18 h. The mixture was filtered through Celite and concentrated to give the title compound (3c).

(R)-2,5-dimethyl-2,3-dihydrobenzofuran (3d)

To a mixture of (S)-2-(2-hydroxypropyl)-4-methylphenol (3c) (1.6 g, 8.4 mmol) and triphenylphosphine (2.7 g, 10 mmol) in THF (60 mL) was added DIAD at ambient temperature. It was concentrated in vacuo. The residue was purified by column chromatography on silica gel eluting with hexanes/EtOAc (10:1) to give the title compound (3d).

(R)-2,5-dimethyl-7-nitro-2,3-dihydrobenzofuran (3e)

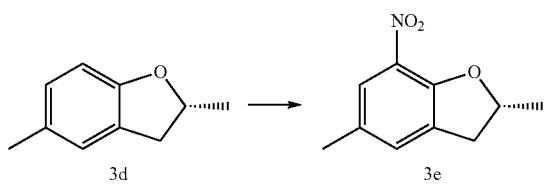

A mixture of (R)-2,5-dimethyl-2,3-dihydrobenzofuran (3d) (2.0 g, 13 mmol) in TFA (40 mL) was cooled to 0° C., NaNO₂ (1.7 g, 23 mmol) was added thereto. It was stirred at ambient temperature for 12 h. The mixture was concentrated, poured into water (50 mL), extracted with EtOAc (150 mL), washed with brine, dried and concentrated. The residue was purified by column chromatography on silica gel eluting with hexanes/EtOAc (20:1) to give the title compound (3e).

(R)-2,5-dimethyl-2,3-dihydrobenzofuran-7-amine (3f)

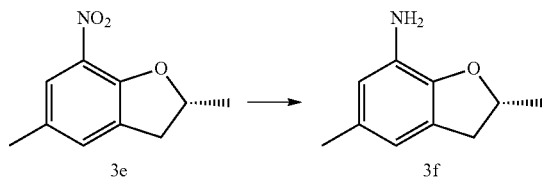

The mixture of (R)-2,5-dimethyl-7-nitro-2,3-dihydrobenzofuran (3e) (0.84 g, 4.3 mmol) and Pd/C (100 mg, 15%) in THF (10 mL) was introduced $H_2$ at ambient temperature. It was stirred at ambient temperature for 12 h. The mixture was filtered through Celite and concentrated to give the title compound (3f) as a solid. MS-ESI (m/z): 164 (M+1)⁺.

(R)-4-bromo-2,5-dimethyl-2,3-dihydrobenzofuran-7-amine (3g)

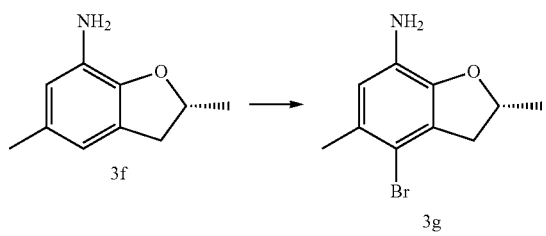

To a mixture of (R)-2,5-dimethyl-2,3-dihydrobenzofuran-7-amine (3f) (1.3 g, 7.9 mmol) in DMF (16 mL) was added NBS (1.42 g, 7.9 mmol) at 0° C. It was stirred for 15 min at 0° C. The mixture was extracted with EtOAc (150 mL), washed with NaHSO₃ (50 mL), water and brine, dried and concentrated. The residue was purified by column chromatography on silica gel eluting with hexanes/EtOAc (20:1) to give the title compound (3g) as a solid. MS-ESI (m/z): 242 (M+1)⁺.

(R)-2,5-dimethyl-4-(pyridin-4-yl)-2,3-dihydrobenzofuran-7-amine (3h)

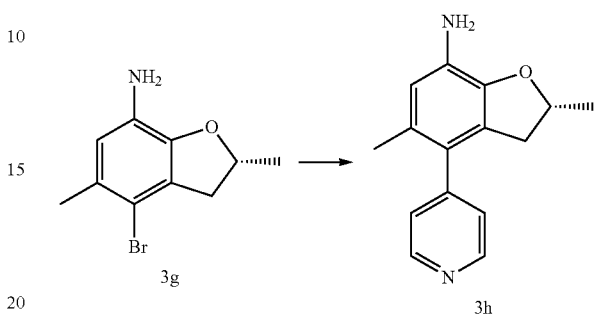

The mixture of (R)-4-bromo-2,5-dimethyl-2,3-dihydrobenzofuran-7-amine (3g) (1.0 g, 4.3 mmol), pyridin-4-ylboronic acid (1.08 g, 8.77 mmol), Cs₂CO₃ (3.56 g, 10.9 mmol), Pd(PPh₃)₄ (0.506 g, 0.438 mmol) and water (9 mL) in DMF (44 mL) was stirred at 135° C. under $N_2$ for 1 h. It was cooled to ambient temperature, poured into water (50 mL), extracted with EtOAc (150 mL, washed with water, brine, dried and concentrated. The residue was purified by column chromatography on silica gel eluting with hexanes/EtOAc (20:1 to 5:1 to 1:1) to give the title compound (3h) as a solid. MS-ESI (m/z): 241 (M+1)⁺.

(R)-2,5-dimethyl-4-(piperidin-4-yl)-2,3-dihydrobenzofuran-7-amine (3i)

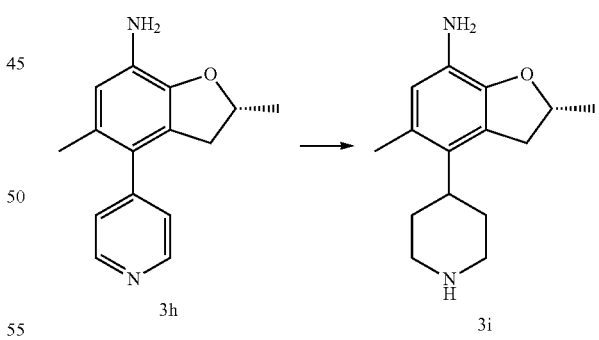

[The mixture of (R)-2,5-dimethyl-4-(pyridin-4-yl)-2,3-dihydrobenzofuran-7-amine (3h) (0.60 g, 2.4 mmol), PtO₂ (240 mg, 35%) and TEA (0.38 mL, 4.9 mmol) in HOAc (40 mL) was introduced $H_2$ and stirred for 24 h at ambient temperature (88 psi). The mixture was filtered, concentrated, and diluted with EtOAc (50 mL). A solution of ammonium hydroxide was added until pH=10, then extracted with EtOAc (150 mL), washed with water, brine, dried and concentrated to give the title compound (3i) as a yellow oil. MS-ESI (m/z): 247 (M+1)⁺.

(R)—N-6-(2,5-dimethyl-4-(piperidin-4-yl)-2,3-dihydrobenzofuran-7-yl)-N-4-(2-(isopropylsulfonyl)phenyl)-3-methyl-1H-pyrazolo[3,4-d]pyrimidine-4,6-diamine (3)

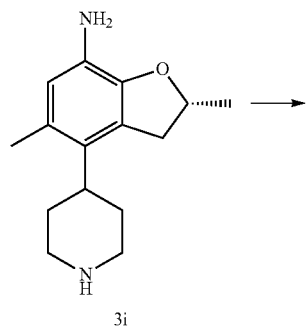

3i

Example 4

(R)—N-6-(2,5-dimethyl-4-(1-methylpiperidin-4-yl)-2,3-dihydrobenzofuran-7-yl)-N-4-(2-(isopropylsulfonyl)phenyl)-3-methyl-1H-pyrazolo[3,4-d]pyrimidin-4,6-diamine (4)

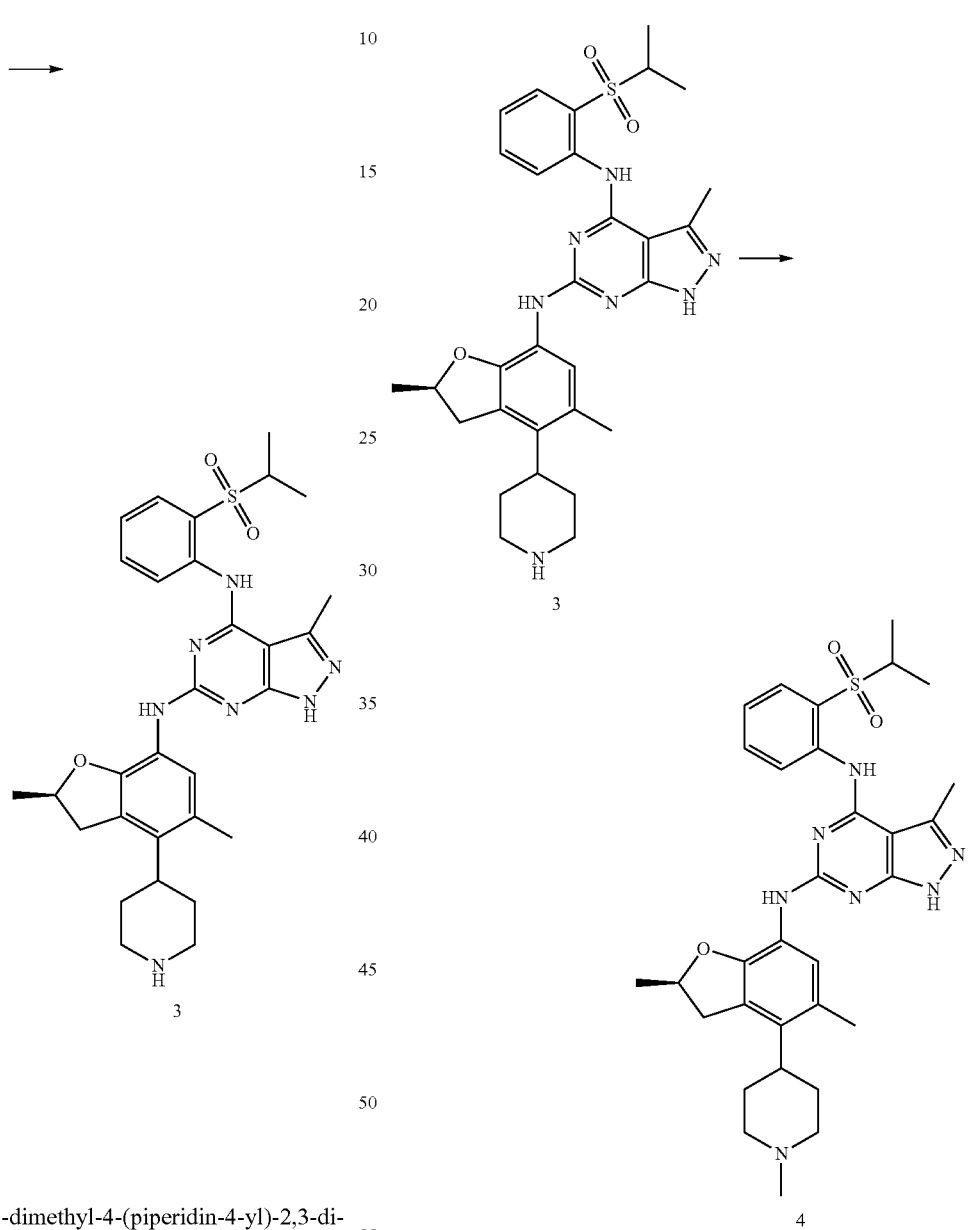

A mixture of (R)-2,5-dimethyl-4-(piperidin-4-yl)-2,3-dihydrobenzofuran-7-amine (3i) (44 mg, 0.017 mmol), N-(2-(isopropylsulfonyl)phenyl)-3-methyl-6-(methylsulfonyl)-1H-pyrazolo[3,4-d]pyrimidin-4-amine (Intermediate A) (83 mg, 0.20 mmol) and p-TsOH (32 mg, 0.17 mmol) in i-PrOH (0.5 mL) was stirred in a sealed tube at 160° C. for 5 h. The mixture was diluted with EtOAc (20 mL), ammonium hydroxide was added until pH=10, it was extracted with EtOAc (60 mL), washed with water, brine, dried and concentrated. The residue was purified by column chromatography on silica gel eluting with DCM/MeOH (10:1) to give the title compound (3) as a yellow solid. MS-ESI (m/z): 576 (M+1)$^+$.

A mixture (R)—N-6-(2,5-dimethyl-4-(piperidin-4-yl)-2,3-dihydrobenzofuran-7-yl)-N-4-(2-(isopropylsulfonyl)phenyl)-3-methyl-1H-pyrazolo[3,4-d]pyrimidine-4,6-diamine (3) (37 mg, 0.064 mmol), formaldehyde (5.5 μL, 0.64 mmol), HOAc (cat.) and NaBH$_3$CN (10.3 mg, 0.16 mmol) was stirred at ambient temperature for 0.5 h. The mixture was diluted with NaHCO$_3$ (10 mL) and EtOAc (20 mL), extracted with EtOAc (60 mL), washed with water, brine, dried and concentrated. The residue was purified by column chromatography on silica gel eluting with DCM/MeOH (10:1) to give the title compound (4) as a solid. MS-ESI (m/z): 590 (M+1)$^+$.

Example 5

(S)—N-6-(2,5-dimethyl-4-(piperidin-4-yl)-2,3-dihydrobenzofuran-7-yl)-N-4-(2-(isopropylsulfonyl)phenyl)-3-methyl-1H-pyrazolo[3,4-d]pyrimidine-4,6-diamine (5)

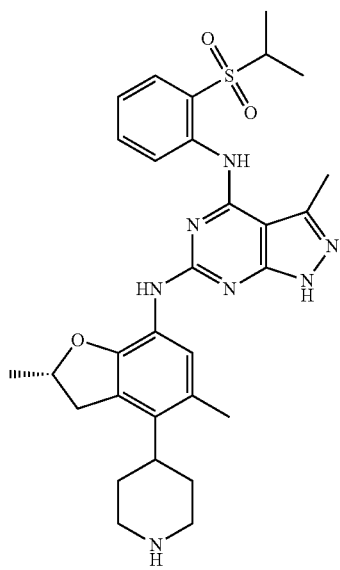

(R)-1-(2-(benzyloxy)-5-methylphenyl)propan-2-ol (5a)

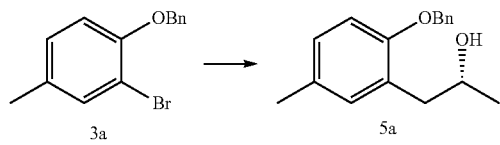 [SMILES: Cc1ccc(OCc2ccccc2)c(Br)c1 ; Cc1ccc(OCc2ccccc2)c(C[C@@H](C)O)c1]

The title compound 5a was prepared according to the method for preparation of compound 3b of Example 3 by replacing (S)-2-methyloxirane with (R)-2-methyloxirane.

(R)-2-(2-hydroxypropyl)-4-methylphenol (5b)

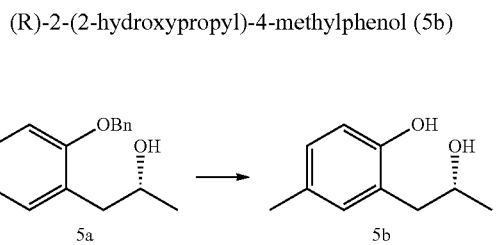

The title compound 5b was prepared according to the method for preparation of compound 3c of Example 3 by replacing 3b with 5a.

(S)-2,5-dimethyl-2,3-dihydrobenzofuran (5c)

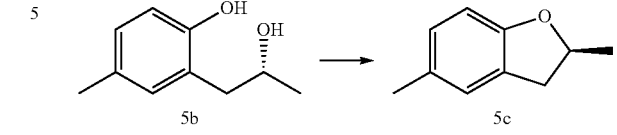

The title compound 5c was prepared according to the method for preparation of compound 3d of Example 3 by replacing 3c with 5b.

(S)-2,5-dimethyl-7-nitro-2,3-dihydrobenzofuran (5d)

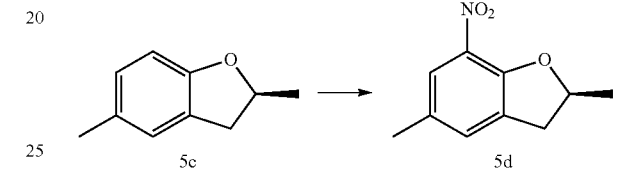

The title compound 5d was prepared according to the method for preparation of compound 3e of Example 3 by replacing 3d with 5c.

(S)-2,5-dimethyl-2,3-dihydrobenzofuran-7-amine (5e)

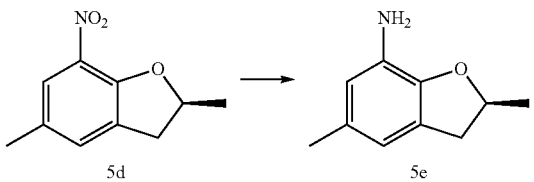

The title compound 5e was prepared according to the method for preparation of compound 3f of Example 3 by replacing 3e with 5d. MS-ESI (m/z): 164 (M+1)$^+$.

(S)-4-bromo-2,5-dimethyl-2,3-dihydrobenzofuran-7-amine (5f)

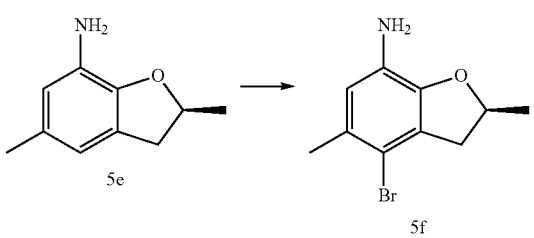

The title compound 5f was prepared according to the method for preparation of compound 3g of Example 3 by replacing 3f with 5e. MS-ESI (m/z): 242 (M+1)$^+$.

(S)-2,5-dimethyl-4-(pyridin-4-yl)-2,3-dihydrobenzo-furan-7-amine (5g)

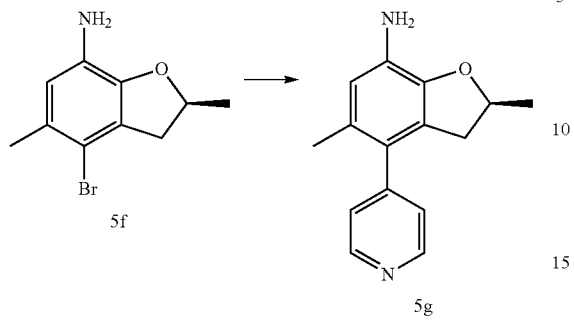

The title compound 5g was prepared according to the method for preparation of compound 3h of Example 3 by replacing 3g with 5f. MS-ESI (m/z): 241 (M+1)⁺.

(S)-2,5-dimethyl-4-(piperidin-4-yl)-2,3-dihydrobenzofuran-7-amine (5h)

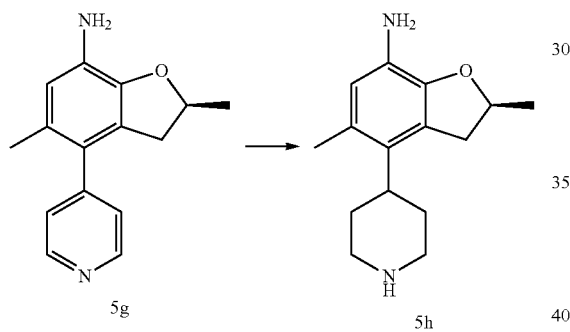

The title compound 5h was prepared according to the method for preparation of compound 3i of Example 3 by replacing 3h with 5g. MS-ESI (m/z): 247 (M+1)⁺.

(S)—N-6-(2,5-dimethyl-4-(piperidin-4-yl)-2,3-dihydrobenzofuran-7-yl)-N-4-(2-(isopropenylsulfonyl)phenyl)-3-methyl-1H-pyrazolo[3,4-d]pyrimidine-4,6-diamine (5)

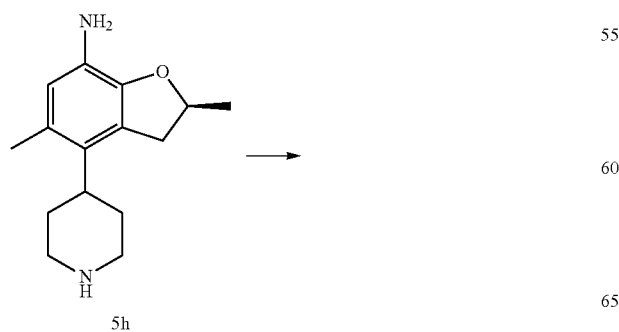

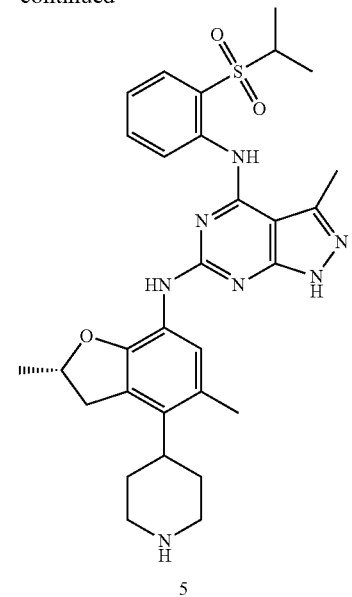

The title compound (5) was prepared according to the method for preparation of compound 3 of Example 3 by replacing 3i with 5h. MS-ESI (m/z): 576 (M+1)⁺.

Example 6

(S)—N-6-(2,5-dimethyl-4-(1-methylpiperidin-4-yl)-2,3-dihydrobenzofuran-7yl)-N-4-(2-(isopropylsulfonyl)phenyl)-3-methyl-1H-pyrazolo[3,4-d]pyrimidine-4,6-diamine (6)

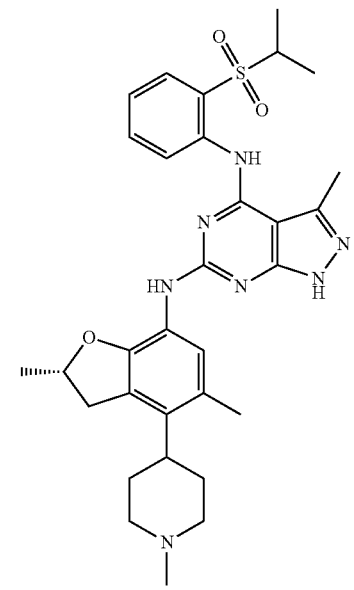

Prepared according to the method of Example 4 by replacing (R)—N-6-(2,5-dimethyl-4-(piperidin-4-yl)-2,3-dihydrobenzofuran-7-yl)-N-4-(2-(isopropylsulfonyl)phenyl)-3-methyl-1H-pyrazolo[3,4-d]pyrimidine-4,6-diamine (3) with (S)—N-6-(2,5-dimethyl-4-(piperidin-4-yl)-2,3-dihydrobenzofuran-7-yl)-N-4-(2-(isopropylsulfonyl)phenyl)-3-methyl-1H-pyrazolo[3,4-d]pyrimidine-4,6-diamine (5). The title compound (6) was obtained. MS-ESI (m/z): 590 (M+1)⁺.

Example 7

(7(4-(2-(isopropylsulfonyl)phenylamino)-3-methyl-1H-pyrazolo[3,4-d]pyrimidin-6-ylamino)-5-methyl-4-(piperidin-4-yl)-2,3-dihydrobenzofuran-2-yl)methanol (7)

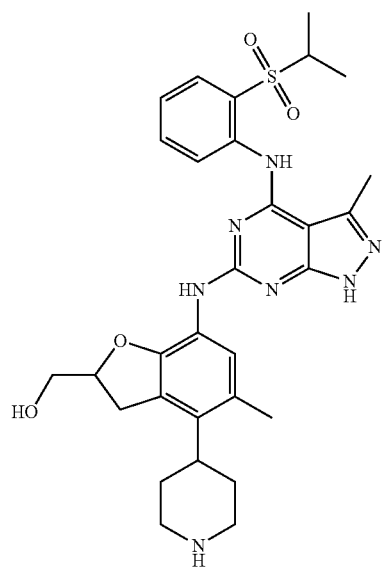

1-(allyloxy)-4-methyl-2-nitrobenzene (7a)

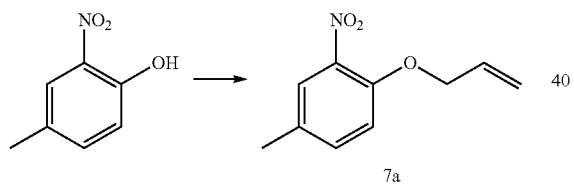

A mixture of 4-methyl-2-nitrophenol (5.0 g, 0.033 mol), 3-bromoprop-1-ene (4.2 g, 0.034 mol) and K₂CO₃ (4.6 g, 0.033 mol) in acetone (20 mL) was stirred for 8 h at ambient temperature. The mixture was poured into water (50 mL), extracted with EtOAc (90 mL), washed with brine, dried and concentrated to give the title compound (7a).

2-allyl-4-methyl-6-nitrophenol (7b)

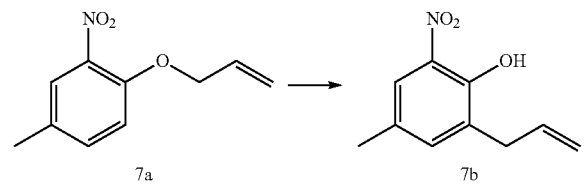

The compound 1-(allyloxy)-4-methyl-2-nitrobenzene (7a) (6.1 g, 0.032 mol) was stirred for 5 h at 200° C. The mixture was purified by column chromatography on silica gel eluting with hexanes/EtOAc (50:1) to give the title compound (7b) as a yellow oil.

(5-methyl-7-nitro-2,3-dihydrobenzofuran-2-yl)methanol (7c)

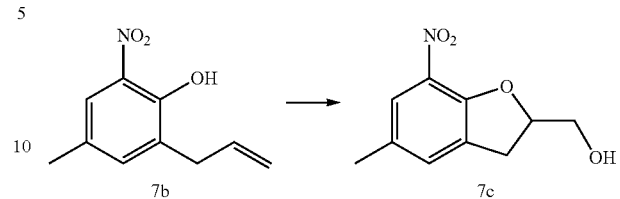

A mixture of 2-allyl-4-methyl-6-nitrophenol (7b) (0.50 g, 2.5 mmol) and m-CPBA (0.64 g, 2.5 mmol) in CHCl₃ (9 mL) was stirred for 6 h at 85° C. The mixture was poured into saturated NaHSO₃ (20 mL), extracted with DCM (40 mL), washed with brine, dried and concentrated. The residue was purified by column chromatography on silica gel eluting with hexanes/EtOAc (10:1) to give the title compound (7c) as a solid. MS-ESI (m/z): 210 (M+1)⁺.

(7-amino-5-methyl-2,3-dihydrobenzofuran-2-yl)methanol (7d)

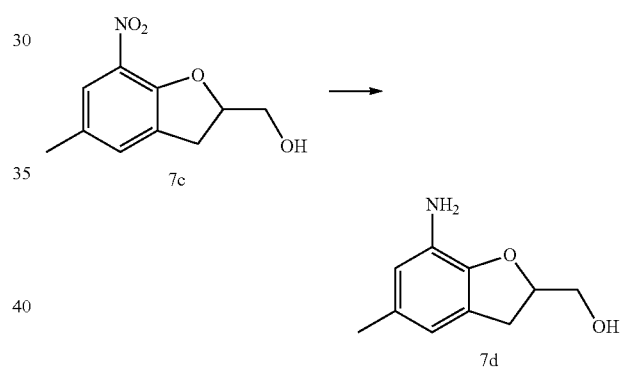

A mixture of (5-methyl-7-nitro-2,3-dihydrobenzofuran-2-yl)methanol (7c) (2.3 g, 0.011 mol) and Pd/C (230 mg, 10%) in THF (30 mL) was introduced H₂ and stirred at ambient temperature for 12 h. The mixture was filtered through celite and concentrated to give the title compound (7d) as a solid. MS-ESI (m/z): 180 (M+1)⁺.

(7-amino-4-bromo-5-methyl-2,3-dihydrobenzofuran-2-yl)methanol (7e)

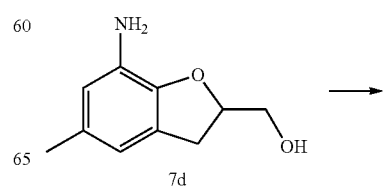

47

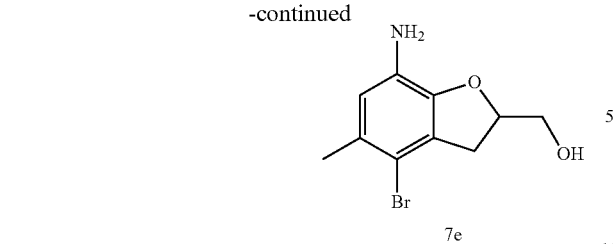

7e

To a mixture of (7-amino-5-methyl-2,3-dihydrobenzofuran-2-yl)methanol (7d) (0.80 g, 4.5 mmol) in DMF (13 mL) at 0° C. was added NBS (0.08 g, 4.5 mmol), it was stirred at 0° C. for 15 min. The mixture was extracted with EtOAc (150 mL), washed with NaHSO$_3$ (50 mL), water, brine, dried and concentrated to give the title compound (7e) as a yellow solid. MS-ESI (m/z): 258 (M+1)$^+$.

(7-amino-5-methyl-4-(pyridin-4-yl)-2,3-dihydrobenzofuran-2-yl)ethanol (7f)

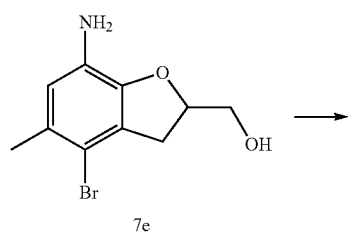

7e

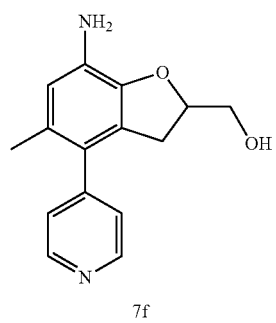

7f

A mixture of (7-amino-4-bromo-5-methyl-2,3-dihydrobenzofuran-2-yl)methanol (7e) (1.7 g, 6.6 mmol), pyridin-4-ylboronic acid (1.6 g, 1.3 mmol), Cs$_2$CO$_3$ (5.3 g, 16 mmol), Pd(PPh$_3$)$_4$ (0.76 g, 0.66 mmol) and water (13 mL) in DMF (60 mL) was stirred at 135° C. under N$_2$ for 1 h. It was cooled to ambient temperature, poured into water (100 mL), extracted with EtOAc (150 mL), washed with water, brine, dried and concentrated. The residue was purified by column chromatography on silica gel eluting with hexanes/EtOAc (20:1 to 5:1 to 1:1) to give the title compound (7f) as a yellow solid. MS-ESI (m/z): 257 (M+1)$^+$.

48

(7-amino-5-methyl-4-(piperidin-4-yl)-2,3-dihydrobenzofuran-2-yl)methanol (7g)

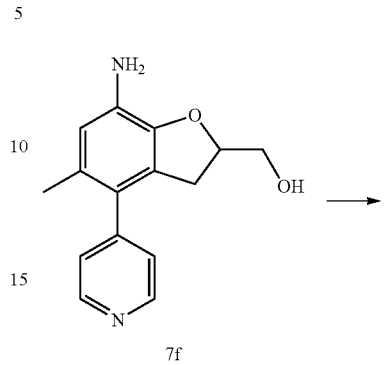

7f

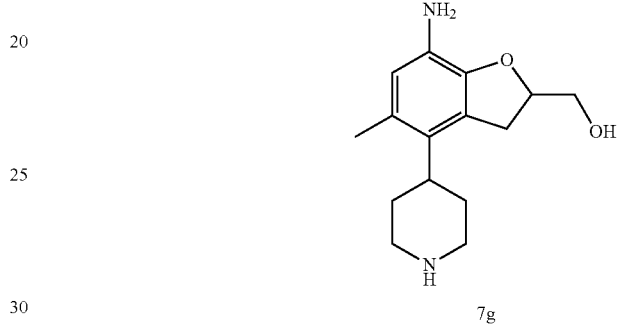

7g

A mixture of (7-amino-5-methyl-4-(pyridin-4-yl)-2,3-dihydrobenzofuran-2-yl)methanol (7f) (0.10 g, 0.39 mmol), PtO$_2$ (50 mg, 50%) and TEA (0.061 mL, 0.78 mmol) in HOAc (5 mL) was introduced H$_2$ and stirred at ambient temperature for 24 h (88 psi). The mixture was filtered, concentrated, and diluted with EtOAc (50 mL). A solution of ammonium hydroxide was added until pH=10, it was extracted with EtOAc (150 mL), washed with water, brine, dried and concentrated to give the title compound (7g) as a yellow oil. MS-ESI (m/z): 262 (M+1)$^+$.

(7-((4-f 2-(isopropylsulfonyl)phenyl)amino)-3-methyl-1H-pyrazolo[3,4-d]pyrimidin-6-yl)amino)-5-methyl-4-(piperidin-4-yl)-2,3-dihydrobenzofuran-2-yl)methanol (7)

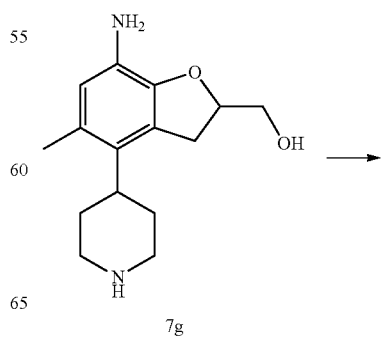

7g

-continued

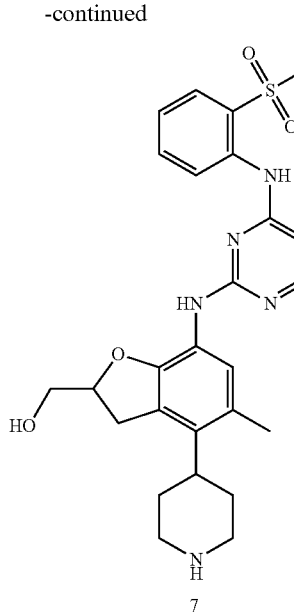

7

A mixture of (7-amino-5-methyl-4-(piperidin-4-yl)-2,3-dihydrobenzofuran-2-yl)methanol (7g) (40 mg, 0.15 mmol), N-(2-(isopropylsulfonyl)phenyl)-3-methyl-6-(methylsulfonyl)-1H-pyrazolo[3,4-d]pyrimidin-4-amine (Intermediate A) (75 mg, 0.18 mmol) and p-TsOH (29 mg, 0.15 mmol) in i-PrOH (0.5 mL) was stirred in a sealed tube at 160° C., for 5 h. The mixture was diluted with EtOAc (20 mL), ammonium hydroxide was added until pH=10, it was extracted with EtOAc (60 mL), washed with water, brine, dried and concentrated. The residue was purified by column chromatography on silica gel eluting with DCM/MeOH (10:1) to give the title compound (7) as a yellow solid. MS-ESI (m/z): 592 (M+1)⁺.

Example 8

N-4-(2-(isopropylsulfonyl)phenyl)-N-6-(2-(methoxymethyl)-5-methyl-4-(piperidin-4-yl)-2,3-dihydrobenzofuran-7-yl)-3-methyl-1H-pyrazolo[3,4-d]pyrimidine-4,6-diamine (8)

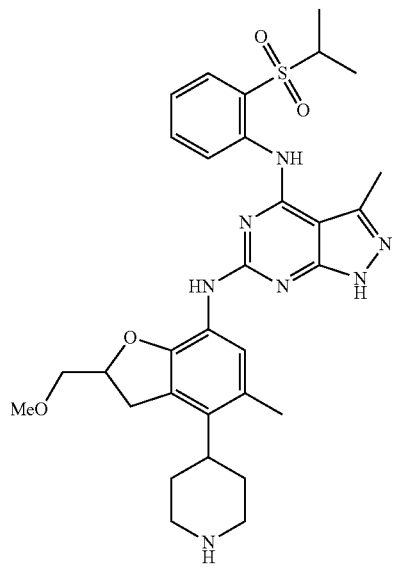

8

2-(methoxymethyl)-5-methyl-7-nitro-2,3-dihydrobenzofuran (8a)

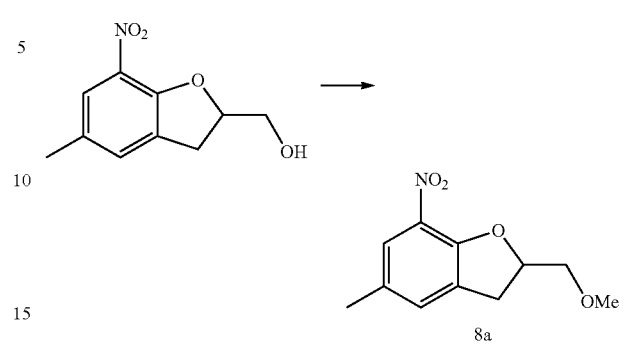

A mixture of (5-methyl-7-nitro-2,3-dihydrobenzofuran-2-yl)methanol (0.70 g, 3.3 mmol) in THF was cooled to 0° C. NaH was added to the mixture at 0° C. It was stirred for 15 min at 0° C. MeI was added dropwise to the mixture at 0° C. It was stirred for 0.5 h at 0° C. The mixture was poured into water (20 mL), extracted with EtOAc (40 mL), washed with water, brine, dried and concentrated to give the title compound (8a) as a yellow oil. MS-ESI (m/z): 224 (M+1)⁺.

2-(methoxymethyl)-5-methyl-2,3-dihydrobenzofuran-7-amine (8b)

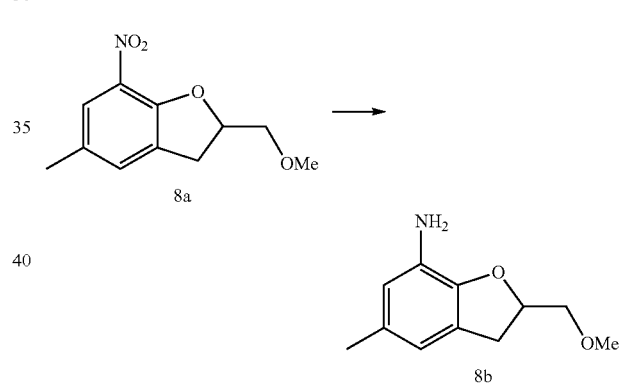

A mixture of 2-(methoxymethyl)-5-methyl-7-nitro-2,3-dihydrobenzofuran (8a) (0.85 g, 3.8 mmol) and Pd/C (90 mg, 10%) in THF (10 mL) was introduced H₂ and stirred at ambient temperature for 12 h. The mixture was filtered through celite and concentrated to give the title compound (8b) as oil. MS-ESI (m/z): 194 (M+1)⁺.

4-bromo-2-(methoxymethyl-5-methyl-2,3-dihydrobenzofuran-7-amine (8c)

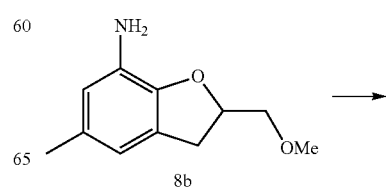

-continued

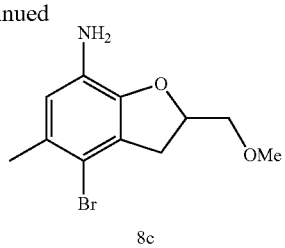

8c

To a mixture of 2-(methoxymethyl)-5-methyl-2,3-dihydrobenzofuran-7-amine (8b) (0.60 g, 3.1 mmol) in DMF (8 mL) at 0° C. was added NBS (0.55 g, 3.1 mmol). It was stirred at 0° C., for 15 min. The mixture was extracted with EtOAc (40 mL), washed with NaHSO₃ (20 mL), water, brine, dried and concentrated to give the title compound (8c) as a yellow oil. MS-ESI (m/z): 272 (M+1)⁺.

2-(methoxymethyl)-5-methyl-4-(pyridin-4-yl)-2,3-dihydrobenzofuran-7-amine (8d)

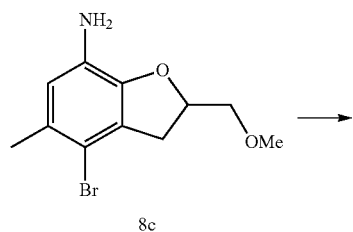

8c

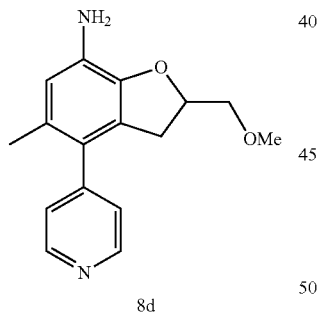

8d

A mixture of 4-bromo-2-(methoxymethyl)-5-methyl-2,3-dihydrobenzofuran-7-amine (8c) (0.85 g, 3.1 mmol), pyridin-4-ylboronic acid (0.76 g, 6.2 mmol), Cs₂CO₃ (2.5 g, 7.8 mmol), Pd(PPh₃)₄ (0.18 g, 0.16 mmol) and water (6 mL) in DMF (20 mL) was stirred at 135° C. under N₂ for 1 h. It was cooled to ambient temperature, poured into water (50 mL), extracted with EtOAc (60 mL), washed with water, brine, dried and concentrated. The residue was purified by column chromatography on silica gel eluting with hexanes/EtOAc (20:1 to 5:1 to 1:1) to give the title compound (8d) as a yellow oil. MS-ESI (m/z): 271 (M+1)⁺.

2-(methoxymethyl)-5-methyl-4-(piperidin-4-yl)-2,3-dihydrobenzofuran-7-amine (8e)

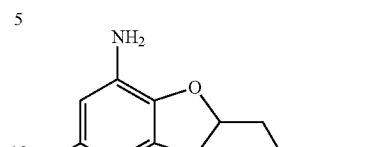

8d

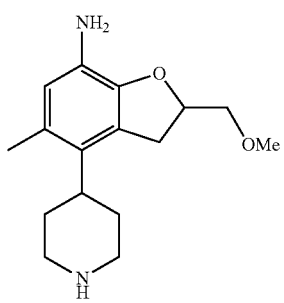

8e

A mixture of 2-(methoxymethyl)-5-methyl-4-(pyridin-4-yl)-2,3-dihydrobenzofuran-7-amine (8d) (0.57 g, 2.1 mmol), PtO₂ (300 mg, 50%) and TEA (0.323 mL, 4.20 mmol) in HOAc (15 mL) was introduced H₂ and stirred at ambient temperature for 24 h (88 psi). The mixture was filtered, concentrated, diluted with EtOAc (50 mL), a solution of ammonium hydroxide was added until pH=10. It was extracted with EtOAc (150 mL), washed with water, brine, dried and concentrated to give the title compound (5e) as a yellow oil. MS-ESI (m/z): 277 (M+1)⁺.

N-4-(2-(isopropylsulfonyl)phenyl)-N-6-(2-(methoxymethyl)-5-methyl-4-(piperidin-4-yl)-2,3-dihydrobenzofuran-7-yl)-3-methyl-1H-pyrazolo[3,4-d]pyrimidine-4,6-diamine (8)

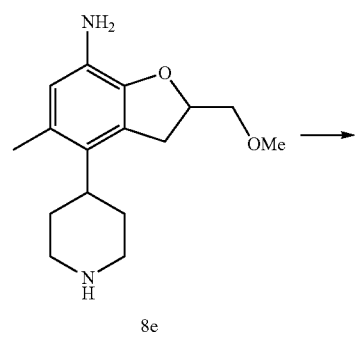

8e

53
-continued

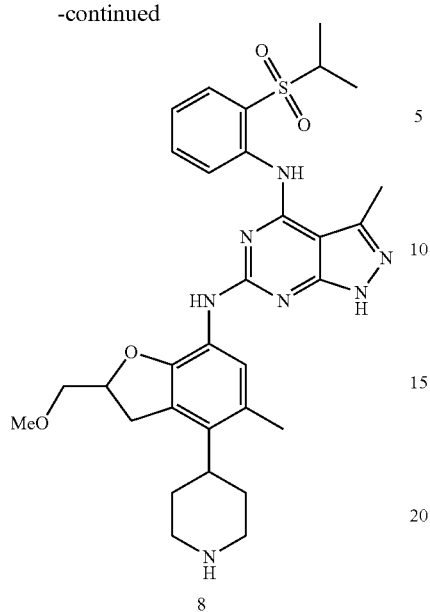

8

A mixture of (7-amino-5-methyl-4-(piperidin-4-yl)-2,3-dihydrobenzofuran-2-yl)methanol (5e) (100 mg, 0.36 mmol), N-(2-(isopropylsulfonyl)phenyl)-3-methyl-6-(methylsulfonyl)-1H-pyrazolo[3,4-d]pyrimidin-4-amine (Intermediate A) (163 mg, 0.400 mmol) and p-TsOH (69 mg, 0.36 mmol) in i-PrOH (0.5 mL) was stirred in a sealed tube at 160° C. for 5 h. The mixture was diluted with DCM (20 mL), ammonium hydroxide was added until pH=10, it was extracted with DCM (60 mL), washed with water, brine, dried and concentrated. The residue was purified by column chromatography on silica gel eluting with DCM/MeOH (10:1) to give the title compound (8) as a yellow solid. MS-ESI (m/z): 606 (M+1)$^+$.

Example 9

(R)-5-chloro-N-2-(2,5-dimethyl-4-(piperidin-4-yl)-2,3-dihydrobenzofuran-7-yl)-N-4-(2-(isopropylsulfonyl)phenyl)pyrimidine-2,4-diamine (9)

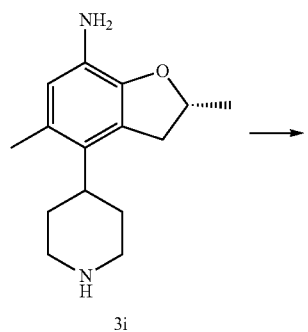

3i

54
-continued

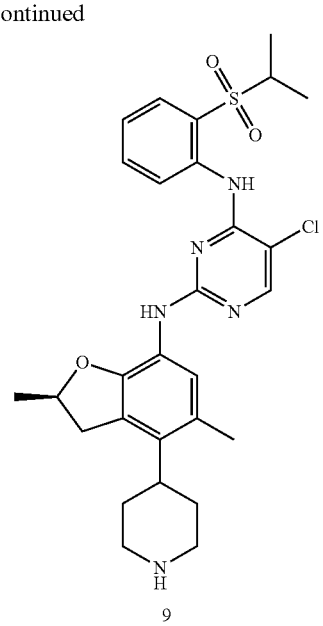

9

A mixture of 3i (0.8 g, 3.5 mmol), Intermediate B (1.32 g, 3.8 mmol) and TFA (1.0 g, 8.8 mmol) was stirred in a sealed tube at 130° C. for 5 h. The mixture was diluted with EtOAc (20 mL), washed with water, brine, dried and concentrated. The residue was purified by column chromatography on silica gel eluting with DCM/MeOH (10:1) to give the title compound (9) as a brown solid. MS-ESI (m/z): 556 (M+1)$^+$.

Example 10

(R)-5-chloro-N-2-(2,5-dimethyl-4-(1-methylpiperidin-4-yl)-2,3-dihydrobenzofuran-7-yl)-N-4-(2-(isopropylsulfonyl)phenyl)pyrimidine-2,4-diamine (10)

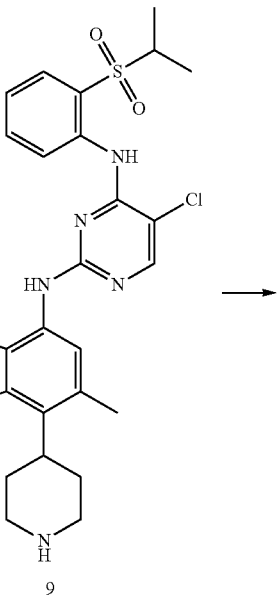

9

-continued

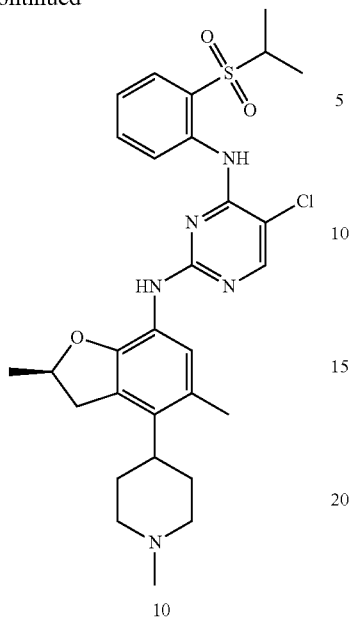

10

A mixture of Compound 9 (210 mg, 0.38 mmol), formaldehyde (11.4 mg, 0.38 mmol) and NaBH$_3$CN (57.3 mg, 0.91 mmol) was stirred at ambient temperature for 0.5 h. The mixture was diluted with NaHCO$_3$ (10 mL) and EtOAc (20 mL), extracted with EtOAc (60 mL), washed with water, brine, dried and concentrated. The residue was purified by column chromatography on silica gel eluting with DCM/MeOH (10:1) to give the title compound (10) as a yellow solid. MS-ESI (m/z): 570 (M+1)$^+$.

Example 11

(S)-5-chloro-N-2-(2,5-dimethyl-4-(piperidin-4-yl)-2,3-dihydrobenzofuran-7-yl)-N-4-(2-(isopropylsulfonyl)phenyl)pyrimidine-2,4-diamine (11)

Prepared according to the method of Example 9 by replacing 3i with 5h. The title compound (11) was obtained. MS-ESI (m/z): 556 (M+1)$^+$.

Example 12

(S)-5-chloro-N-2-(2,5-dimethyl-4-(1-methylpiperidin-4-yl)-2,3-dihydrobenzofuran-7-yl)-N-4-(2-(isopropylsulfonyl)phenyl)pyrimidine-2,4-diamine (12)

Prepared according to the method of Example 10 by replacing Compound 9 with Compound 11. The title compound (12) was obtained. MS-ESI (m/z): 570 (M+1)$^+$.

Example 13

5-chloro-N-4-(2-(isopropylsulfonyl)-N-2-(5-methyl-4-(piperidin-4-yl)-2,3-dihydrobenzofuran-7-yl)pyrimidine-2,4-diamine (13)

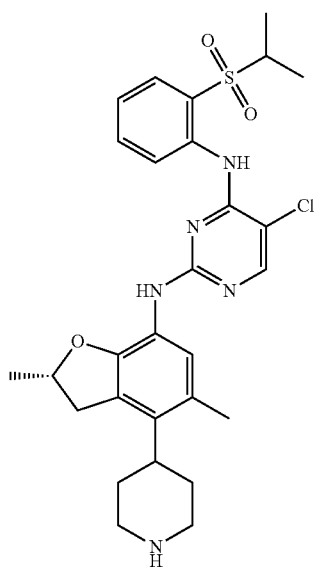
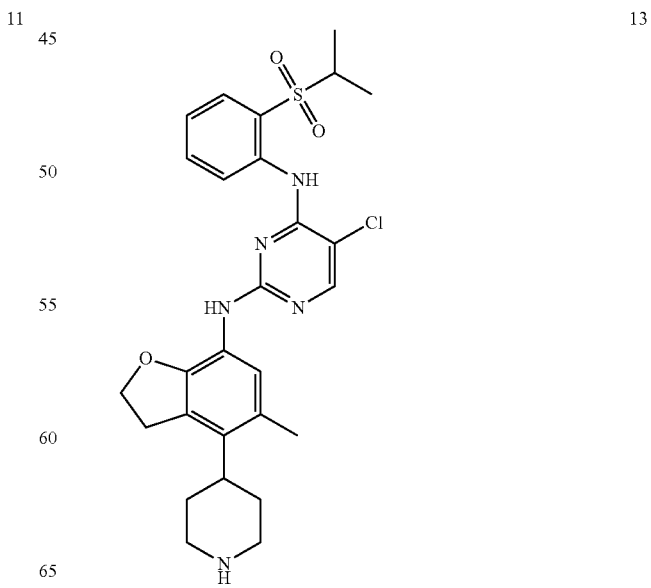

Prepared according to the method of Example 9 by replacing 3i with 5-methyl-4-(piperidin-4-yl)-2,3-dihydrobenzofuran-7-amine (1g). The title compound (13) was obtained. MS-ESI (m/z): 542 (M+1)+.

Example 14

5-chloro-N-4-(2-(isopropylsulfonyl)phenyl)-N-2-(5-methyl-4-(1-methylpiperidin-4-yl)-2,3-dihydrobenzofuran-7-yl)pyrimidine-2,4-diamine (14)

sulfonylation as shown the following scheme using conditions known in the art. The carbon marked with "*" has chirality as set forth in the chemical structures in Table 1.

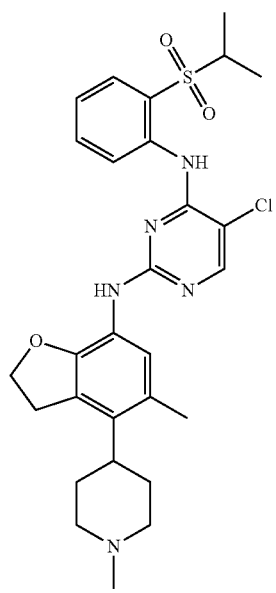

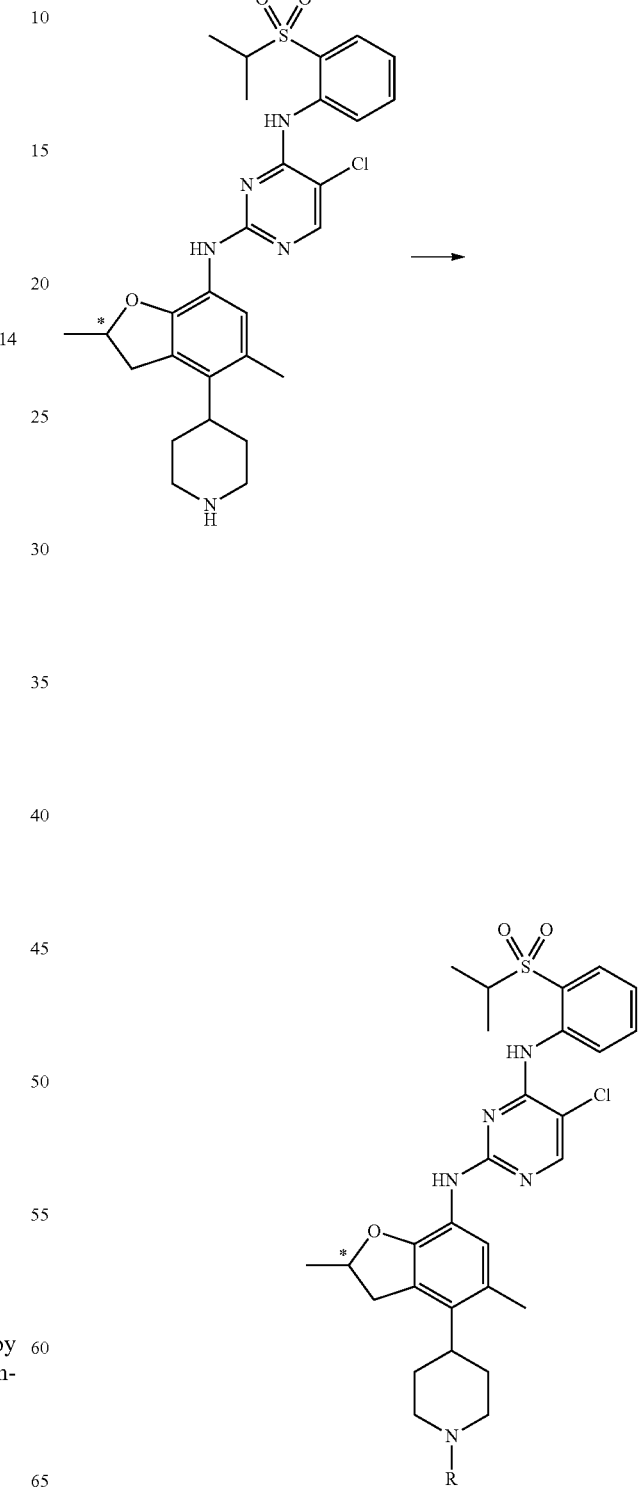

Prepared according to the method of Example 10 by replacing Compound 9 with Compound 13. The title compound (14) was obtained. MS-ESI (m/z): 556 (M+1)+.

Examples 15-58

Examples 15-58 (Table 1) were derivatized from Compound 9 or Compound 11 via N-alkylation, acylation, or

TABLE 1

| Example | Name | Structure | M + 1 |
|---|---|---|---|
| 15 | (S)-1-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)ethanone | 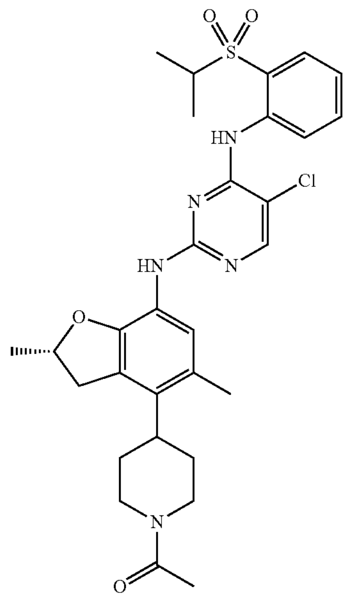 [SMILES: CC(=O)N1CCC(c2c(C)cc(Nc3ncc(Cl)c(Nc4ccccc4S(=O)(=O)C(C)C)n3)c3c2C[C@H](C)O3)CC1] | 598 |
| 16 | (R)-1-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)ethanone | 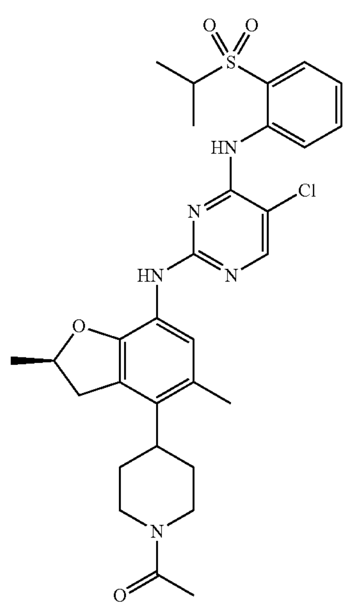 [SMILES: CC(=O)N1CCC(c2c(C)cc(Nc3ncc(Cl)c(Nc4ccccc4S(=O)(=O)C(C)C)n3)c3c2C[C@@H](C)O3)CC1] | 598 |

TABLE 1-continued

| Example | Name | Structure | M + 1 |
|---|---|---|---|
| 17 | (S)-5-chloro-N-2-(2,5-dimethyl-4-(1-(methylsulfonyl)piperidin-4-yl)-2,3-dihydrobenzofuran-7-yl)-N-4-(2-(isopropylsulfonyl)phenyl)pyrimidine-2,4-diamine | 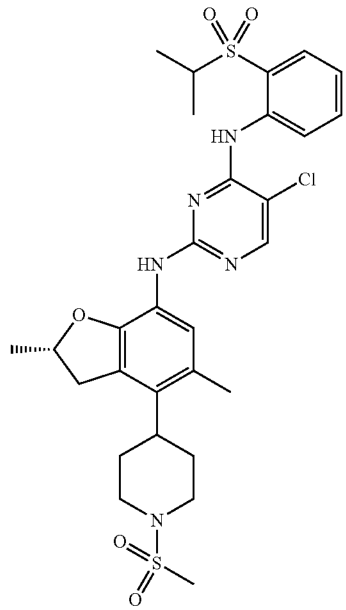 [SMILES: Cc1cc(Nc2ncc(Cl)c(Nc3ccccc3S(=O)(=O)C(C)C)n2)c2c(c1C1CCN(S(C)(=O)=O)CC1)C[C@H](C)O2] | 634 |
| 18 | (R)-5-chloro-N-2-(2,5-dimethyl-4-(1-(methylsulfonyl)piperidin-4-yl)-2,3-dihydrobenzofuran-7-yl)-N-4-(2-(isopropylsulfonyl)phenyl)pyrimidine-2,4-diamine | 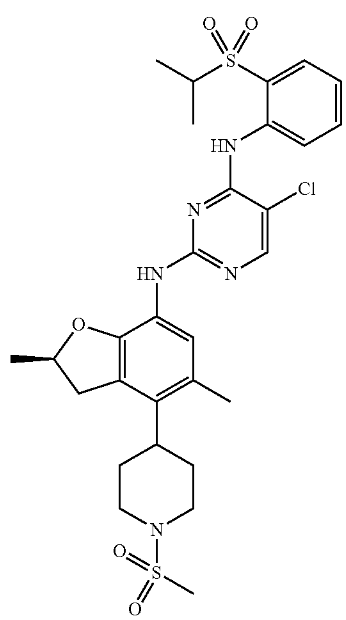 [SMILES: Cc1cc(Nc2ncc(Cl)c(Nc3ccccc3S(=O)(=O)C(C)C)n2)c2c(c1C1CCN(S(C)(=O)=O)CC1)C[C@@H](C)O2] | 634 |

TABLE 1-continued

| Example | Name | Structure | M + 1 |
|---|---|---|---|
| 19 | (S)-2-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)acetic acid | 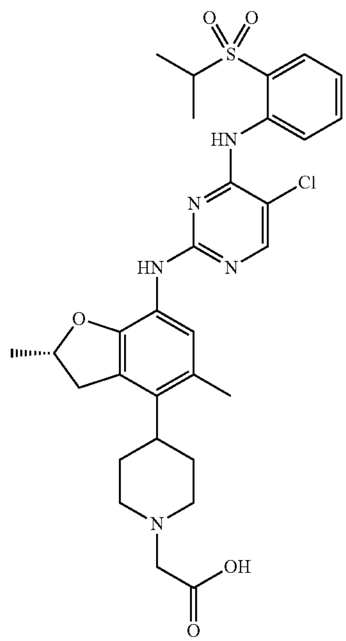 [SMILES: Cc1cc(Nc2ncc(Cl)c(Nc3ccccc3S(=O)(=O)C(C)C)n2)c2c(c1C1CCN(CC(=O)O)CC1)C[C@H](C)O2] | 614 |
| 20 | (R)-2-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)acetic acid | 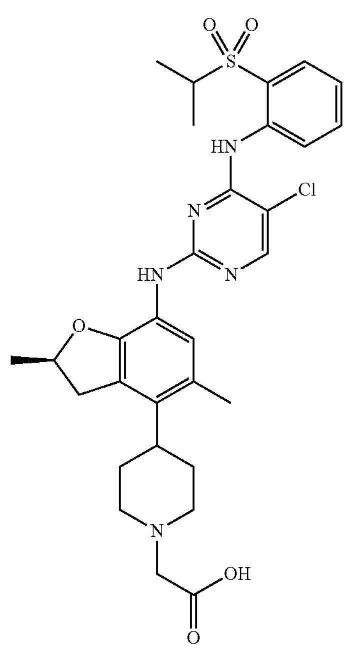 [SMILES: Cc1cc(Nc2ncc(Cl)c(Nc3ccccc3S(=O)(=O)C(C)C)n2)c2c(c1C1CCN(CC(=O)O)CC1)C[C@@H](C)O2] | 614 |

TABLE 1-continued

| Example | Name | Structure | M + 1 |
|---------|------|-----------|-------|
| 21 | (S)-2-amino-1-(4-((S)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)propan-1-one | 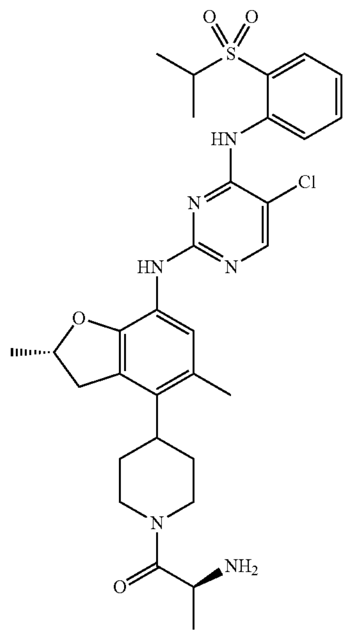 [SMILES: Cc1cc(Nc2ncc(Cl)c(Nc3ccccc3S(=O)(=O)C(C)C)n2)c2c(c1C1CCN(C(=O)[C@H](C)N)CC1)C[C@H](C)O2] | 627 |
| 22 | (S)-2-amino-1-(4-((R)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)propan-1-one | 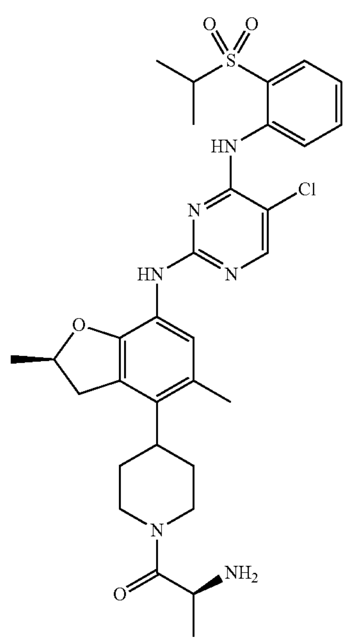 [SMILES: Cc1cc(Nc2ncc(Cl)c(Nc3ccccc3S(=O)(=O)C(C)C)n2)c2c(c1C1CCN(C(=O)[C@H](C)N)CC1)C[C@@H](C)O2] | 627 |

TABLE 1-continued

| Example | Name | Structure | M + 1 |
|---------|------|-----------|-------|
| 23 | (R)-1-(4-((R)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)propan-2-ol | 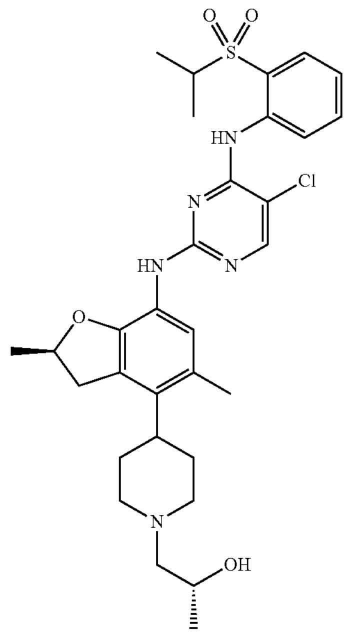 [SMILES: Cc1cc(Nc2ncc(Cl)c(Nc3ccccc3S(=O)(=O)C(C)C)n2)c2c(c1C1CCN(C[C@@H](C)O)CC1)C[C@@H](C)O2] | 614 |
| 24 | (S)-1-(4-((R)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)propan-2-ol | 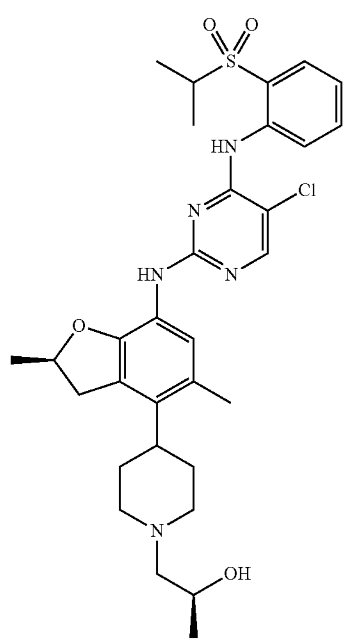 [SMILES: Cc1cc(Nc2ncc(Cl)c(Nc3ccccc3S(=O)(=O)C(C)C)n2)c2c(c1C1CCN(C[C@H](C)O)CC1)C[C@@H](C)O2] | 614 |

TABLE 1-continued

| Example | Name | Structure | M + 1 |
|---|---|---|---|
| 25 | (S)-2-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)acetamide | 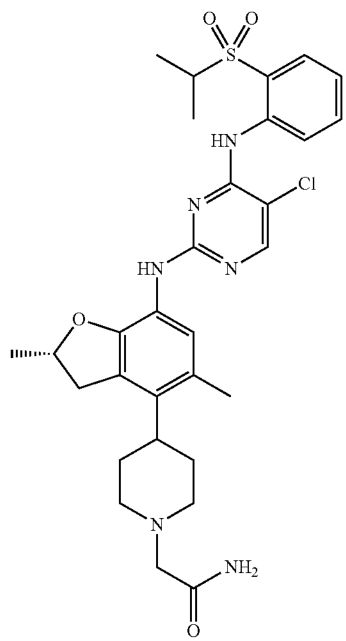 [SMILES: Cc1cc(Nc2ncc(Cl)c(Nc3ccccc3S(=O)(=O)C(C)C)n2)c2c(c1C1CCN(CC(N)=O)CC1)C[C@H](C)O2] | 613 |
| 26 | (R)-2-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)acetamide | 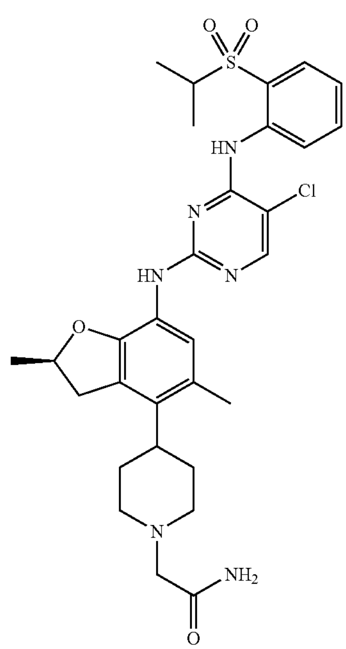 [SMILES: Cc1cc(Nc2ncc(Cl)c(Nc3ccccc3S(=O)(=O)C(C)C)n2)c2c(c1C1CCN(CC(N)=O)CC1)C[C@@H](C)O2] | 613 |

TABLE 1-continued

| Example | Name | Structure | M + 1 |
|---|---|---|---|
| 27 | (S)-2-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-N,N-dimethylacetamide | 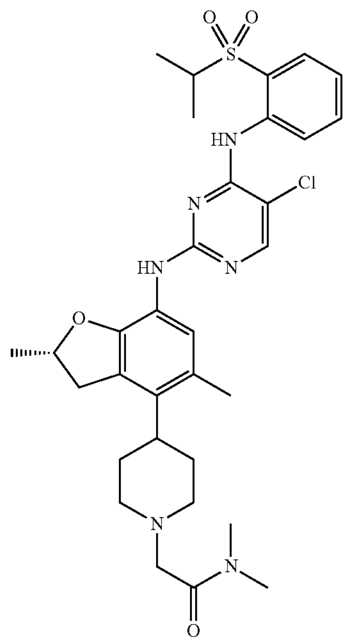 [SMILES: Cc1cc(Nc2ncc(Cl)c(Nc3ccccc3S(=O)(=O)C(C)C)n2)c2c(c1C1CCN(CC(=O)N(C)C)CC1)C[C@H](C)O2] | 641 |
| 28 | (R)-2-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-N,N-dimethylacetamide | 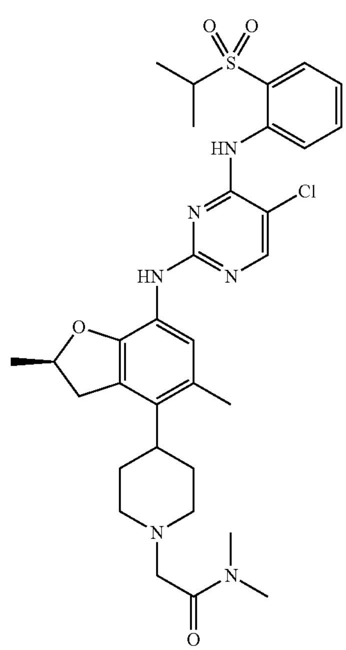 [SMILES: Cc1cc(Nc2ncc(Cl)c(Nc3ccccc3S(=O)(=O)C(C)C)n2)c2c(c1C1CCN(CC(=O)N(C)C)CC1)C[C@@H](C)O2] | 641 |

TABLE 1-continued

| Example | Name | Structure | M + 1 |
|---------|------|-----------|-------|
| 29 | (S)-5-chloro-N-2-(2,5-dimethyl-4-(1-(2-(methylsulfonyl)ethyl)piperidin-4-yl)-2,3-dihydrobenzofuran-7-yl)-N-4-(2-(isopropylsulfonyl)phenyl)pyrimidine-2,4-diamine | 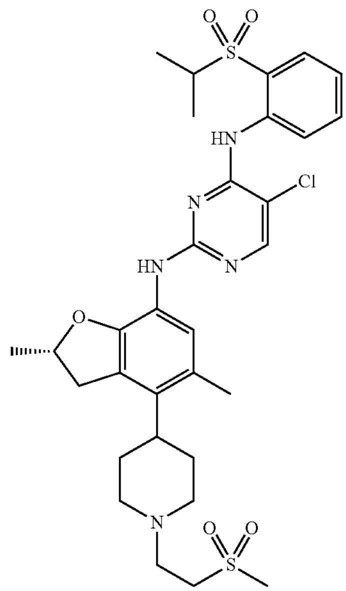 [SMILES: Cc1cc(Nc2ncc(Cl)c(Nc3ccccc3S(=O)(=O)C(C)C)n2)c2c(c1C1CCN(CCS(C)(=O)=O)CC1)C[C@H](C)O2] | 662 |
| 30 | (R)-5-chloro-N-2-(2,5-dimethyl-4-(1-(2-(methylsulfanyl)ethyl)piperidin-4-yl)-2,3-dihydrobenzofuran-7-yl)-N-4-(2-(isopropylsulfonyl)phenyl)pyrimidine-2,4-diamine | 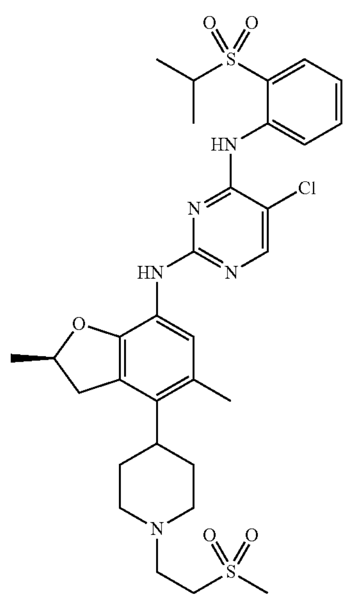 [SMILES: Cc1cc(Nc2ncc(Cl)c(Nc3ccccc3S(=O)(=O)C(C)C)n2)c2c(c1C1CCN(CCS(C)(=O)=O)CC1)C[C@@H](C)O2] | 662 |

TABLE 1-continued
| Example | Name | Structure | M + 1 |
|---|---|---|---|
| 31 | (S)-5-chloro-N-4-(2-(isopropylsulfonyl)phenyl)-N-2-(4-(1-(2-methoxyethyl)piperidin-4-yl)-2,5-dimethyl-2,3-dihydrobenzofuran-7-yl)pyrimidine-2,4-diamine | 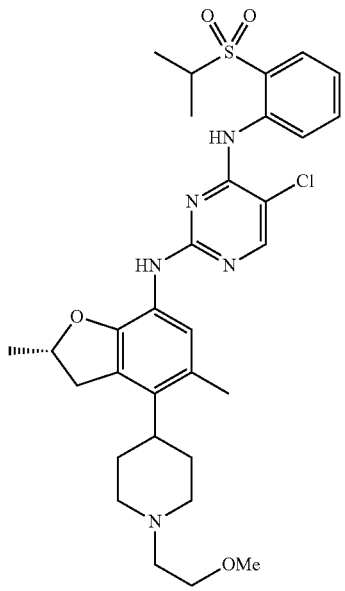 [SMILES: COCCN1CCC(c2c(C)cc(Nc3ncc(Cl)c(Nc4ccccc4S(=O)(=O)C(C)C)n3)c3c2C[C@H](C)O3)CC1] | 614 |
| 32 | (R)-5-chloro-N-4-(2-(isopropylsulfonyl)phenyl)-N-2-(4-(1-(2-methoxyethyl)piperidin-4-yl)-2,5-dimethyl-2,3-dihydrobenzofuran-7-yl)pyrimidine-2,4-diamine | 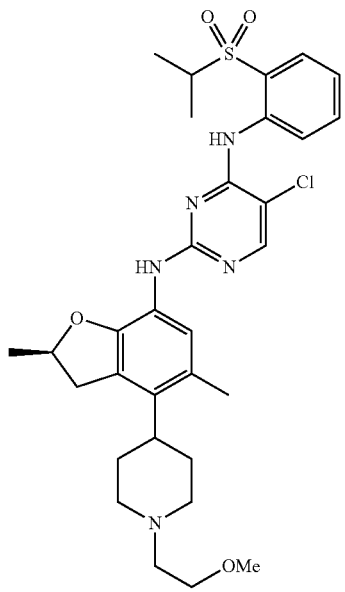 [SMILES: COCCN1CCC(c2c(C)cc(Nc3ncc(Cl)c(Nc4ccccc4S(=O)(=O)C(C)C)n3)c3c2C[C@@H](C)O3)CC1] | 614 |

TABLE 1-continued

| Example | Name | Structure | M + 1 |
|---|---|---|---|
| 33 | (R)-2-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)ethanol | 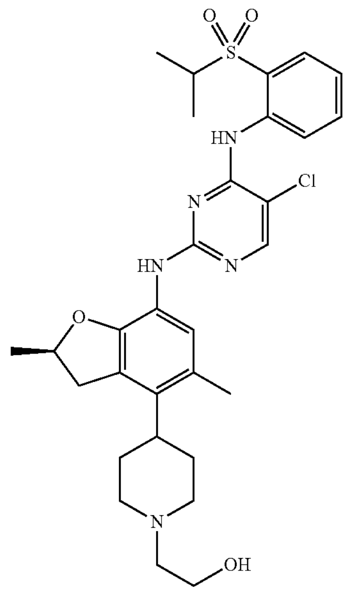 [SMILES: Cc1cc(Nc2ncc(Cl)c(Nc3ccccc3S(=O)(=O)C(C)C)n2)c2c(c1C1CCN(CCO)CC1)C[C@@H](C)O2] | 600 |
| 34 | (S)-2-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)ethanol | 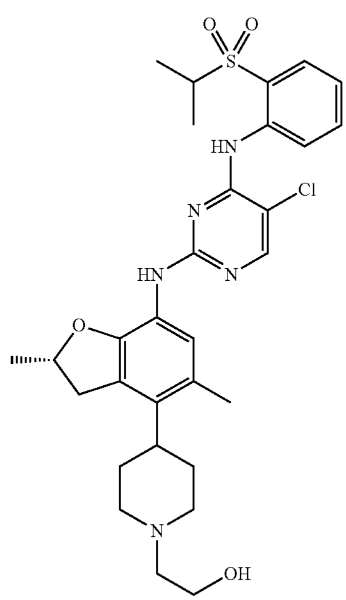 [SMILES: Cc1cc(Nc2ncc(Cl)c(Nc3ccccc3S(=O)(=O)C(C)C)n2)c2c(c1C1CCN(CCO)CC1)C[C@H](C)O2] | 600 |

TABLE 1-continued

| Example | Name | Structure | M + 1 |
|---------|------|-----------|-------|
| 35 | (R)-1-(4-((S)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)propan-2-ol | 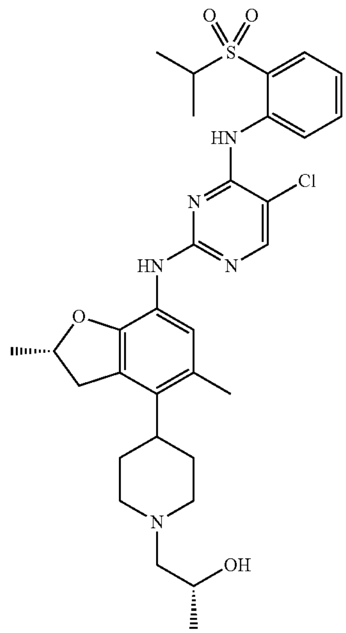 [SMILES: Cc1cc(Nc2ncc(Cl)c(Nc3ccccc3S(=O)(=O)C(C)C)n2)c2c(c1C1CCN(C[C@@H](C)O)CC1)C[C@H](C)O2] | 614 |
| 36 | (S)-1-(4-((S)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)propan-2-ol | 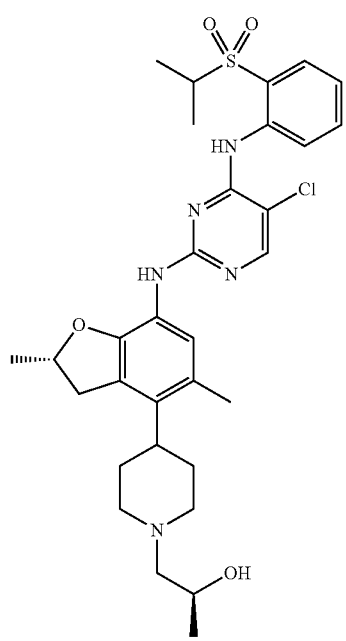 [SMILES: Cc1cc(Nc2ncc(Cl)c(Nc3ccccc3S(=O)(=O)C(C)C)n2)c2c(c1C1CCN(C[C@H](C)O)CC1)C[C@H](C)O2] | 614 |

TABLE 1-continued

| Example | Name | Structure | M + 1 |
|---|---|---|---|
| 37 | (R)-1-(4-(7-((5-chloro-4-((2-isopropylsulfonyl)phenyl)amino)pyrimidin-2-yl)amino)-2,5-dimethyl-2,3-dihydrobenzofuran-4-yl)piperidin-1-yl)-2-hydroxyethanone | 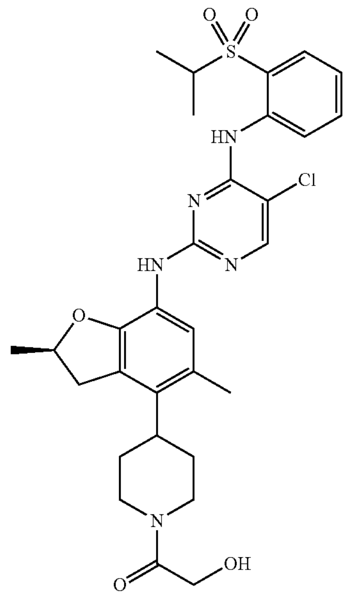 [SMILES: Cc1cc(Nc2ncc(Cl)c(Nc3ccccc3S(=O)(=O)C(C)C)n2)c2c(c1C1CCN(C(=O)CO)CC1)C[C@@H](C)O2] | 614 |
| 38 | (S)-1-(4-((R)-7-((5-chloro-4-((2-isopropylsulfonyl)phenyl)amino)pyrimidin-2-yl)amino)-2,5-dimethyl-2,3-dihydrobenzofuran-4-yl)piperidin-1-yl)-2-hydroxypropan-1-one | 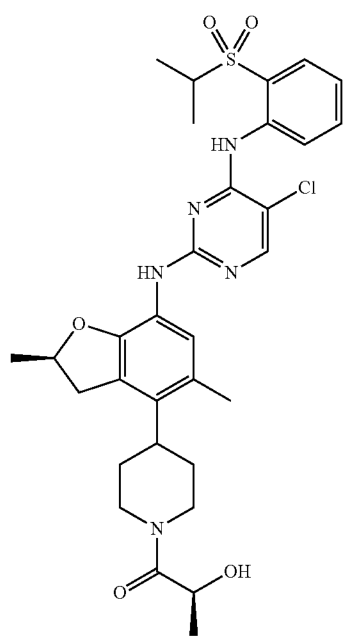 [SMILES: Cc1cc(Nc2ncc(Cl)c(Nc3ccccc3S(=O)(=O)C(C)C)n2)c2c(c1C1CCN(C(=O)[C@H](C)O)CC1)C[C@@H](C)O2] | 628 |

TABLE 1-continued

| Example | Name | Structure | M + 1 |
|---|---|---|---|
| 39 | (R)-1-(4-((R)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-2-hydroxypropan-1-one | 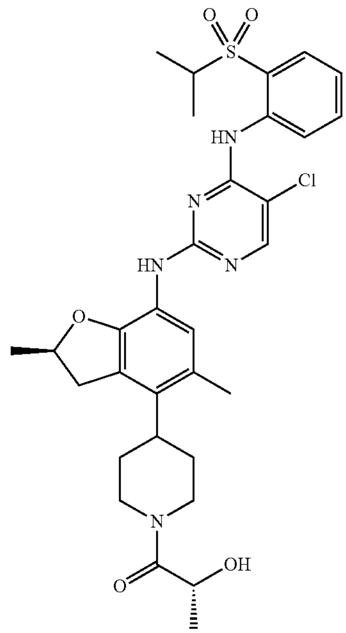 [SMILES: Cc1cc(Nc2ncc(Cl)c(Nc3ccccc3S(=O)(=O)C(C)C)n2)c2c(c1C1CCN(C(=O)[C@@H](C)O)CC1)C[C@@H](C)O2] | 628 |
| 40 | (S)-methyl 4-(7-((5-chloro-4-((2-(isopropylsulfonyl)phenyl)amino)pyrimidin-2-yl)amino)-2,5-dimethyl-2,3-dihydrobenzofuran-4-yl)piperidine-1-carboxylate | 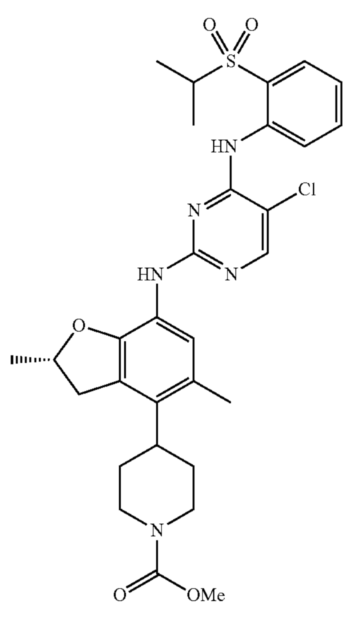 [SMILES: COC(=O)N1CCC(c2c(C)cc(Nc3ncc(Cl)c(Nc4ccccc4S(=O)(=O)C(C)C)n3)c3c2C[C@H](C)O3)CC1] | 614 |

TABLE 1-continued

| Example | Name | Structure | M + 1 |
|---|---|---|---|
| 41 | (S)-ethyl 2-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)acetate | 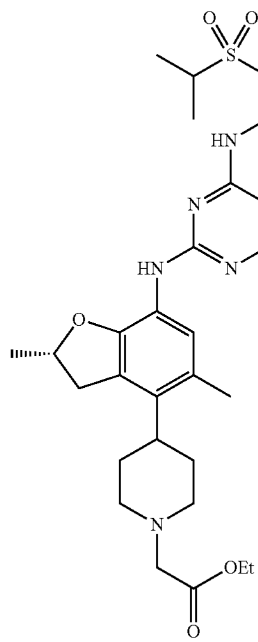 | 642 |
| 42 | (S)-2-amino-1-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)ethanone | 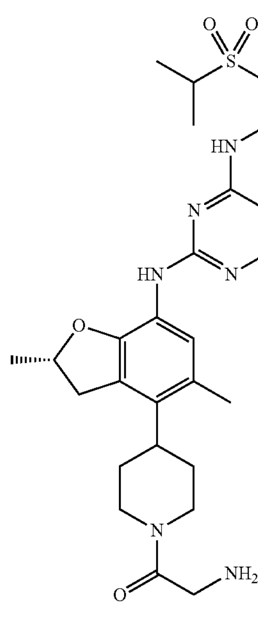 | 613 |

TABLE 1-continued
| Example | Name | Structure | M + 1 |
|---------|------|-----------|-------|
| 43 | (S)-4-(7-((5-chloro-4-((2-(isopropylsulfonyl)phenyl)amino)pyrimidin-2-yl)amino)-2,5-dimethyl-2,3-dihydrobenzofuran-4-yl)piperidine-1-carboxamide | 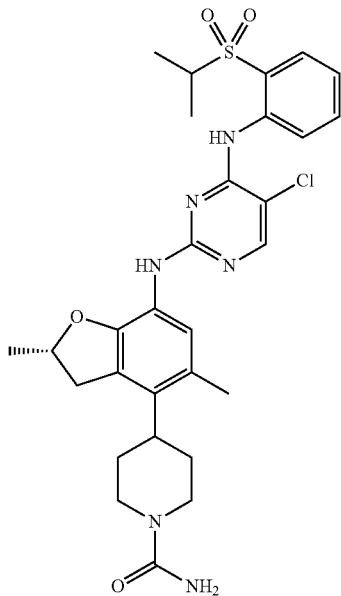 [SMILES: Cc1cc(Nc2ncc(Cl)c(Nc3ccccc3S(=O)(=O)C(C)C)n2)c2c(c1C1CCN(C(N)=O)CC1)C[C@H](C)O2] | 599 |
| 44 | (S)-1-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-2-(methylamino)ethanone | 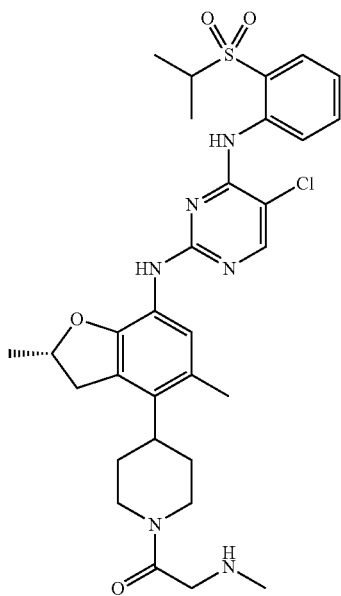 [SMILES: CNCC(=O)N1CCC(c2c(C)cc(Nc3ncc(Cl)c(Nc4ccccc4S(=O)(=O)C(C)C)n3)c3c2C[C@H](C)O3)CC1] | 627 |

TABLE 1-continued

| Example | Name | Structure | M + 1 |
|---------|------|-----------|-------|
| 45 | (S)-1-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-2-(dimethylamino)ethanone | 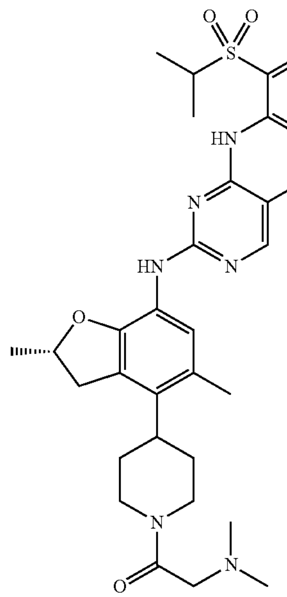 | 641 |
| 46 | (S)-(7-((5-chloro-4-((2-(isopropylsulfonyl)phenyl)amino)pyrimidin-2-yl)amino)-2,5-dimethyl-2,3-dihydrobenzofuran-4-yl)(piperazin-1-yl)methanone | 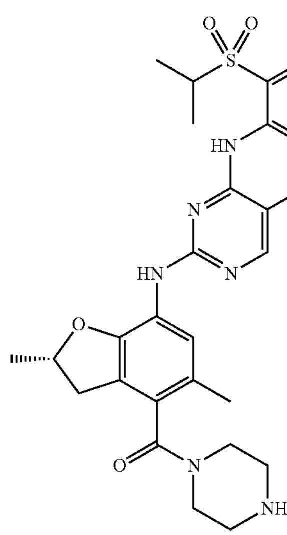 | 585 |

TABLE 1-continued

| Example | Name | Structure | M + 1 |
|---|---|---|---|
| 47 | (S)-(7-((5-chloro-4-((2-(isopropylsulfonyl)phenyl)amino)pyrimidin-2-yl)amino)-2,5-dimethyl-2,3-dihydrobenzofuran-4-yl)(4-methylpiperazin-1-yl)methanone | 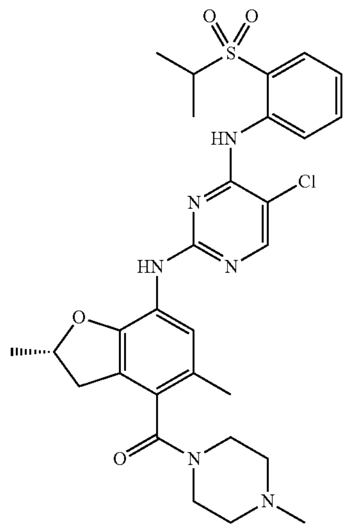 [SMILES: Cc1cc(Nc2ncc(Cl)c(Nc3ccccc3S(=O)(=O)C(C)C)n2)c2c(c1C(=O)N1CCN(C)CC1)C[C@H](C)O2] | 599 |
| 48 | (S)-(7-((5-chloro-4-((2-(isopropylsulfonyl)phenyl)amino)pyrimidin-2-yl)amino)-2,5-dimethyl-2,3-dihydrobenzofuran-4-yl)(morpholino)methanone | 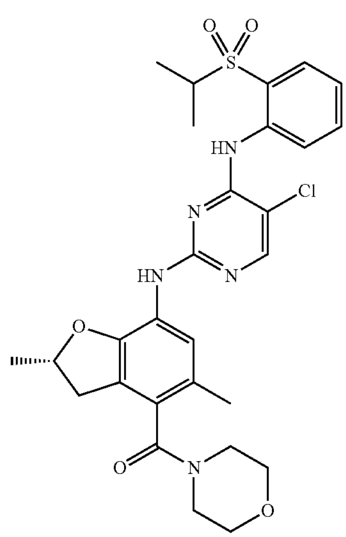 [SMILES: Cc1cc(Nc2ncc(Cl)c(Nc3ccccc3S(=O)(=O)C(C)C)n2)c2c(c1C(=O)N1CCOCC1)C[C@H](C)O2] | 586 |

TABLE 1-continued

| Example | Name | Structure | M + 1 |
|---|---|---|---|
| 49 | (R)-1-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)propan-1-one | 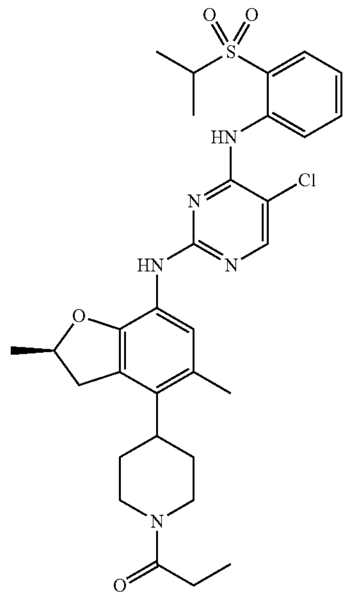 [SMILES: CCC(=O)N1CCC(c2c(C)cc(Nc3ncc(Cl)c(Nc4ccccc4S(=O)(=O)C(C)C)n3)c3c2C[C@@H](C)O3)CC1] | 612 |
| 50 | (R)-1-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-2-methylpropan-1-one | 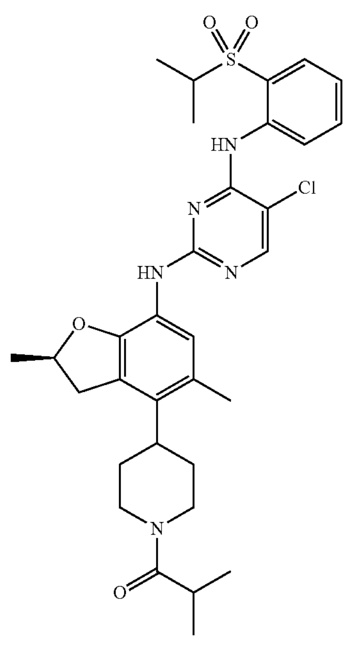 [SMILES: Cc1cc(Nc2ncc(Cl)c(Nc3ccccc3S(=O)(=O)C(C)C)n2)c2c(c1C1CCN(C(=O)C(C)C)CC1)C[C@@H](C)O2] | 626 |

TABLE 1-continued

| Example | Name | Structure | M + 1 |
|---|---|---|---|
| 51 | (R)-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)(cyclopropyl)methanone | 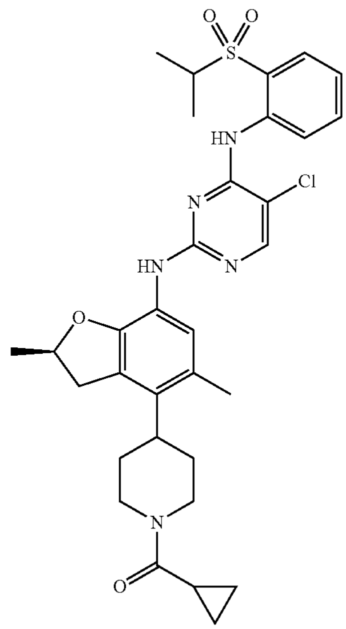 [SMILES: Cc1cc(Nc2ncc(Cl)c(Nc3ccccc3S(=O)(=O)C(C)C)n2)c2c(c1C1CCN(C(=O)C3CC3)CC1)C[C@@H](C)O2] | 624 |
| 52 | (R)-5-chloro-N-2-(4-(1-(ethylsulfonyl)piperidin-4-yl)-2,5-dimethyl-2,3-dihydrobenzofuran-7-yl)-N-4-(2-(isopropylsulfonyl)phenyl)pyrimidine-2,4-diamine | 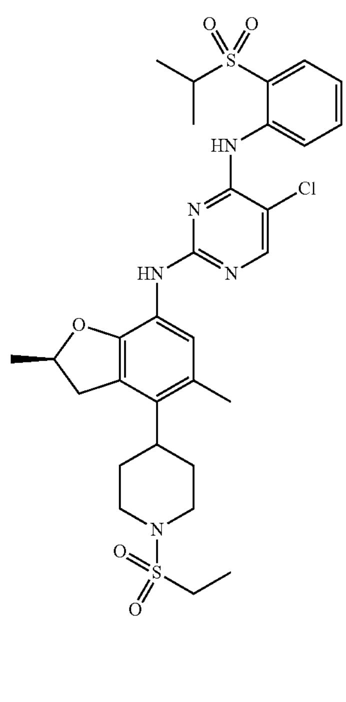 [SMILES: CCS(=O)(=O)N1CCC(c2c(C)cc(Nc3ncc(Cl)c(Nc4ccccc4S(=O)(=O)C(C)C)n3)c3c2C[C@@H](C)O3)CC1] | 648 |

TABLE 1-continued

| Example | Name | Structure | M + 1 |
|---------|------|-----------|-------|
| 53 | (R)-5-chloro-N-4-(2-(isopropylsulfonyl)phenyl)-N-2-(4-(1-(isopropylsulfonyl)piperidin-4-yl)-2,5-dimethyl-2,3-dihydrobenzofuran-7-yl)pyrimidine-2,4-diamine | 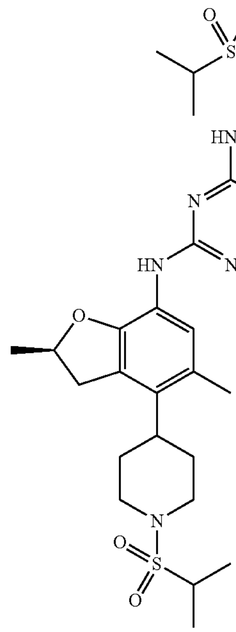 | 662 |
| 54 | (R)-5-chloro-N-2-(4-(1-(cyclopropylsulfonyl)piperidin-4-yl)-2,5-dimethyl-2,3-dihydrobenzofuran-7-yl)-N-4-(2-(isopropylsulfonyl)phenyl)pyrimidine-2,4-diamine | 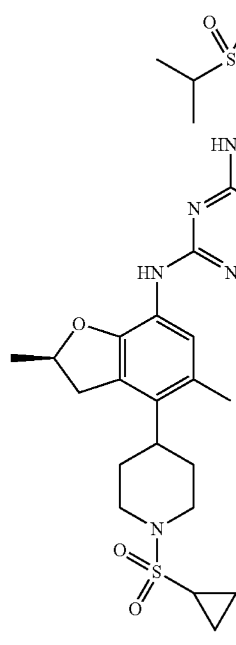 | 660 |

TABLE 1-continued

| Example | Name | Structure | M + 1 |
|---|---|---|---|
| 55 | (R)-1-(4-((S)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-2-methoxypropan-1-one | 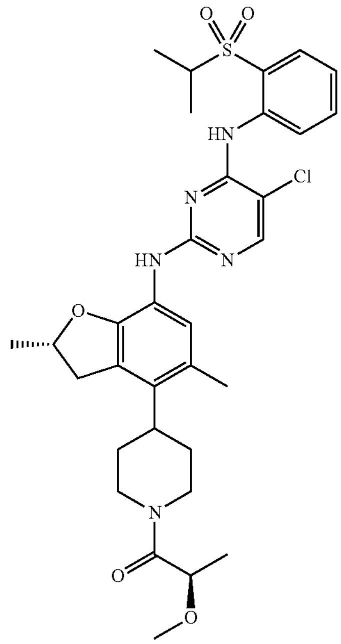 [SMILES: CO[C@H](C)C(=O)N1CCC(c2c(C)cc(Nc3ncc(Cl)c(Nc4ccccc4S(=O)(=O)C(C)C)n3)c3c2C[C@H](C)O3)CC1] | 642 |
| 56 | (R)-1-(4-((R)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-2-methoxypropan-1-one | 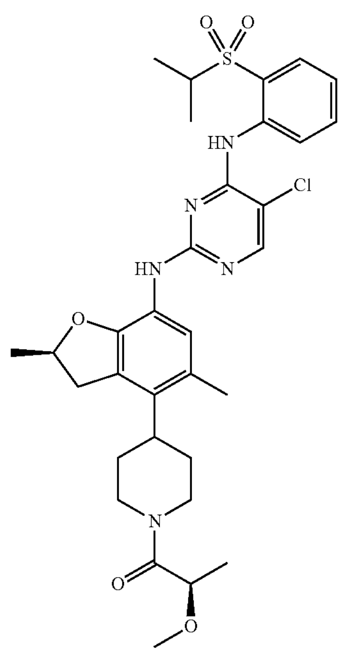 [SMILES: CO[C@H](C)C(=O)N1CCC(c2c(C)cc(Nc3ncc(Cl)c(Nc4ccccc4S(=O)(=O)C(C)C)n3)c3c2C[C@@H](C)O3)CC1] | 642 |

TABLE 1-continued

| Example | Name | Structure | M + 1 |
|---|---|---|---|
| 57 | (S)-1-(4-((R)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-2-methoxypropan-1-one | 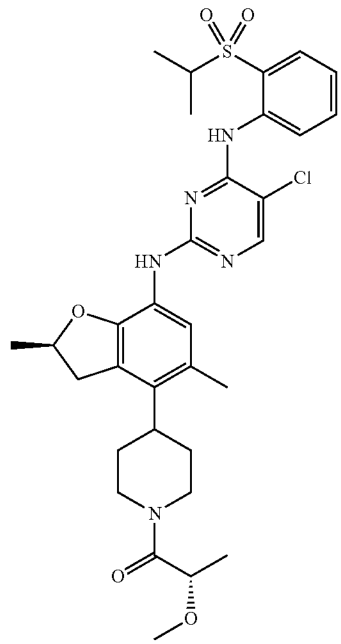 [SMILES: CO[C@@H](C)C(=O)N1CCC(c2c(C)cc(Nc3ncc(Cl)c(Nc4ccccc4S(=O)(=O)C(C)C)n3)c3c2C[C@@H](C)O3)CC1] | 642 |
| 58 | (S)-1-(4-((S)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-2-methoxypropan-1-one | 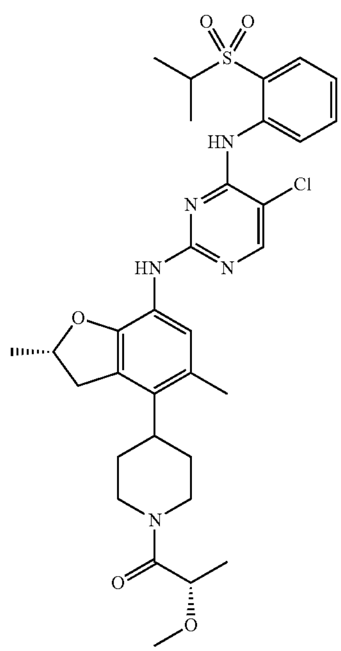 [SMILES: CO[C@@H](C)C(=O)N1CCC(c2c(C)cc(Nc3ncc(Cl)c(Nc4ccccc4S(=O)(=O)C(C)C)n3)c3c2C[C@H](C)O3)CC1] | 642 |

Biological Activity

Inhibition Activity of Cell Proliferation

SU-DHL-1 cells were seeded in 96-well tissue culture plates. On the next day, cells were exposed to various concentrations of compounds and further cultured for 72 h. Cell proliferation was then determined using Cell Counting Kit-8 [(CCK-8), Dojindo] assay. Briefly, add 10 µL of the CCK-8 solution to each well of the plate. Incubate the plate for 1-4 hours in the incubator. Measure the absorbance at 450 nm using a multi-well spectrophotometer (SpectraMAX 190, Molecular Devices). The inhibition rate (%) was calculated using the following equation: [1-(A450 Compound/A450 Control)]×100%. $IC_{50}$ values were calculated according to inhibition curve by four-parameter fit.

Biological Data for Select Compounds

Select compounds prepared as described above were assayed according to the biological procedures described herein. The results are given in the table 2.

TABLE 2

| Example | SU-DHL-1 IC$_{50}$ (nM) |
|---|---|
| 1 | 25.5 |
| 2 | 18.9 |
| 3 | 61.0 |
| 4 | 10.9 |
| 5 | 12.1 |
| 6 | 34.6 |
| 7 | 298.1 |
| 8 | 52.7 |
| 9 | 98.3 |
| 10 | <0.2 |
| 11 | <4.1 |
| 12 | 4.0 |
| 13 | <4.1 |
| 14 | 6.6 |
| 15 | 38.2 |
| 16 | 11.6 |
| 17 | 68.5 |
| 18 | 15.9 |
| 19 | 4.9 |
| 20 | 61.9 |
| 21 | 68.6 |
| 22 | 86.0 |
| 23 | 12.3 |
| 24 | 8.3 |
| 25 | 36.3 |
| 26 | 13.7 |
| 27 | 37.2 |
| 28 | 46.6 |
| 29 | 64.7 |
| 30 | 17.4 |
| 31 | 74.5 |
| 32 | 19.3 |
| 33 | 11.8 |
| 34 | 12.3 |
| 35 | 36.9 |
| 36 | 26.2 |
| 37 | 12.5 |
| 38 | 13.6 |
| 39 | 10.3 |
| 40 | 119.6 |
| 41 | 43.2 |
| 42 | 54.6 |
| 43 | 106.6 |
| 44 | 263.7 |
| 45 | 39.5 |
| 46 | 114.4 |
| 47 | 117.1 |
| 48 | 218.7 |
| 49 | 97.8 |
| 50 | 81.2 |
| 51 | 52.4 |
| 52 | 59.0 |
| 53 | 109.6 |
| 54 | 333 |
| 55 | 35.7 |
| 56 | 26.3 |
| 57 | 32.8 |
| 58 | 141.0 |
| Crizotinib | 75.4-153.8 |
| LDK378* | 94.6-339.0 |

*LDK378 was prepared as example 7 of WO2008073687.

In Vivo Antitumor Activity

Male nude mice (6-week old) were housed in a specific pathogen-free room with a 12 h light/dark schedule at 20-25° C. and were fed an autoclaved chow diet and water ad libitum.

NCI-H2228 cells at a density of $5.1 \times 10^6$ in 200 μL were first implanted sc into the right flank of each nude mice and then allowed to grow to above 230 mm$^3$, the mice were randomly assigned into control and treatment groups (n=6 per group for compound treated group, n=12 per group for vehicle group). Vehicle control group were given vehicle alone, and treatment groups were received Compound 4, LDK378 or Crizotinib as indicated doses via oral administration once daily for 21 days. The mice tumor volumes in each group were measured twice per week.

The results are given in the Table 3 and FIG. 1.

TABLE 3

Effect on relative tumor volume

| Group | Mean relative tumor volume (RTV) ± S.E. | | | | | | |
|---|---|---|---|---|---|---|---|
| | D0 | D4 | D7 | D11 | D14 | D18 | D21 |
| Vehicle Control | 100.00 ± 0.00 | 151.74 ± 10.44 | 173.58 ± 8.81 | 214.45 ± 9.56 | 229.76 ± 11.06 | 241.34 ± 11.04 | 275.65 ± 17.77 |
| Compound 4, 10 mg/kg, QD | 100.00 ± 0.00 | 52.92 ± 3.59** | 36.55 ± 5.03** | 29.20 ± 5.18** | 18.82 ± 4.53** | 9.48 ± 2.64** | 5.28 ± 2.35** |
| LDK378, 20 mg/kg, QD | 100.00 ± 0.00 | 71.66 ± 4.52** | 56.79 ± 8.60** | 49.09 ± 8.81** | 48.58 ± 7.88** | 35.67 ± 7.17** | 31.44 ± 7.90** |
| Crizotinib, 50 mg/kg, QD | 100.00 ± 0.00 | 67.71 ± 3.20** | 54.10 ± 5.56** | 44.71 ± 5.98** | 42.69 ± 6.12** | 41.44 ± 6.35** | 43.69 ± 6.82** |

What is claimed is:

1. At least one compound of formula (I):

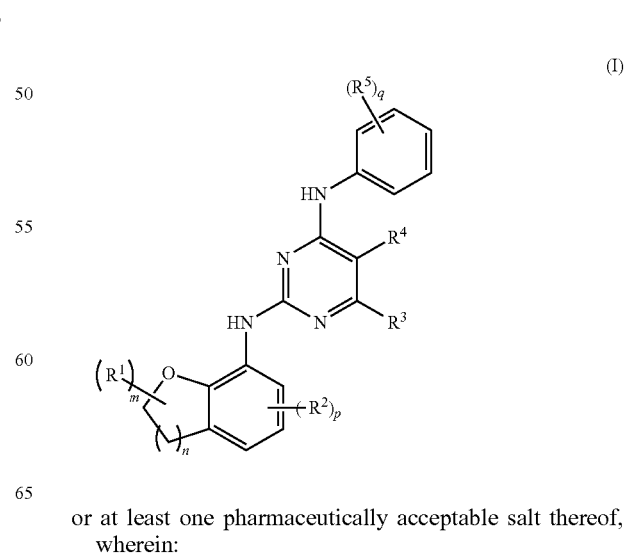

or at least one pharmaceutically acceptable salt thereof, wherein:

each $R^1$ is independently:
  hydrogen,
  halogen,
  hydroxyl,
  $C_{1-10}$ alkyl,
  $C_{3-10}$ cycloalkyl,
  $C_{3-10}$ cycloalkyl-alkyl,
  heterocyclyl,
  heterocyclylalkyl
  aryl,
  arylalkyl,
  heteroaryl, or
  heteroarylalkyl,
  wherein alkyl, cycloalkyl, and heterocyclyl are each unsubstituted or substituted with at least one substituent independently selected from $R^{6a}$, and wherein aryl and heteroaryl are each unsubstituted or substituted with at least one substituent independently selected from $R^{6b}$;
each $R^2$ is independently:
  $C_{1-10}$ alkyl or piperidinyl,
  wherein alkyl and piperidinyl are each unsubstituted or substituted with at least one substituent independently selected from $R^{6a}$;
each $R^3$ is independently:
  hydrogen,
  halogen,
  —CN,
  —NR$^7$R$^8$, or
  $C_{1-10}$ alkyl;
  wherein alkyl is unsubstituted or substituted with at least one substituent independently selected from $R^{6a}$;
each $R^4$ is independently:
  hydrogen,
  halogen,
  —CN,
  $C_{1-10}$ alkyl,
  $C_{2-10}$ alkenyl,
  $C_{2-10}$ alkynyl, or
  $C_{3-10}$ cycloalkyl;
  wherein $C_{1-10}$ alkyl, $C_{2-10}$ alkenyl, $C_{2-10}$ alkynyl, and $C_{3-10}$ cycloalkyl are each unsubstituted or substituted with at least one substituent independently selected from $R^{6a}$;
or $R^3$ and $R^4$ together with the carbon atoms to which they are attached form a 5-6 membered ring containing 0, 1, 2 or 3 heteroatoms independently selected from the group consisting of oxygen, sulfur and nitrogen, and optionally substituted with 1-2 $R^{6b}$ groups;
each $R^5$ is independently:
  $C_{1-10}$ alkyl,
  $C_{2-10}$ alkenyl,
  $C_{2-10}$ alkynyl,
  $C_{3-10}$ cycloalkyl,
  —OR$^8$,
  —NR$^7$S(O)$_r$R$^8$,
  —NO$_2$,
  halogen,
  —S(O)$_r$R$^7$,
  —SR$^8$,
  —S(O)$_2$OR$^7$,
  —OS(O)$_2$R$^8$,
  —S(O)$_r$NR$^7$R$^8$,
  —NR$^7$R$^8$,
  —O(CR$^9$R$^{10}$)$_t$NR$^7$R$^8$,
  —C(O)R$^7$,
  —CO$_2$R$^8$,
  —CO$_2$(CR$^9$R$^{10}$)$_t$CONR$^7$R$^8$,
  —OC(O)R$^7$,
  —CN,
  —C(O)NR$^7$R$^8$,
  —NR$^7$C(O)R$^8$,
  —OC(O)NR$^7$R$^8$,
  —NR$^7$C(O)OR$^8$,
  —NR$^7$C(O)NR$^7$R$^8$,
  —CR$^7$(N—OR$^8$),
  —CHF$_2$,
  —CF$_3$,
  —OCHF$_2$, or
  —OCF$_3$;
  wherein $C_{1-10}$ alkyl, $C_{2-10}$ alkenyl, $C_{2-10}$ alkynyl, and $C_{3-10}$ cycloalkyl are each unsubstituted or substituted with at least one substituent independently selected from $R^{6a}$;
each $R^{6a}$ is independently:
  $C_{1-10}$ alkyl,
  $C_{2-10}$ alkenyl,
  $C_{2-10}$ alkynyl,
  $C_{3-10}$ cycloalkyl,
  —OR$^8$,
  —NR$^7$S(O)$_r$R$^8$,
  —NO$_2$,
  halogen,
  —S(O)$_r$R$^7$,
  —SR$^8$,
  —S(O)$_2$OR$^7$,
  —OS(O)$_2$R$^8$,
  —S(O)$_r$NR$^7$R$^8$,
  —NR$^7$R$^8$,
  —(CR$^9$R$^{10}$)$_t$OR$^8$,
  —(CR$^9$R$^{10}$)$_t$NR$^7$R$^8$,
  —(CR$^9$R$^{10}$)$_t$SR$^8$,
  —(CR$^9$R$^{10}$)$_t$S(O)$_r$R$^8$,
  —(CR$^9$R$^{10}$)$_t$CO$_2$R$^8$,
  —(CR$^9$R$^{10}$)$_t$CONR$^7$R$^8$,
  —(CR$^9$R$^{10}$)$_t$NR$^7$CO$_2$R$^8$,
  —(CR$^9$R$^{10}$)$_t$OCONR$^7$R$^8$,
  —(CR$^9$R$^{10}$)$_t$NR$^7$CONR$^7$R$^8$,
  —(CR$^9$R$^{10}$)$_t$NR$^7$SO$_2$NR$^7$R$^8$,
  —O(CR$^9$R$^{10}$)$_t$NR$^7$R$^8$,
  —C(O)R$^7$,
  —C(O)(CR$^9$R$^{10}$)$_t$OR$^8$,
  —C(O)(CR$^9$R$^{10}$)$_t$NR$^7$R$^8$,
  —C(O)(CR$^9$R$^{10}$)$_t$SR$^8$,
  —C(O)(CR$^9$R$^{10}$)$_t$S(O)$_r$R$^8$,
  —CO$_2$R$^8$,
  —CO$_2$(CR$^9$R$^{10}$)$_t$CONR$^7$R$^8$,
  —OC(O)R$^7$,
  —CN,
  —C(O)NR$^7$R$^8$,
  —NR$^7$C(O)R$^8$,
  —OC(O)NR$^7$R$^8$,
  —NR$^7$C(O)OR$^8$,
  —NR$^7$C(O)NR$^7$R$^8$,
  —CR$^7$(N—OR$^8$),
  —CHF$_2$,
  —CF$_3$,
  —OCHF$_2$, or
  —OCF$_3$;
each $R^{6b}$ is independently:
  $R^{6a}$,
  aryl,
  aryl-$C_{1-4}$ alkyl,
  heteroaryl, or
  heteroaryl-$C_{1-4}$ alkyl;

each $R^7$ and each W are independently:
  hydrogen,
  $C_{1-10}$ alkyl,
  $C_{2-10}$ alkenyl,
  $C_{2-10}$ alkynyl,
  $C_{3-10}$ cycloalkyl,
  cycloalkyl-$C_{1-10}$ alkyl;
  heterocyclyl,
  heterocyclyl-$C_{1-10}$ alkyl,
  aryl,
  heteroaryl,
  aryl-$C_{1-10}$ alkyl, or
  heteroaryl-$C_{1-10}$ alkyl;
  wherein alkyl, alkenyl, alkynyl, cycloalkyl, and heterocyclyl are each unsubstituted or substituted with at least one substituent independently selected from $R^{6a}$, and aryl and heteroaryl are each unsubstituted or substituted with at least one substituent independently selected from $R^{6b}$; or
$R^7$ and $R^8$ together with the atom(s) to which they are attached form a heterocyclic ring of 4 to 7 members containing 0, 1, or 2 additional heteroatoms independently selected from the group consisting of oxygen, sulfur and $NR^{11}$, each $R^7$ and $R^8$ may be unsubstituted or substituted on a carbon or nitrogen atom with at least one substituent independently selected from $R^{12}$;
each $R^9$ and each $R^{10}$ are independently:
  hydrogen,
  $C_{1-10}$ alkyl,
  $C_{2-10}$ alkenyl,
  $C_{2-10}$ alkynyl,
  $C_{3-10}$ cycloalkyl,
  cycloalkyl-$C_{1-10}$ alkyl,
  heterocyclyl,
  heterocyclyl-$C_{1-10}$ alkyl,
  aryl,
  heteroaryl,
  aryl-$C_{1-10}$ alkyl, or
  heteroaryl-$C_{1-10}$ alkyl; or
$R^9$ and $R^{19}$ together with the carbon to which they are attached form a ring of 3 to 7 members containing 0, 1, or 2 heteroatoms independently selected from the group consisting of oxygen, sulfur and nitrogen;
each $R^{11}$ is independently:
  hydrogen,
  $C_{1-10}$ alkyl,
  $C_{3-10}$ cycloalkyl,
  $C_{3-10}$ cycloalkyl-$C_{1-4}$ alkyl,
  heterocyclyl,
  heterocyclyl-$C_{1-4}$ alkyl,
  aryl,
  aryl-$C_{1-4}$ alkyl,
  heteroaryl,
  heteroaryl-$C_{1-4}$ alkyl,
  —$S(O)_rR^7$,
  —$C(O)R^7$,
  —$CO_2R^7$,
  —$CO_2(CR^9R^{10})_tCONR^7R^8$, or
  —$C(O)NR^7R^8$;
each $R^{12}$ is independently:
  halogen,
  $C_{1-10}$ alkyl,
  $C_{3-10}$ cycloalkyl,
  $C_{3-10}$ cycloalkylalkyl,
  heterocyclyl,
  heterocyclylalkyl,
  aryl,
  aryl-$C_{1-4}$ alkyl,
  heteroaryl,
  heteroaryl-$C_{1-4}$ alkyl,
  —$OR^7$,
  —$NR^7S(O)_rR^8$,
  —$S(O)_rR^7$,
  —$SR^7$,
  —$S(O)_2OR^7$,
  —$OS(O)_2R^7$,
  —$S(O)_rNR^7R^8$,
  —$NR^7R^8$,
  —$O(CR^9R^{10})_tNR^7R^8$,
  —$C(O)R^7$,
  —$CO_2R^8$,
  —$CO_2(CR^9R^{10})_tCONR^7R^8$,
  —$OC(O)R^7$,
  —CN,
  —$C(O)NR^7R^8$,
  —$NR^7C(O)R^8$,
  —$OC(O)NR^7R^8$,
  —$NR^7C(O)OR^8$,
  —$NR^7C(O)NR^7R^8$,
  —$CHF_2$,
  —$CF_3$,
  —$OCHF_2$, or
  —$OCF_3$;
each m is independently 0, 1, or 2;
each n is independently 1, 2, or 3;
each p is independently 2;
each q is independently 0, 1, 2, or 3;
each r is independently 1 or 2;
each t is independently 1, 2, or 3.

2. At least one compound of claim 1 or at least one pharmaceutically acceptable salt thereof, wherein $R^1$ is hydrogen or $C_{1-10}$ alkyl, wherein alkyl is unsubstituted or substituted with at least one substituent independently selected from the group consisting of hydroxyl and $C_{1-10}$ alkoxy.

3. At least one compound of claim 1 or at least one pharmaceutically acceptable salt thereof, wherein m is 0.

4. At least one compound of claim 1 or at least one pharmaceutically acceptable salt thereof, wherein $R^1$ is $C_{1-10}$ alkyl, wherein alkyl is unsubstituted or substituted with at least one substituent independently selected from the group consisting of hydroxyl and $C_{1-10}$ alkoxy.

5. At least one compound of claim 1 or at least one pharmaceutically acceptable salt thereof, wherein m is 1.

6. At least one compound of claim 5 or at least one pharmaceutically acceptable salt thereof, wherein $R^1$ is methyl, hydroxymethyl, or methoxymethyl.

7. At least one compound of claim 1 or at least one pharmaceutically acceptable salt thereof, wherein each $R^2$ is independently selected from the group consisting of methyl and 4-piperidinyl.

8. At least one compound of claim 7 or at least one pharmaceutically acceptable salt thereof, wherein each $R^2$ is independently methyl or 4-piperidinyl, wherein 4-piperidinyl is unsubstituted or substituted with at least one substituent independently selected from $R^{6a}$, wherein $R^{6a}$ is independently selected from the group consisting of $C_{1-10}$ alkyl, —$C(O)R^7$, —$S(O)_rR^7$, —$(CR^9R^{10})_tCO_2R^8$, —$C(O)(CR^9R^{10})_tOR^8$, —$C(O)(CR^9R^{10})_tNR^7R^8$, —$(CR^9R^{10})_tOR^8$, —$(CR^9R^{10})_tCONR^7R^8$, —$(CR^9R^{10})_tS(O)_rR^8$, —$CO_2R^8$, —$C(O)NR^7R^8$, and —$(CR^9R^{10})_tOR^8$.

9. At least one compound of claim 1 or at least one pharmaceutically acceptable salt thereof, wherein $R^3$ is hydrogen.

10. At least one compound of claim 1 or at least one pharmaceutically acceptable salt thereof, wherein $R^4$ is independently hydrogen, $C_{1-10}$ alkyl, or halogen.

11. At least one compound of claim 10 or at least one pharmaceutically acceptable salt thereof, wherein $R^4$ is independently selected from halogen.

12. At least one compound of claim 11 or at least one pharmaceutically acceptable salt thereof, wherein $R^4$ is chlorine.

13. At least one compound of claim 1 or at least one pharmaceutically acceptable salt thereof, wherein $R^3$ and $R^4$ together with the carbon atoms to which they are attached form a 5 membered ring containing 2 nitrogen atoms, wherein the 5-membered ring is optionally substituted with 1-2 $C_{1-10}$ alkyl.

14. At least one compound of claim 1 or at least one pharmaceutically acceptable salt thereof, wherein $R^3$ and $R^4$ together with the carbon atoms to which they are attached form pyrazolo.

15. At least one compound of claim 1 or at least one pharmaceutically acceptable salt thereof, wherein $R^5$ is —S(O)$_q$R$^7$.

16. At least one compound of claim 15 or at least one pharmaceutically acceptable salt thereof, wherein $R^5$ is —S(O)$_2$R$^7$, wherein $R^7$ is $C_{1-10}$ alkyl, and q is 1.

17. At least one compound of claim 16 or at least one pharmaceutically acceptable salt thereof, wherein $R^5$ is —S(O)$_2$R$^7$, wherein $R^7$ is isopropyl.

18. At least one compound of claim 1 or at least one pharmaceutically acceptable salt thereof, wherein n is 1.

19. At least one compound selected from the group consisting of:
- N-4-(2-(isopropylsulfonyl)phenyl)-3-methyl-N-6-(5-methyl-4-(piperidin-4-yl)-2,3-dihydrobenzofuran-7-yl)-1H-pyrazolo[3,4-d]pyrimidine-4,6-diamine;
- N-4-(2-(isopropylsulfonyl)phenyl)-3-methyl-N-6-(5-methyl-4-(1-methylpiperidin-4-yl)-2,3-dihydrobenzofuran-7-yl)-1H-pyrazolo[3,4-d]pyrimidine-4,6-diamine;
- (R)—N-6-(2,5-dimethyl-4-(piperidin-4-yl)-2,3-dihydrobenzofuran-7-yl)-N-4-(2-(isopropylsulfonyl)phenyl)-3-methyl-1H-pyrazolo[3,4-d]pyrimidine-4,6-diamine;
- (R)—N-6-(2,5-dimethyl-4-(1-methylpiperidin-4-yl)-2,3-dihydrobenzofuran-7-yl)-N-4-(2-(isopropylsulfonyl)phenyl)-3-methyl-1H-pyrazolo[3,4-d]pyrimidine-4,6-diamine;
- (S)—N-6-(2,5-dimethyl-4-(piperidin-4-yl)-2,3-dihydrobenzofuran-7-yl)-N-4-(2-(isopropylsulfonyl)phenyl)-3-methyl-1H-pyrazolo[3,4-d]pyrimidine-4,6-diamine;
- (S)—N-6-(2,5-dimethyl-4-(1-methylpiperidin-4-yl)-2,3-dihydrobenzofuran-7-yl)-N-4-(2-(isopropylsulfonyl)phenyl)-3-methyl-1H-pyrazolo[3,4-d]pyrimidine-4,6-diamine;
- (7-(4-(2-(isopropylsulfonyl)phenylamino)-3-methyl-1H-pyrazolo[3,4-d]pyrimidin-6-ylamino)-5-methyl-4-(piperidin-4-yl)-2,3-dihydrobenzofuran-2-yl)methanol;
- N-4-(2-(isopropylsulfonyl)phenyl)-N-6-(2-(methoxymethyl)-5-methyl-4-(piperidin-4-yl)-2,3-dihydrobenzofuran-7-yl)-3-methyl-1H-pyrazolo[3,4-d]pyrimidine-4,6-diamine;
- (R)-5-chloro-N-2-(2,5-dimethyl-4-(piperidin-4-yl)-2,3-dihydrobenzofuran-7-yl)-N-4-(2-(isopropylsulfonyl)phenyl)pyrimidine-2,4-diamine;
- (R)-5-chloro-N-2-(2,5-dimethyl-4-(1-methylpiperidin-4-yl)-2,3-dihydrobenzofuran-7-yl)-N-4-(2-(isopropylsulfonyl)phenyl)pyrimidine-2,4-diamine;
- (S)-5-chloro-N-2-(2,5-dimethyl-4-(piperidin-4-yl)-2,3-dihydrobenzofuran-7-yl)-N-4-(2-(isopropylsulfonyl)phenyl)pyrimidine-2,4-diamine;
- (S)-5-chloro-N-2-(2,5-dimethyl-4-(1-methylpiperidin-4-yl)-2,3-dihydrobenzofuran-7-yl)-N-4-(2-(isopropylsulfonyl)phenyl)pyrimidine-2,4-diamine;
- 5-chloro-N-4-(2-(isopropylsulfonyl)phenyl)-N-2-(5-methyl-4-(piperidin-4-yl)-2,3-dihydrobenzofuran-7-yl)pyrimidine-2,4-diamine;
- 5-chloro-N-4-(2-(isopropylsulfonyl)phenyl)-N-2-(5-methyl-4-(1-methylpiperidin-4-yl)-2,3-dihydrobenzofuran-7-yl)pyrimidine-2,4-diamine;
- (S)-1-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)ethanone;
- (R)-1-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)ethanone;
- (S)-5-chloro-N-2-(2,5-dimethyl-4-(1-(methylsulfonyl)piperidin-4-yl)-2,3-dihydrobenzofuran-7-yl)-N-4-(2-(isopropylsulfonyl)phenyl)pyrimidine-2,4-diamine;
- (R)-5-chloro-N-2-(2,5-dimethyl-4-(1-(methylsulfonyl)piperidin-4-yl)-2,3-dihydrobenzofuran-7-yl)-N-4-(2-(isopropylsulfonyl)phenyl)pyrimidine-2,4-diamine;
- (S)-2-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)acetic acid;
- (R)-2-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)acetic acid;
- (S)-2-amino-1-(4-((S)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)propan-1-one;
- (S)-2-amino-1-(4-((R)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)propan-1-one;
- (R)-1-(4-((R)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)propan-2-ol;
- (S)-1-(4-((R)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)propan-2-ol;
- (S)-2-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)acetamide;
- (R)-2-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)acetamide;
- (S)-2-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-N,N-dimethylacetamide;
- (R)-2-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-N,N-dimethylacetamide;
- (S)-5-chloro-N-2-(2,5-dimethyl-4-(1-(2-(methylsulfonyl)ethyl)piperidin-4-yl)-2,3-dihydrobenzofuran-7-yl)-N-4-(2-(isopropylsulfonyl)phenyl)pyrimidine-2,4-diamine;
- (R)-5-chloro-N-2-(2,5-dimethyl-4-(1-(2-(methylsulfonyl)ethyl)piperidin-4-yl)-2,3-dihydrobenzofuran-7-yl)-N-4-(2-(isopropylsulfonyl)phenyl)pyrimidine-2,4-diamine;

(S)-5-chloro-N-4-(2-(isopropylsulfonyl)phenyl)-N-2-(4-(1-(2-methoxyethyl)piperidin-4-yl)-2,5-dimethyl-2,3-dihydrobenzofuran-7-yl)pyrimidine-2,4-diamine;

(R)-5-chloro-N-4-(2-(isopropylsulfonyl)phenyl)-N-2-(4-(1-(2-methoxyethyl)piperidin-4-yl)-2,5-dimethyl-2,3-dihydrobenzofuran-7-yl)pyrimidine-2,4-diamine;

(R)-2-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)ethanol;

(S)-2-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)ethanol;

(R)-1-(4-((S)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)propan-2-ol;

(S)-1-(4-((S)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)propan-2-ol;

(R)-1-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-2-hydroxyethanone;

(S)-1-(4-((R)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-2-hydroxypropan-1-one;

(R)-1-(4-((R)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-2-hydroxypropan-1-one;

(S)-methyl 4-(7-((5-chloro-4-((2-(isopropylsulfonyl)phenyl)amino)pyrimidin-2-yl)amino)-2,5-dimethyl-2,3-dihydrobenzofuran-4-yl)piperidine-1-carboxylate;

(S)-ethyl 2-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)acetate;

(S)-2-amino-1-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)ethanone;

(S)-4-(7-((5-chloro-4-((2-(isopropylsulfonyl)phenyl)amino)pyrimidin-2-yl)amino)-2,5-dimethyl-2,3-dihydrobenzofuran-4-yl)piperidine-1-carboxamide;

(S)-1-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-2-(methylamino)ethanone;

(S)-1-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-2-(dimethylamino)ethanone;

(S)-(7-((5-chloro-4-((2-(isopropylsulfonyl)phenyl)amino)pyrimidin-2-yl)amino)-2,5-dimethyl-2,3-dihydrobenzofuran-4-yl)(piperazin-1-yl)methanone;

(S)-(7-((5-chloro-4-((2-(isopropylsulfonyl)phenyl)amino)pyrimidin-2-yl)amino)-2,5-dimethyl-2,3-dihydrobenzofuran-4-yl)(4-methylpiperazin-1-yl)methanone;

(S)-(7-((5-chloro-4-((2-(isopropylsulfonyl)phenyl)amino)pyrimidin-2-yl)amino)-2,5-dimethyl-2,3-dihydrobenzofuran-4-yl)(morpholino)methanone;

(R)-1-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)propan-1-one;

(R)-1-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-2-methylpropan-1-one;

(R)-(4-(7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)(cyclopropyl)methanone;

(R)-5-chloro-N-2-(4-(1-(ethylsulfonyl)piperidin-4-yl)-2,5-dimethyl-2,3-dihydrobenzofuran-7-yl)-N-4-(2-(isopropylsulfonyl)phenyl)pyrimidine-2,4-diamine;

(R)-5-chloro-N-4-(2-(isopropylsulfonyl)phenyl)-N-2-(4-(1-(isopropylsulfonyl)piperidin-4-yl)-2,5-dimethyl-2,3-dihydrobenzofuran-7-yl)pyrimidine-2,4-diamine;

(R)-5-chloro-N-2-(4-(1-(cyclopropylsulfonyl)piperidin-4-yl)-2,5-dimethyl-2,3-dihydrobenzofuran-7-yl)-N-4-(2-(isopropylsulfonyl)phenyl)pyrimidine-2,4-diamine;

(R)-1-(4-((S)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-2-methoxypropan-1-one;

(R)-1-(4-((R)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-2-methoxypropan-1-one;

(S)-1-(4-((R)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-2-methoxypropan-1-one;

(S)-1-(4-((S)-7-((5-chloro-4-((2-(isopropylsulfonyl)phenyl)amino)pyrimidin-2-yl)amino)-2,5-dimethyl-2,3-dihydrobenzofuran-4-yl)piperidin-1-yl)-2-methoxypropan-1-one; and pharmaceutically acceptable salts thereof.

20. A pharmaceutical composition, comprising at least one compound of claim 1, or at least one pharmaceutically acceptable salt thereof, and at least one pharmaceutically acceptable carrier.

* * * * *

UNITED STATES PATENT AND TRADEMARK OFFICE
CERTIFICATE OF CORRECTION

Page 1 of 1

PATENT NO. : 9,206,166 B2
APPLICATION NO. : 14/071953
DATED : December 8, 2015
INVENTOR(S) : Wang et al.

It is certified that error appears in the above-identified patent and that said Letters Patent is hereby corrected as shown below:

In the Claims
Claim 1, Col. 107, Line 1, "Ware" should read --$R^8$ are--.
Claim 1, Col. 107, Line 40, "$R^{19}$" should read --$R^{10}$--.

Signed and Sealed this
Twenty-ninth Day of March, 2016

Michelle K. Lee
*Director of the United States Patent and Trademark Office*